(12) United States Patent
Yang et al.

(10) Patent No.: US 11,608,311 B2
(45) Date of Patent: Mar. 21, 2023

(54) NITROGEN-CONTAINING COMPOUND, ORGANIC ELECTROLUMINESCENT DEVICE, AND ELECTRONIC APPARATUS

(71) Applicant: SHAANXI LIGHTE OPTOELECTRONICS MATERIAL CO., LTD., Xi'an (CN)

(72) Inventors: Min Yang, Xi'an (CN); Tiantian Ma, Xi'an (CN); Peng Nan, Xi'an (CN)

(73) Assignee: SHAANXI LIGHTE OPTOELECTRONICS MATERIAL CO., LTD., Xi'an (CN)

( * ) Notice: Subject to any disclaimer, the term of this patent is extended or adjusted under 35 U.S.C. 154(b) by 0 days.

(21) Appl. No.: 17/623,211

(22) PCT Filed: Oct. 22, 2020

(86) PCT No.: PCT/CN2020/122846
§ 371 (c)(1),
(2) Date: Dec. 27, 2021

(87) PCT Pub. No.: WO2021/120835
PCT Pub. Date: Jun. 24, 2021

(65) Prior Publication Data
US 2022/0388944 A1 Dec. 8, 2022

(30) Foreign Application Priority Data

Dec. 20, 2019 (CN) .......................... 201911328979.4
Sep. 3, 2020 (CN) .......................... 202010914703.0

(51) Int. Cl.
C07C 211/54 (2006.01)
H01L 51/00 (2006.01)
(Continued)

(52) U.S. Cl.
CPC .......... C07C 211/54 (2013.01); C07D 211/82 (2013.01); C07D 213/74 (2013.01);
(Continued)

(58) Field of Classification Search
CPC .. C07C 211/54; C07C 2603/50; H01L 51/006
See application file for complete search history.

(56) References Cited

U.S. PATENT DOCUMENTS 9,466,800 B2 10/2016 Mizuki et al.
9,553,273 B2 1/2017 Ogita et al.
(Continued)

FOREIGN PATENT DOCUMENTS

CN 101018760 A 8/2007
CN 102040528 A 5/2011
(Continued)

OTHER PUBLICATIONS

English-language translation of WO-2020080849-A1.*
(Continued)

Primary Examiner — Vu A Nguyen
(74) Attorney, Agent, or Firm — Anova Law Group, PLLC

(57) ABSTRACT

Provided is the nitrogen-containing compound shown in Chemical formula 1, an organic electroluminescent device, and an electronic apparatus, relating to the technical field of
(Continued)

organic materials. The nitrogen-containing compound can improve the performance of the organic electroluminescent device.

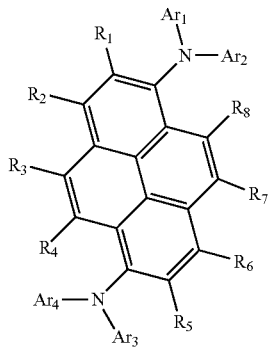

Chemical formula 1

12 Claims, 1 Drawing Sheet

(51) Int. Cl.
H01L 51/50 (2006.01)
C07D 211/82 (2006.01)
C07D 213/74 (2006.01)
C07D 307/91 (2006.01)
C07D 333/76 (2006.01)
C07D 471/04 (2006.01)

(52) U.S. Cl.
CPC ......... *C07D 307/91* (2013.01); *C07D 333/76* (2013.01); *C07D 471/04* (2013.01); *H01L 51/0052* (2013.01); *H01L 51/0054* (2013.01); *H01L 51/0056* (2013.01); *H01L 51/0059* (2013.01); *H01L 51/0064* (2013.01); *H01L 51/0072* (2013.01); *H01L 51/0073* (2013.01); *H01L 51/0074* (2013.01); *H01L 51/5012* (2013.01); *H01L 51/5024* (2013.01); *C07B 2200/05* (2013.01)

(56) References Cited

U.S. PATENT DOCUMENTS

| | | |
|---|---|---|
| 9,741,938 B2 | 8/2017 | Mizuki et al. |
| 10,665,788 B2 | 5/2020 | Kwon et al. |
| 10,985,324 B2 | 4/2021 | Ma et al. |
| 2007/0292714 A1 | 12/2007 | Funahashi |
| 2019/0074449 A1 | 3/2019 | Chen et al. |

FOREIGN PATENT DOCUMENTS

| | | |
|---|---|---|
| CN | 102232068 A | 11/2011 |
| CN | 103304428 A | 9/2013 |
| CN | 104795495 A | 7/2015 |
| CN | 107459466 A | 12/2017 |
| CN | 108129332 A | 6/2018 |
| CN | 109651174 A | 4/2019 |
| CN | 110128279 A | 8/2019 |
| CN | 110467536 A | 11/2019 |
| CN | 111377853 A | 7/2020 |
| CN | 112074509 A | 12/2020 |
| KR | 20190118515 A | 10/2019 |
| WO | 2020080849 A1 | 4/2020 |

OTHER PUBLICATIONS

English-language translation of CN-110128279-A.*
English-language translation of CN-102232068-A.*
The World Intellectual Property Organization (WIPO) International Search Report for PCT/CN2020/122846 dated Jan. 20, 2021 6 Pages (with translation).
China National Intellectual Property Administration Notification of the first Office Action for CN 202010914703.0 dated Mar. 4, 2021 19 pages (with translation).

* cited by examiner

NITROGEN-CONTAINING COMPOUND, ORGANIC ELECTROLUMINESCENT DEVICE, AND ELECTRONIC APPARATUS

CROSS REFERENCE TO RELATED APPLICATIONS

The present application is a national phase entry under 35 U.S.C. § 371 of International Application No. PCT/CN2020/122846, filed on Oct. 22, 2020, which claims priority to Chinese Patent Application No. CN201911328979.4 filed on Dec. 20, 2019 and entitled "NITROGEN-CONTAINING COMPOUND, ORGANIC ELECTROLUMINESCENT ELEMENT, AND ELECTRONIC APPARATUS", and to Chinese Patent Application No. CN202010914703.0 filed on Sep. 3, 2020 and entitled "NITROGEN-CONTAINING COMPOUND, ORGANIC ELECTROLUMINESCENT ELEMENT, AND ELECTRONIC APPARATUS", contents of which are incorporated herein by reference in its entirety as part of the present application.

TECHNICAL FIELD

The present disclosure relates to the technical field of organic materials, and in particular to a nitrogen-containing compound, an organic electroluminescent device using the nitrogen-containing compound, and an electronic apparatus using the organic electroluminescent device.

BACKGROUND

Organic electroluminescent devices, also known as organic light-emitting diodes (OLEDs), refer to the phenomenon that organic light-emitting materials are excited by a current to emit light under the action of an electric field. The phenomenon is a process of converting electrical energy into light energy. Compared with inorganic light-emitting materials, Organic light-emitting diode OLED has the advantages of active light emission, large optical path range, low driving voltage, high luminance, high efficiency, low energy consumption, simple production process, and the like. Due to these advantages, organic light-emitting materials and devices have become one of the most popular research subjects in the scientific and industrial circles.

In organic electroluminescent device, a blue light-emitting material is an indispensable part for display and lighting, which plays a very important role in reducing the energy consumption of display and lighting devices and enhancing the overall effect of the devices. However, the development of blue light-emitting materials has always been a problem. At present, there are few types of blue phosphorescent materials with poor stability, and thus the development of such materials is of great significance. Blue light-emitting materials disclosed in Chinese Patents CN108129332A, US20190074449A, and CN109651174A show improved light-emitting characteristics, but fail to meet actual needs.

SUMMARY

The present disclosure is intended to provide a nitrogen-containing compound, an organic electroluminescent device, and an electronic apparatus, which can improve the performance of the organic electroluminescent device and the electronic apparatus.

To achieve the objective of the present disclosure, the present disclosure adopts the following technical solutions:

A first aspect of the present disclosure provides a nitrogen-containing compound having a structure shown in Chemical formula 1:

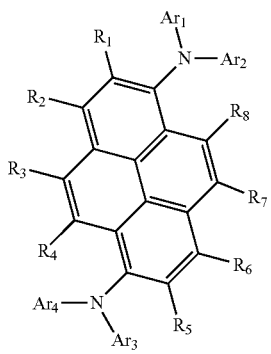

Chemical formula 1 wherein, $Ar_1$, $Ar_2$, $Ar_3$, and $Ar_4$ are the same or different, and are respectively independently selected from: a substituted or unsubstituted aryl with 6 to 30 carbon atoms, or a substituted or unsubstituted heteroaryl with 3 to 30 carbon atoms; and at least one of $Ar_1$, $Ar_2$, $Ar_3$, and $Ar_4$ is

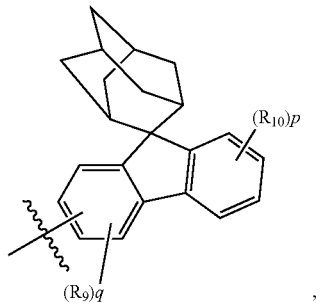

wherein,

represents a chemical bond;

p is selected from: 1, 2, 3, or 4, and when p is greater than or equal to 2, any two $R_{10}$ groups are the same or different; and q is selected from: 1, 2, or 3, and when q is greater than or equal to 2, any two $R_9$ groups are the same or different; and $R_1$ to $R_{10}$ are the same or different, and are respectively independently selected from: hydrogen, deuterium, a halogen, a cyano, a substituted or unsubstituted silyl, a substituted or unsubstituted alkyl with 1 to 10 carbon atoms, a substituted or unsubstituted aryl with 6 to 30 carbon atoms, a substituted or unsubstituted heteroaryl with 3 to 30 carbon atoms, or a substituted or unsubstituted cycloalkyl with 1 to 20 carbon atoms.

A second aspect of the present disclosure provides an organic electroluminescent device, comprising an anode and a cathode that are arranged oppositely, and a functional layer arranged between the anode and the cathode, where the functional layer includes the nitrogen-containing compound described above.

A third aspect of the present disclosure provides an electronic apparatus, comprising the organic electroluminescent device described above.

The nitrogen-containing compound of the present disclosure includes pyrenyl and spiro(adamantyl-fluorenyl). The pyrenyl has a large rigid conjugated structure, strong chemical stability, blue light emission, high fluorescence quantum efficiency and other excellent fluorescence properties, and high thermal stability. In the present disclosure, in order to avoid the aggregation of pyrenyl, pyrenyl is modified with large groups to avoid π-aggregation or exciplex resulting from the direct accumulation of conjugate planes through steric hindrance. An arylamine compound with spiro(adamantyl-fluorenyl) has a large molecular weight, which can effectively increase a glass transition temperature of the nitrogen-containing compound. Moreover, a structure of the arylamine compound has large steric hindrance, which makes the nitrogen-containing compound difficult to crystallize or agglomerate, such that the nitrogen-containing compound has a long life span in the organic electroluminescent device. The nitrogen atom on the arylamine has a strong electron-donating ability, and can improve the hole mobility, such that electrons and holes move rapidly to a recombination region and recombine for light emission, and finally reach a dynamic balance, thereby the efficiency of the organic electroluminescent device is improved.

BRIEF DESCRIPTION OF THE DRAWINGS

The above and other features and advantages of the present disclosure will become more apparent by describing exemplary embodiments thereof in detail with reference to the accompanying figures.

REFERENCE NUMERALS IN THE FIGURES

Figure 1:
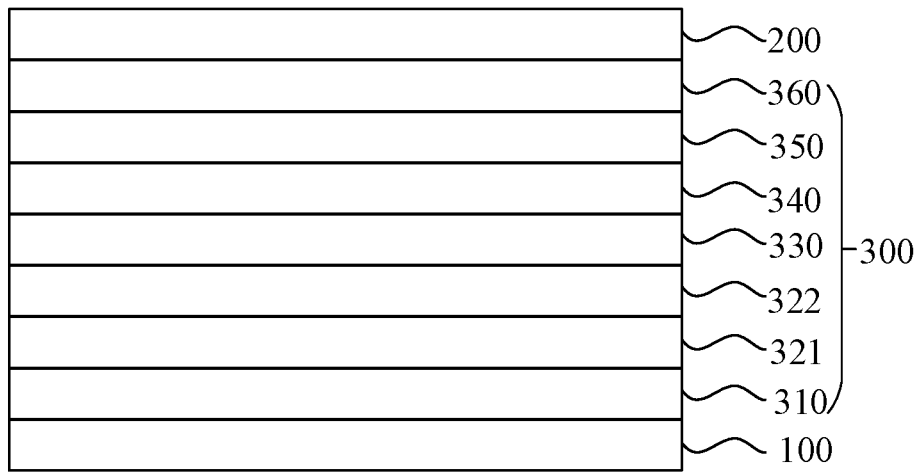
FIG. 1 is a schematic structure diagram of an organic electroluminescent device according to an embodiment of the present disclosure.

100: Anode; 200: Cathode; 300: Functional layer; 310: Hole injection layer; 321: Hole transport layer; 322: Electron blocking layer; 330: Organic electroluminescent layer; 340: Hole blocking layer; 350: Electron transport layer; 360: Electron injection layer; 400: Electronic apparatus.

DETAILED DESCRIPTION

Exemplary embodiments will be described below comprehensively with reference to the accompanying figures. However, the exemplary embodiments can be implemented in various forms and should not be construed as being limited to embodiments described herein. On the contrary, these embodiments are provided such that the present disclosure is comprehensive and complete and the concept of the exemplary embodiments is fully conveyed to those skilled in the art. The described features, structures, or characteristics may be incorporated into one or more embodiments in any suitable manner. In the following description, many specific details are provided to give a full understanding of the embodiments of the present disclosure.

In the figures, the thickness of regions and layers may be exaggerated for clarity. The same reference numerals in the figures indicate the same or similar structures, and thus their detailed descriptions will be omitted.

The described features, structures, or characteristics may be incorporated into one or more embodiments in any suitable manner. In the following description, many specific details are provided to give a full understanding of the embodiments of the present disclosure. However, those skilled in the art will be aware that the technical solutions of the present disclosure may be practiced without one or more of the specific details, or other methods, components, materials, and the like may be used. In other cases, well-known structures, materials, or operations are not shown or described in detail to avoid obscuring the main technical ideas of the present disclosure.

The present disclosure provides a nitrogen-containing compound having a structure shown in Chemical formula 1:

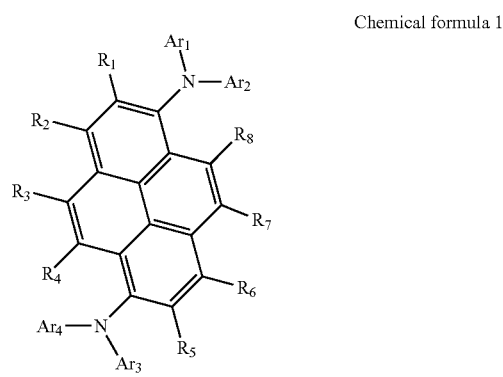

Chemical formula 1 wherein, $Ar_1$, $Ar_2$, $Ar_3$, and $Ar_4$ are the same or different, and are each independently selected from: a substituted or unsubstituted aryl with 6 to 30 carbon atoms, or a substituted or unsubstituted heteroaryl with 3 to 30 carbon atoms; and at least one of $Ar_1$, $Ar_2$, $Ar_3$, and $Ar_4$ is

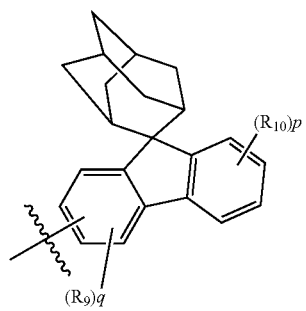

wherein,

represents a chemical bond;

p is selected from: 1, 2, 3, or 4, and when p is greater than or equal to 2, any two $R_{10}$ groups are the same or different;

q is selected from: 1, 2, or 3, and when q is greater than or equal to 2, any two $R_9$ groups are the same or different; and $R_1$ to $R_{10}$ are the same or different, and are each independently selected from: hydrogen, deuterium, a halogen, a cyano, a substituted or unsubstituted silyl, a substituted or unsubstituted alkyl with 1 to 10 carbon atoms, a substituted or unsubstituted aryl with 6 to 30 carbon atoms, a substituted or unsubstituted heteroaryl with 3 to 30 carbon atoms, or a substituted or unsubstituted cycloalkyl with 1 to 20 carbon atoms.

In the present disclosure, "at least one of $Ar_1$, $Ar_2$, $Ar_3$, and $Ar_4$ is

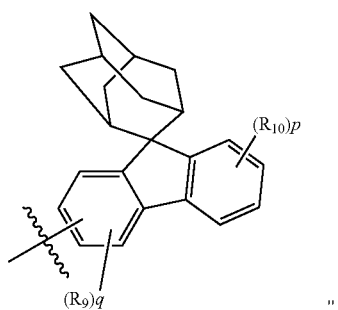

" means that one of $Ar_1$, $Ar_2$, $Ar_3$, and $Ar_4$ is

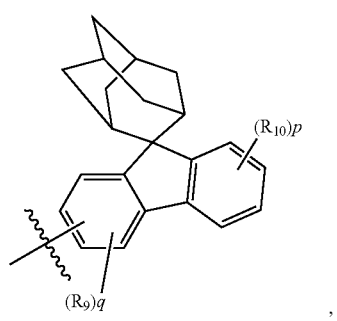

or two of $Ar_1$, $Ar_2$, $Ar_3$, and $Ar_4$ are or three of $Ar_1$, $Ar_2$, $Ar_3$, and $Ar_4$ are

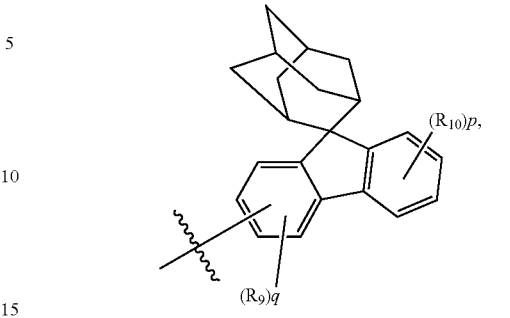

or four of $Ar_1$, $Ar_2$, $Ar_3$, and $Ar_4$ are

In the present disclosure, silyl refers to trialkylsilyl or triarylsilyl, and specific examples thereof include, but are not limited to, trimethylsilyl, triethylsilyl, triphenylsilyl and the like.

In the present disclosure, when $R_9$ and $R_{10}$ are hydrogen, spiro(adamantyl-fluorenyl) is not substituted.

The nitrogen-containing compound of the present disclosure includes pyrenyl and spiro(adamantyl-fluorenyl). The pyrenyl has a large rigid conjugated structure, strong chemical stability, blue light emission, high fluorescence quantum efficiency and other excellent fluorescence properties, and high thermal stability. In the present disclosure, in order to avoid the aggregation of pyrenyl, pyrenyl is modified with large groups to avoid R-aggregation or exciplex resulting from the direct accumulation of conjugate planes through steric hindrance. An arylamine compound with spiro(adamantyl-fluorenyl) has a large molecular weight, which can effectively increase a glass transition temperature of the nitrogen-containing compound. Moreover, a structure of the arylamine compound has large steric hindrance, which makes the nitrogen-containing compound difficult to crystallize or agglomerate, such that the nitrogen-containing compound has a long life span in the organic electroluminescent device. The nitrogen atom on the arylamine has a strong electron-donating ability, and can improve the hole mobility, such that electrons and holes move rapidly to a recombination region and recombine for light emission, and finally reach a dynamic balance, thereby the efficiency of the organic electroluminescent device is improved.

The description manners used in the present disclosure such as "each . . . is independently", " . . . is respectively independently selected from:" and " . . . is independently selected from the group consisting of" can be used interchangeably, and should be understood in a broad sense, which can mean that, in different groups, specific options expressed by the same symbols do not affect each other, or in the same group, specific options expressed by the same symbols do not affect each other. For example, "

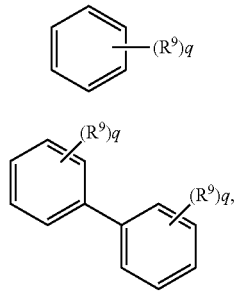

formula Q-1 formula Q-2 where q is independently 0, 1, 2, or 3, and substituents R" is each independently selected from: hydrogen, deuterium, fluorine, or chlorine" means that, in formula Q-1, there are q substituents R" on the benzene ring, the substituents R" can be the same or different, and options for each substituent R" do not affect each other; and in formula Q-2, there are q substituents R" on each benzene ring of the biphenyl, the numbers q of substituents R" on the two benzene rings can be the same or different, the substituents R" can be the same or different, and options for each substituent R" do not affect each other.

In the present disclosure, the term "substituted or unsubstituted" means that a functional group after the term may have or may not have a substituent (hereinafter, for ease of description, substituents are collectively referred to as Rc). For example, the "substituted or unsubstituted aryl" refers to Rc-substituted aryl or unsubstituted aryl. For example, the above-mentioned substituent Rc can be selected from: deuterium, fluorine, chlorine, bromine, cyano, heteroaryl with 3 to 20 carbon atoms, aryl with 6 to 20 carbon atoms, trialkylsilyl with 3 to 12 carbon atoms, arylsilyl with 8 to 12 carbon atoms, alkyl with 1 to 10 carbon atoms, haloalkyl with 1 to 10 carbon atoms, alkenyl with 2 to 6 carbon atoms, alkynyl with 2 to 6 carbon atoms, cycloalkyl with 3 to 10 carbon atoms, heterocycloalkyl with 2 to 10 carbon atoms, cycloalkenyl with 5 to 10 carbon atoms, heterocycloalkenyl with 4 to 10 carbon atoms, alkoxy with 1 to 10 carbon atoms, alkylamine with 1 to 10 carbon atoms, alkylthio with 1 to 10 carbon atoms, aryloxy with 6 to 18 carbon atoms, arylthio with 6 to 18 carbon atoms, alkylsulfonyl with 6 to 18 carbon atoms, trialkylphosphino with 3 to 18 carbon atoms, and trialkylboron with 3 to 18 carbon atoms. In the present disclosure, a substituted functional group may have one or more of the above-mentioned substituents Rc, when two substituents Rc are attached to the same atom, these two substituents Rc may exist independently or may linked together to form a ring with the atom; and when there are two adjacent substituents Rc on the functional group, the adjacent substituents Rc may exist independently or may be fused with the functional group to form a ring.

Optionally, substituents of $Ar_1$, $Ar_2$, $Ar_3$, $Ar_4$, and $R_1$ to $R_{10}$ are the same or different, and may be each independently selected from: deuterium, a cyano, a halogen, a linear alkyl with 1 to 3 carbon atoms, a branched alkyl with 3 to 7 carbon atoms, an aryl with 6 to 18 carbon atoms, a heteroaryl with 3 to 18 carbon atoms, a cycloalkyl with 3 to 10 carbon atoms, a heterocycloalkyl with 2 to 7 carbon atoms, or an alkoxy with 1 to 7 carbon atoms; such as a methyl, an ethyl, a propyl, an isopropyl, a tert-butyl, a 2-methylbutyl, a 2-methylpentyl, a 2,3-dimethylpentyl, a cyclopropyl, a cyclobutyl, a cyclohexyl, a methylcyclopentyl, an epoxybutyl, an ethoxy, a heptoxy, a methylthio, a propylthio, a pentylthio and the like.

In the present disclosure, the number of carbon atoms of $Ar_1$, $Ar_2$, $Ar_3$, $Ar_4$, and $R_1$ to $R_{10}$ refers to the number of all carbon atoms. For example, if $Ar_1$, $Ar_2$, $Ar_3$, $Ar_4$, and $R_1$ to $R_{10}$ are selected a substituted aryl with 18 carbon atoms, the number of all carbon atoms of the aryl and substituents thereof is 18.

In the present disclosure, unless otherwise specifically defined, the term "hetero" means that a functional group includes at least one heteroatom such as B, O, N, P, Si, Se, or S, and the rest atoms are carbon and hydrogen. Unsubstituted alkyl may be saturated alkyl without any double or triple bonds.

In the present disclosure, aryl refers to any functional group or substituent derived from an aromatic ring. The aryl may refer to a monocyclic aryl group or a polycyclic aryl group. In other words, the aryl can be a monocyclic aryl group, a fused-ring aryl group, two or more monocyclic aryl groups conjugated through a carbon-carbon bond, a monocyclic aryl group or a fused-ring aryl group conjugated through a carbon-carbon bond, and two or more fused-ring aryl groups conjugated through a carbon-carbon bond. That is, two or more aromatic groups conjugated through a carbon-carbon bond can also be regarded as the aryl of the present disclosure. Wherein, the aryl does not include heteroatoms such as B, O, N, P, Si, Se, S and the like. For example, the aryl may include phenyl, naphthyl, fluorenyl, anthracenyl, phenanthryl, biphenyl, triphenyl, tetraphenyl, pentaphenyl, hexaphenyl, benzo[9,10]phenanthryl, pyrenyl, benzofluoranthenyl, chrysenyl and the like, but is not limited thereto. In the present disclosure, arylene involved refers to a divalent group obtained after one hydrogen atom is further removed from aryl.

In the present disclosure, a non-positional bond refers to a single bond " ⁝ " extending from a ring system, which means that one end of the bond can be attached to any position in the ring system through which the bond penetrates, and the other end is attached to the remaining part in the compound molecule.

For example, as shown in the following Formula (f), the naphthyl represented by the Formula (f) is attached to the remaining part in the molecule through two non-positional bonds that penetrate through the bicyclic ring, which indicates any possible attachment modes shown in Formula (f-1) to Formula (f-10).

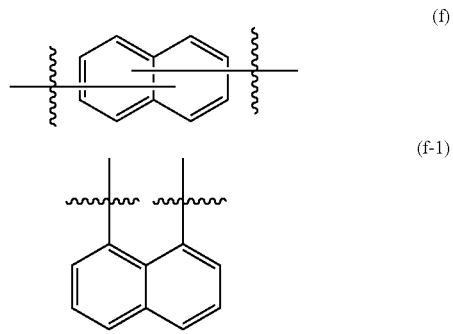

(f)

(f-1)

(f-2)
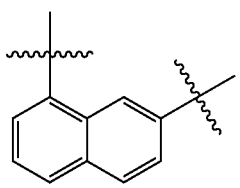
(f-3)
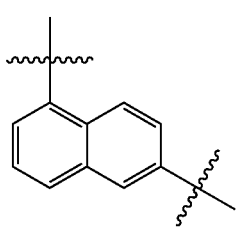
(f-4)
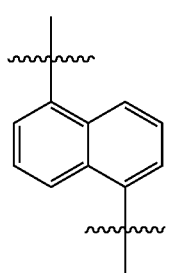
(f-5)
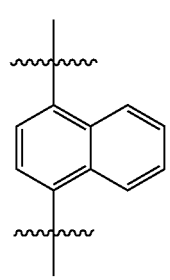
(f-6)
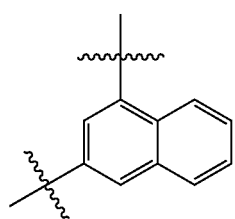
(f-7)
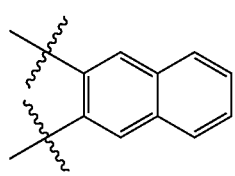
(f-8)
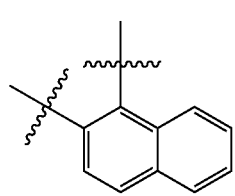
(f-9)
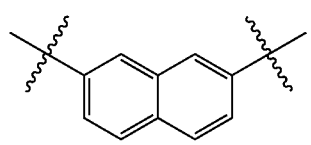
(f-10)
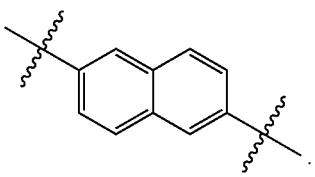
For example, as shown in the following Formula (X'), the phenanthryl represented by the Formula (X') is attached to the remaining part in the molecule through a non-positional bond extending from the middle of a benzene ring at a side, which indicates any possible attachment modes shown in Formula (X'-1) to Formula (X'-4).
(X')
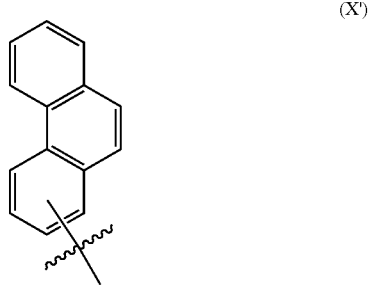
(X'-1)
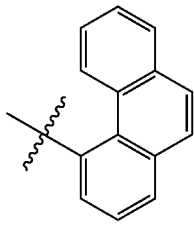
(X'-2)
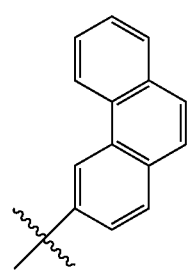

-continued (X'-3)

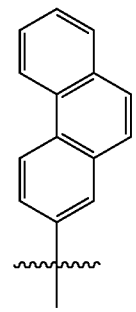

(X'-4)

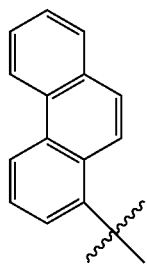

In the present disclosure, a non-positional substituent refers to a substituent linked through a single bond extending from the center of a ring system, which means that the substituent can be attached to any possible position in the ring system. For example, as shown in the following Formula (Y), the substituent R' represented by Formula (Y) is attached to a quinoline ring through a non-positional bond, which indicates any possible attachment modes shown in Formula (Y-1) to Formula (Y-7).

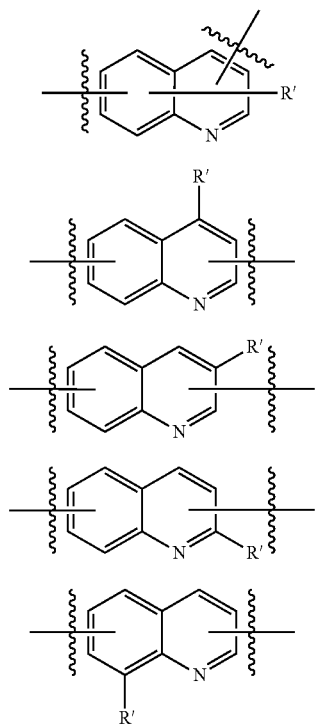

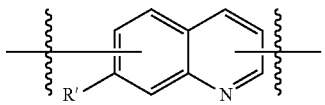

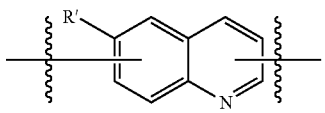

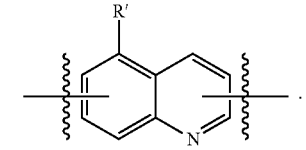

In the present disclosure, alkyl with 1 to 10 carbon atoms may be linear alkyl or branched alkyl. Specifically, alkyl with 1 to 10 carbon atoms may be linear alkyl with 1 to 10 carbon atoms or branched alkyl with 3 to 10 carbon atoms. The alkyl may have 1, 2, 3, 4, 5, 6, 7, 8, 9, or 10 carbon atoms, for example. Specific examples of alkyl with 1 to 10 carbon atoms include, but are not limited to, methyl, ethyl, n-propyl, isopropyl, n-butyl, isobutyl, tert-butyl, n-pentyl, isopentyl, neopentyl, cyclopentyl, n-hexyl, heptyl, n-octyl, 2-ethylhexyl, nonyl, decyl, or 3,7-dimethyloctyl.

In the present disclosure, alkyl with 1 to 5 carbon atoms may be linear alkyl or branched alkyl. Specifically, alkyl with 1 to 5 carbon atoms may be linear alkyl with 1 to 5 carbon atoms or branched alkyl with 3 to 5 carbon atoms. The alkyl may have 1, 2, 3, 4, or 5 carbon atoms, for example. Specific examples of alkyl with 1 to 5 carbon atoms include, but are not limited to, methyl, ethyl, n-propyl, isopropyl, n-butyl, isobutyl, tert-butyl, n-pentyl, isopentyl, neopentyl, cyclopentyl and the like.

In the present disclosure, alkyl with 1 to 3 carbon atoms may be linear alkyl or branched alkyl. Specifically, alkyl with 1 to 3 carbon atoms may be linear alkyl with 1 to 3 carbon atoms or branched alkyl with 3 carbon atoms. The alkyl may have 1, 2, or 3 carbon atoms, for example. Specific examples of alkyl with 1 to 3 carbon atoms include, but are not limited to, methyl, ethyl, n-propyl, or isopropyl.

In the present disclosure, substituted aryl refers to aryl in which one or more hydrogen atoms are substituted by other groups. For example, at least one hydrogen atom is substituted by deuterium, F, Cl, Br, I, CN, aryl, heteroaryl, hydroxyl, amino, branched alkyl, linear alkyl, cycloalkyl, alkoxy, alkylamine or other substituent. Specific examples of aryl-substituted aryl include, but are not limited to, naphthyl-substituted phenyl, phenyl-substituted naphthyl and the like. Specific examples of heteroaryl-substituted aryl include, but are not limited to, dibenzofuranyl-substituted phenyl, dibenzothienyl-substituted phenyl, pyridyl-substituted phenyl and the like. It should be interpreted that substituted aryl with 18 carbon atoms means that the total number of carbon atoms of the aryl and substituents of the aryl is 18. For example, 9,9-dimethylfluorenyl has 15 carbon atoms.

In the present disclosure, aryl to serve as a substituent is, for example, phenyl, biphenyl, naphthyl, 9,9-dimethylfluorenyl, 9,9-diphenylfluorenyl, spirobifluorenyl, anthracenyl, phenanthryl, or chrysenyl.

In the present disclosure, heteroaryl refers to a monovalent aromatic ring with at least one heteroatom on the ring or a derivative thereof. The heteroatom may be at least one of B, O, N, P, Si, Se, and S. The heteroaryl can be monocyclic heteroaryl or polycyclic heteroaryl. In other words, the heteroaryl may refer to a single aromatic ring system or multiple aromatic ring systems conjugated through carbon-carbon bonds, where any one of aromatic ring system is an aromatic monocyclic ring or an aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolinyl, quinazolinyl, quinoxalinyl, phenoxazinyl, phthalazinyl, pyridopyrimidinyl, pyridopyrazinyl, pyrazinopyrazinyl, isoquinolinyl, indolyl, carbazolyl, N-arylcarbazolyl, N-heteroarylcarbazolyl, N-alkylcarbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silylfluorenyl, dibenzofuranyl, N-arylcarbazolyl (such as N-phenylcarbazolyl), N-heteroarylcarbazolyl (such as N-pyridylcarbazolyl), N-alkylcarbazolyl (such as N-methylcarbazolyl) and the like, but is not limited thereto. Wherein, the thienyl, furyl, phenanthrolinyl and the like are heteroaryl with a single aromatic ring system; and the N-arylcarbazolyl, N-heteroarylcarbazolyl and the like are heteroaryl with multiple ring systems conjugated through carbon-carbon bonds. In the present disclosure, heteroarylene involved refers to a divalent group obtained after one hydrogen atom is further removed from heteroaryl.

In the present disclosure, substituted heteroaryl may refer to heteroaryl in which one or more hydrogen atoms are substituted by groups such as deuterium, halogen, —CN, aryl, heteroaryl, trialkylsilyl, alkyl, cycloalkyl, alkoxy, alkylthio and the like. Specific examples of aryl-substituted heteroaryl include, but are not limited to, phenyl-substituted dibenzofuranyl, phenyl-substituted dibenzothienyl, phenyl-substituted pyridyl and the like. It should be understood that the number of carbon atoms of substituted heteroaryl refers to the total number of carbon atoms of the heteroaryl and substituents of the heteroaryl.

In the present disclosure, heteroaryl to serve as a substituent is, for example, pyridyl, pyrimidinyl, carbazolyl, dibenzofuranyl, or dibenzothienyl.

Optionally, substituents of $Ar_1$, $Ar_2$, $Ar_3$, $Ar_4$, and $R_1$ to $R_{10}$ may be the same or different, and may be respectively independently selected from: deuterium, a cyano, a halogen, a linear alkyl with 1 to 3 carbon atoms, a branched alkyl with 3 to 5 carbon atoms, an aryl with 6 to 18 carbon atoms, a heteroaryl with 3 to 12 carbon atoms, or a cycloalkyl with 3 to 10 carbon atoms.

In the present disclosure, the halogen can be, for example, fluorine, chlorine, bromine, or iodine.

Optionally, $R_1$ to $R_{10}$ may be the same or different, and may be respectively independently selected from: hydrogen, deuterium, a fluorine, a cyano, a substituted or unsubstituted silyl, a substituted or unsubstituted alkyl with 1 to 5 carbon atoms, a substituted or unsubstituted aryl with 6 to 18 carbon atoms, a substituted or unsubstituted heteroaryl with 3 to 12 carbon atoms, or a substituted or unsubstituted cycloalkyl with 1 to 10 carbon atoms.

Optionally, $R_2$ and $R_6$ are not hydrogen, and $R_1$, $R_3$, $R_4$, $R_5$, $R_7$, $R_8$, $R_9$, and $R_{10}$ are all be hydrogen.

Optionally, $Ar_1$, $Ar_2$, $Ar_3$, and $Ar_4$ are the same or different, and are respectively independently selected from: a substituted or unsubstituted aryl with 6 to 25 carbon atoms or a substituted or unsubstituted heteroaryl with 5 to 20 carbon atoms.

Optionally, $Ar_1$, $Ar_2$, $Ar_3$, and $Ar_4$ are respectively independently selected from the group consisting of the following structures (i-1) to (i-9):

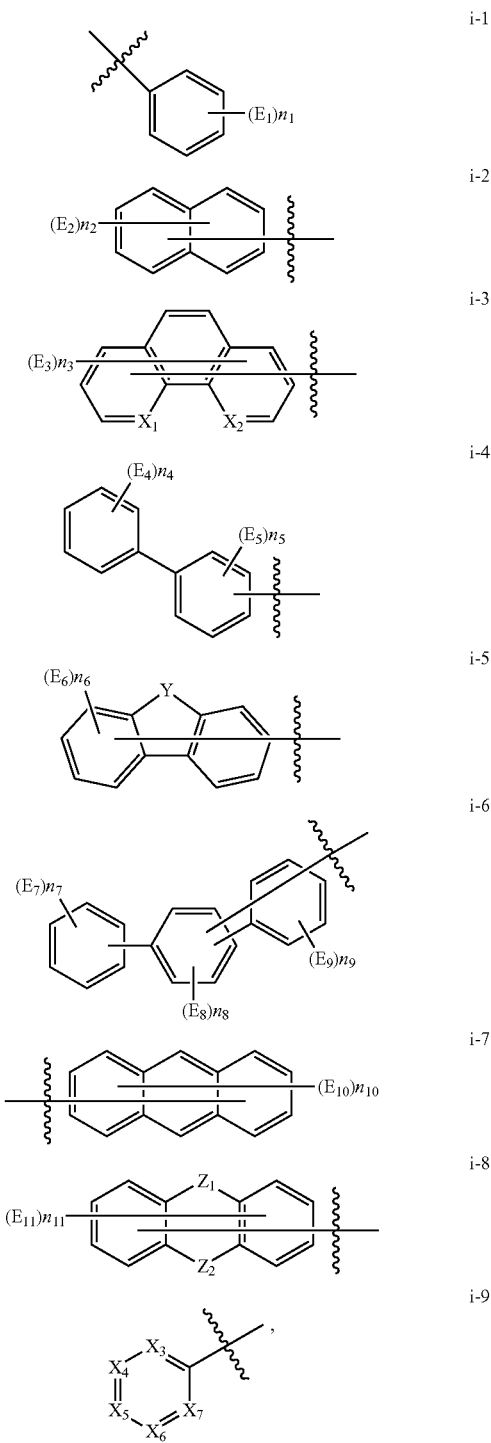

wherein, $n_1$, $n_4$, $n_7$, and $n_9$ are the same or different, and are respectively independently selected from: 1, 2, 3, 4, or 5;

$n_2$, $n_3$, and $n_{11}$ are the same or different, and are respectively independently selected from: 1, 2, 3, 4, 5, 6, or 7;

$n_5$, $n_6$, and $n_8$ are the same or different, and are respectively independently selected from: 1, 2, 3, or 4;

$n_{10}$ is selected from: 1, 2, 3, 4, 5, 6, 7, 8, or 9;

$X_1$ and $X_2$ are the same or different, and are respectively independently selected from: C or N, where when $X_1$ and $X_2$ are selected from C, it means that $X_1$ and $X_2$ are CH;

Y is selected from: O, S, $Si(E_{12}E_{13})$, $C(E_{14}E_{15})$, $N(E_{16})$, or Se;

$Z_1$ and $Z_2$ are the same or different, and are respectively independently selected from: O, S, $N(E_{17})$, or $C(E_{18}E_{19})$;

$E_1$, $E_4$, and $E_5$ are the same or different, and are respectively independently selected from: deuterium, halogen, a cyano, an alkyl with 1 to 5 carbon atoms, a heteroaryl with 3 to 18 carbon atoms, or a cycloalkyl with 3 to 10 carbon atoms;

$E_2$, $E_3$, and $E_6$ to $E_{19}$ are the same or different, and are respectively independently selected from: hydrogen, deuterium, a halogen, a cyano, an alkyl with 1 to 5 carbon atoms, an aryl with 6 to 18 carbon atoms, a heteroaryl with 3 to 18 carbon atoms, or a cycloalkyl with 3 to 10 carbon atoms; or $E_{12}$ and $E_{13}$ can be linked to form a ring, or $E_{14}$ and $E_{15}$ can be linked to form a ring, or $E_{18}$ and $E_{19}$ can be linked to form a ring;

$X_3$ to $X_7$ are the same or different, and are respectively independently selected from: C(R') or N; at least one of $X_3$ to $X_7$ is N; R' groups of $X_3$ to $X_7$ are the same or different, and are each independently selected from: an alkyl with 1 to 5 carbon atoms, an aryl with 6 to 18 carbon atoms, a heteroaryl with 3 to 18 carbon atoms, or a cycloalkyl with 3 to 10 carbon atoms; or adjacent R' groups can be linked to form a ring.

In the present disclosure, when $n_1$ is greater than or equal to 2, $E_1$ groups are the same or different; when $n_2$ is greater than or equal to 2, $E_2$ groups are the same or different; when $n_3$ is greater than or equal to 2, $E_3$ groups are the same or different; when $n_4$ is greater than or equal to 2, $E_4$ groups are the same or different; when $n_5$ is greater than or equal to 2, $E_5$ groups are the same or different; when $n_6$ is greater than or equal to 2, $E_6$ groups are the same or different; when $n_7$ is greater than or equal to 2, $E_7$ groups are the same or different; when $n_8$ is greater than or equal to 2, $E_8$ groups are the same or different; when $n_9$ is greater than or equal to 2, $E_9$ groups are the same or different; when $n_{10}$ is greater than or equal to 2, $E_{10}$ groups are the same or different; and when $n_{11}$ is greater than or equal to 2, $E_{11}$ groups are the same or different.

In the present disclosure, Formula

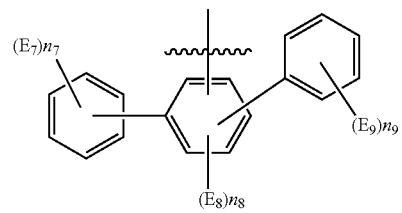

i-6 refers to the two structures of both Formula

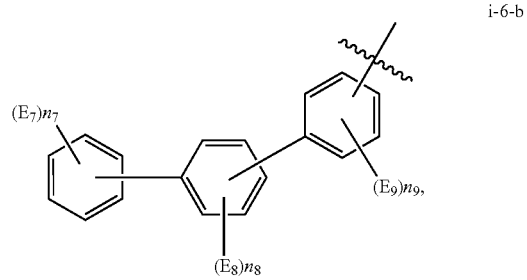

i-6-a and Formula i-6-b where, in Formula i-6-a, $n_7$ and $n_9$ are selected from: 1, 2, 3, 4, or 5, and $n_8$ is selected from: 1, 2, or 3; and in Formula i-6-b, $n_7$ is selected from: 1, 2, 3, 4, or 5, and $n_8$ and $n_9$ are selected from: 1, 2, 3, or 4.

In the present disclosure, when $n_1$ to $n_{11}$ is selected from 0, the benzene ring is not substituted.

The phrase "adjacent R' groups can be linked to form a ring" means that $X_3$ and $X_4$ form a ring, or $X_4$ and $X_5$ form a ring, or $X_5$ and $X_6$ form a ring, or $X_6$ and $X_7$ form a ring, or $X_3$ and $X_4$ form a ring, or $X_5$ and $X_6$ form a ring.

In the present disclosure, the phrase "A and B can be linked to form a ring" means that A and B are independent of each other and are not linked; or A and B are linked to form a ring. For example, the phrase "$E_{12}$ and $E_{13}$ can be linked to form a ring" means that $E_{12}$ and $E_{13}$ are independent of each other and are not linked, or $E_{12}$ and $E_{13}$ are linked to form a ring; the phrase "$E_{14}$ and $E_{15}$ can be linked to form a ring" means that $E_{14}$ and $E_{15}$ are independent of each other and are not linked, or $E_{14}$ and $E_{15}$ are linked to form a ring; and the phrase "$E_{18}$ and $E_{19}$ can be linked to form a ring" means that $E_{18}$ and $E_{19}$ are independent of each other and are not linked, or $E_{18}$ and $E_{19}$ are linked to form a ring.

For example, the phrase "$X_3$ and $X_4$ can be linked to form a ring" means that R' of $X_3$ and R' of $X_4$ are independent of each other and are not linked, or R' of $X_3$, R' of $X_4$, and atoms attached to R' are linked to form a ring.

In the present disclosure, the ring refers to a saturated or unsaturated ring, such as

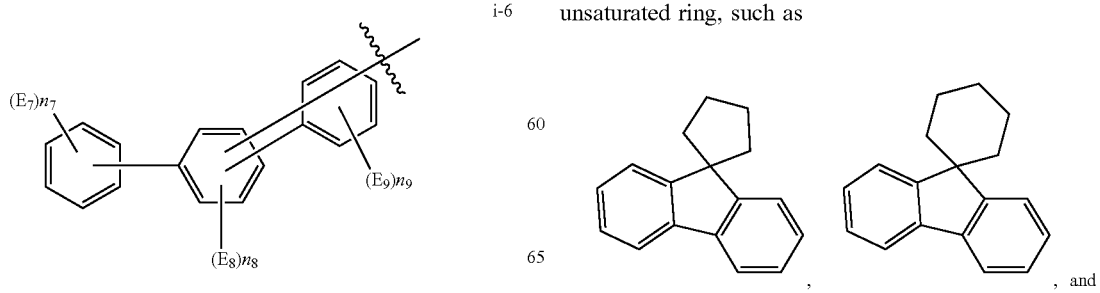

, and

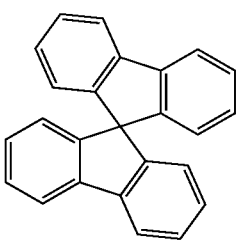
which is not limited thereto.
Specifically, $Ar_1$, $Ar_2$, $Ar_3$, and $Ar_4$ are respectively independently selected from the group consisting of the following groups:
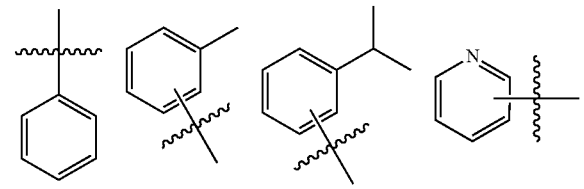
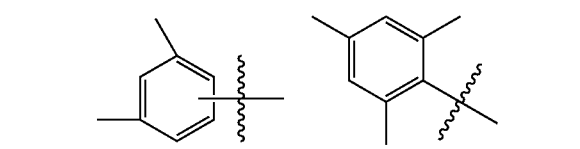
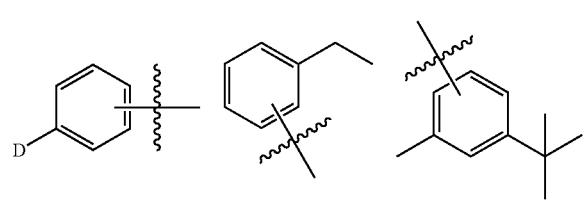
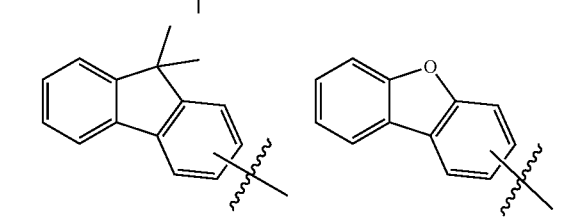
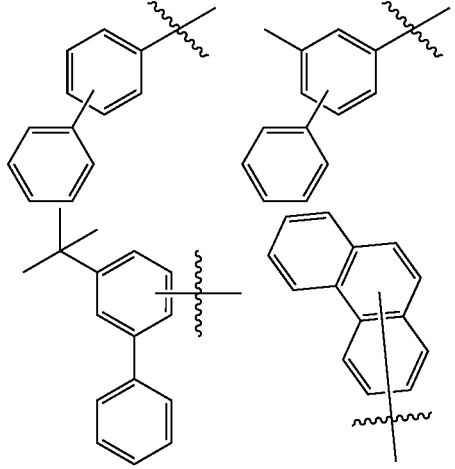
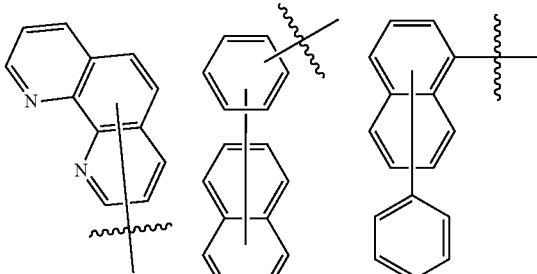
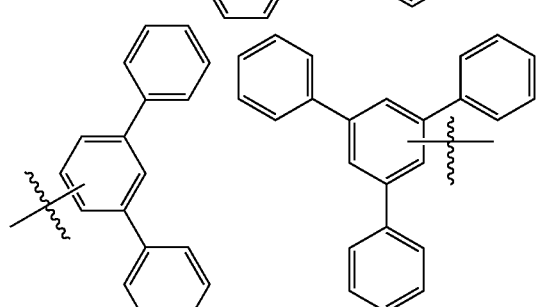
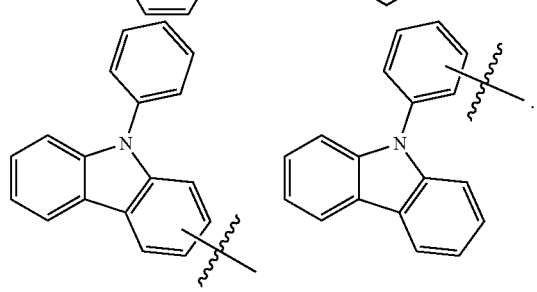
Optionally, $Ar_1$, $Ar_2$, $Ar_3$, and $Ar_4$ are respectively independently selected from the group consisting of the following groups:
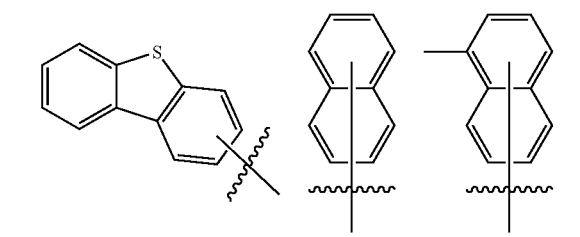
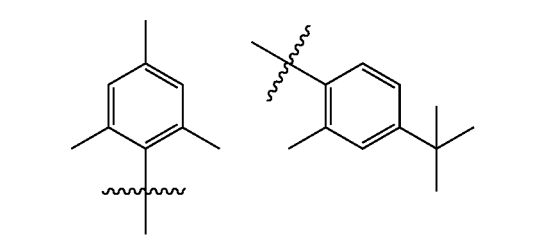

-continued
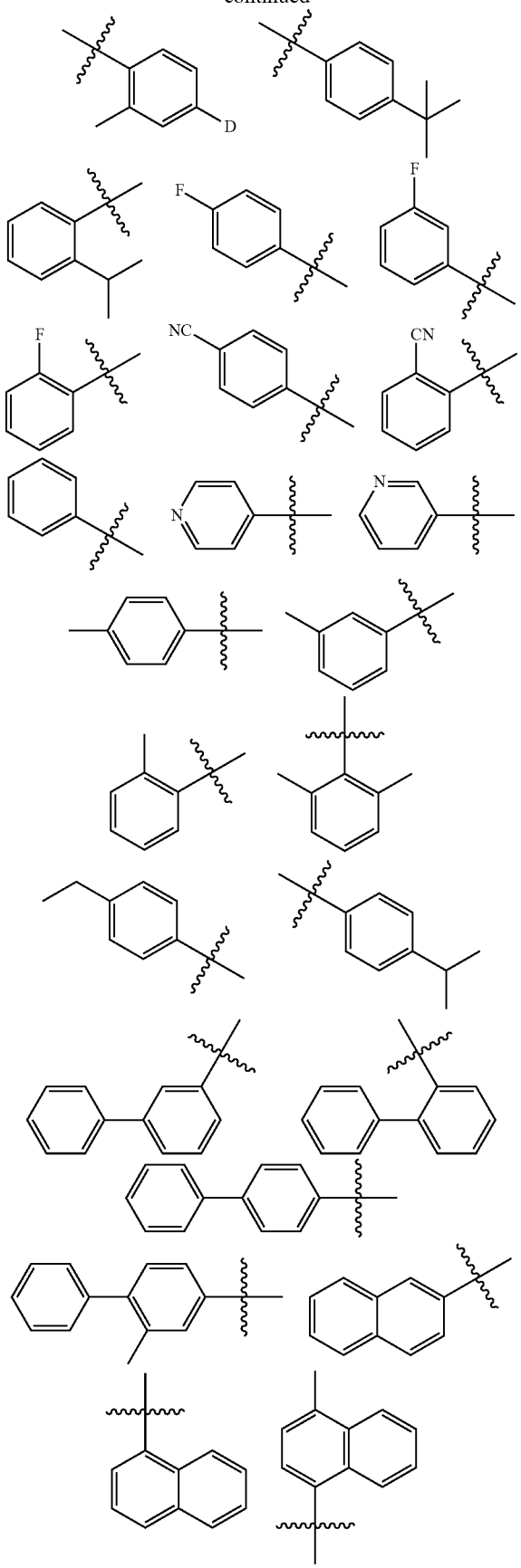
-continued
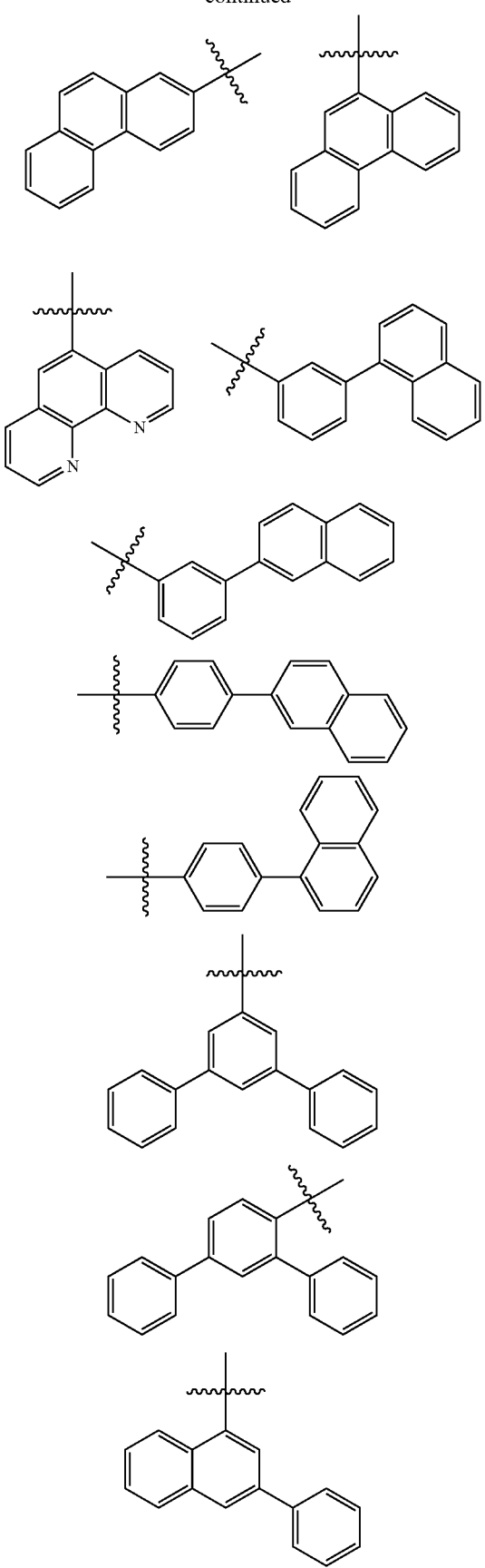

-continued

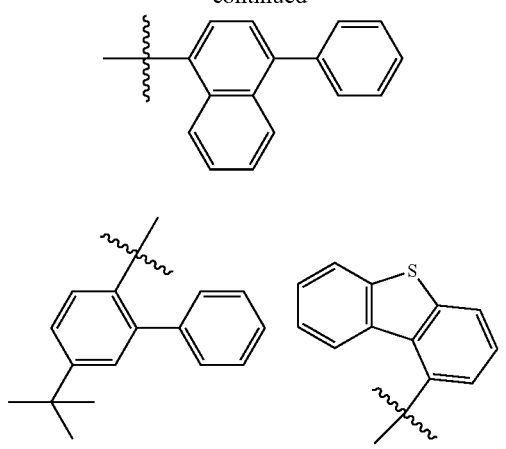

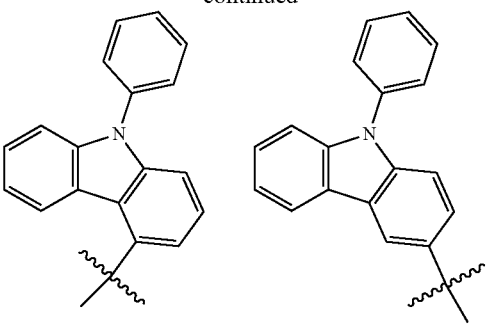

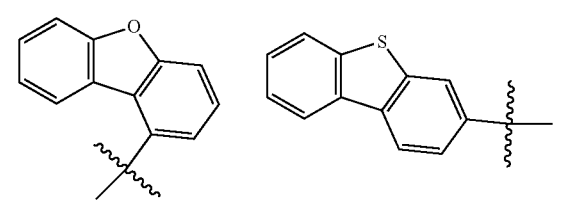

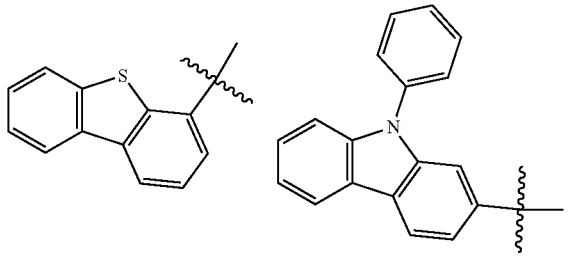

Optionally, $Ar_1$, $Ar_2$, $Ar_3$, and $Ar_4$ are respectively independently selected from substituted or unsubstituted following groups: phenyl, naphthyl, biphenyl, triphenyl, phenanthryl, anthracenyl, 9,9-spirobifluorenyl, 9,9-dimethylfluorenyl, pyridyl, carbazolyl, pyrimidinyl, 1,10-phenanthrolinyl, pyridazinyl, triazinyl, quinolinyl, quinazolinyl, phenylpyridyl, quinoxalinyl, pyrenyl, N-phenylcarbazolyl, dibenzofuranyl, dibenzothienyl, or spiro(adamantyl-fluorenyl);

and substituents of the groups are selected from: deuterium, fluorine, chlorine, cyano, trimethylsilyl, methyl, ethyl, isopropyl, tert-butyl, phenyl, naphthyl, pyridyl, dibenzofuranyl, carbazolyl, or dibenzothienyl; and when there are a plurality of substituents, the plurality of substituents may be the same or different.

Optionally, the nitrogen-containing compound may be selected from the group consisting of the following compounds:
1
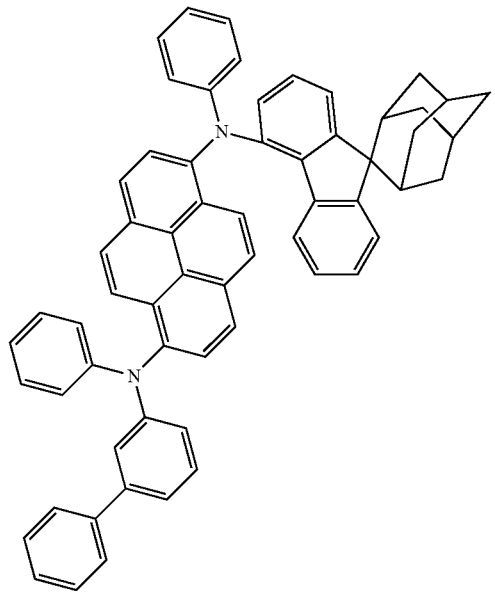
2
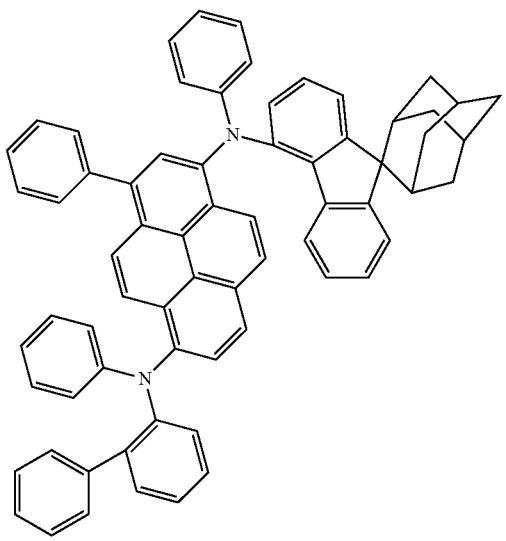
3
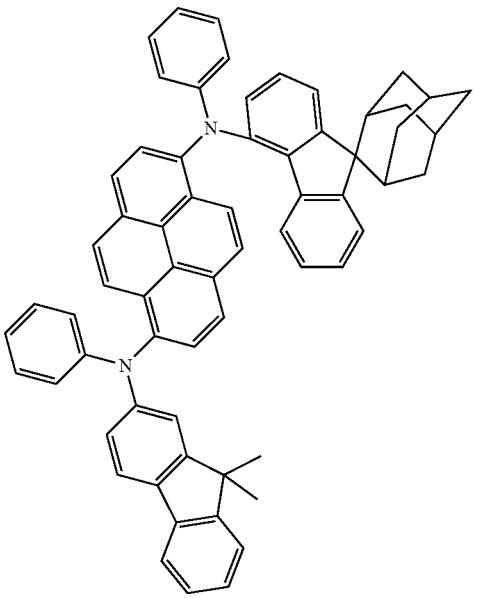
4
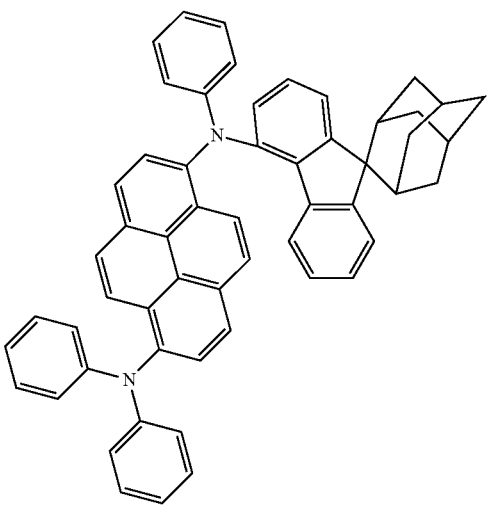
5

6
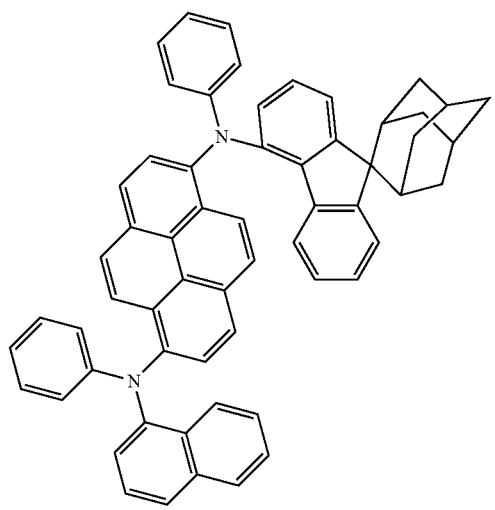
7
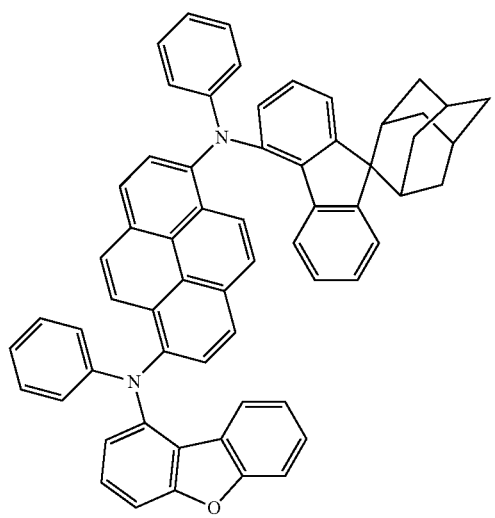
8
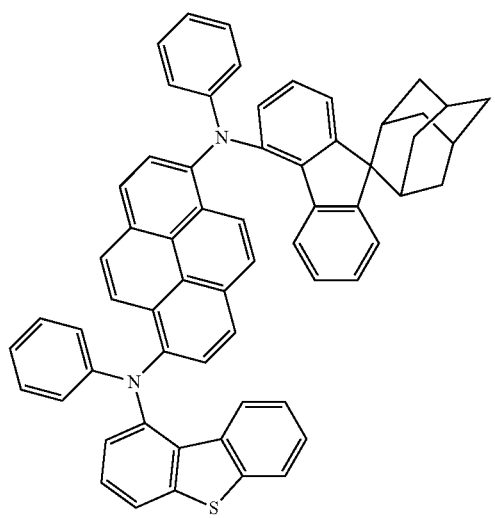
9
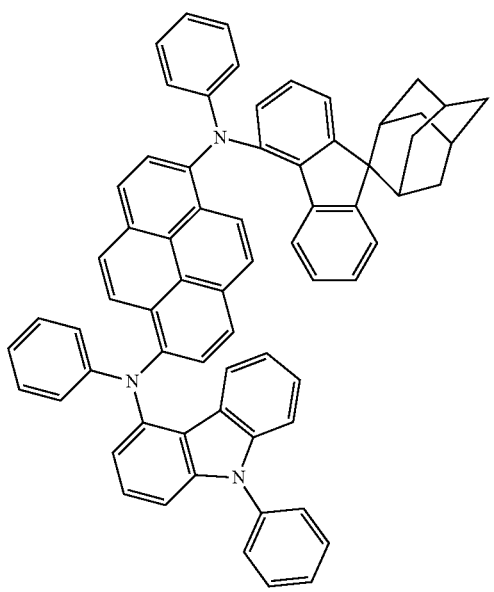
10
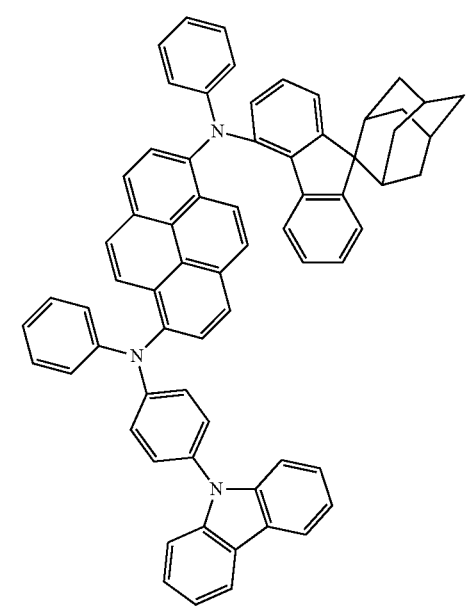

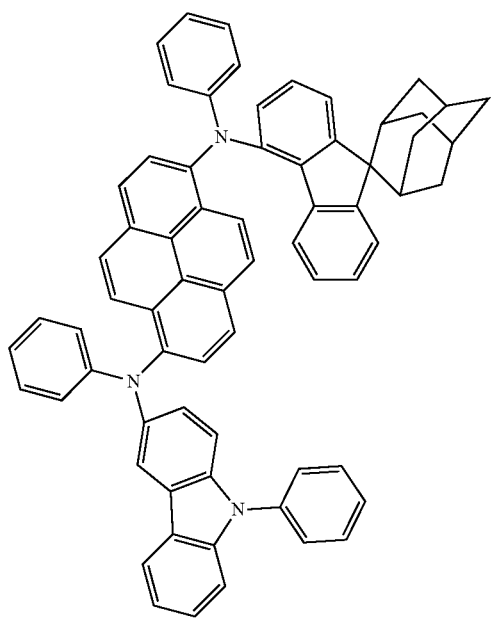
11
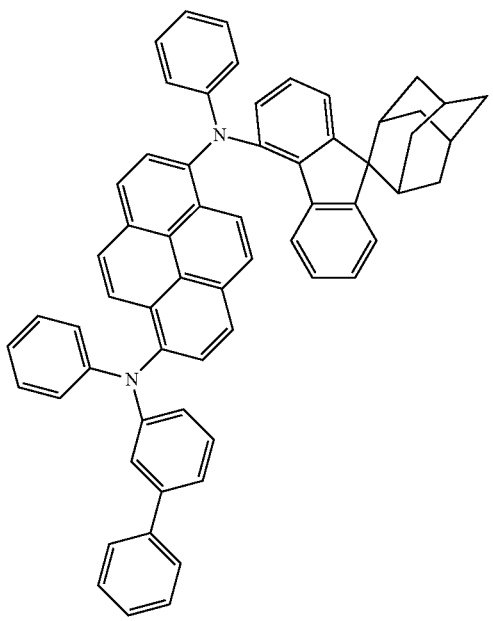
13
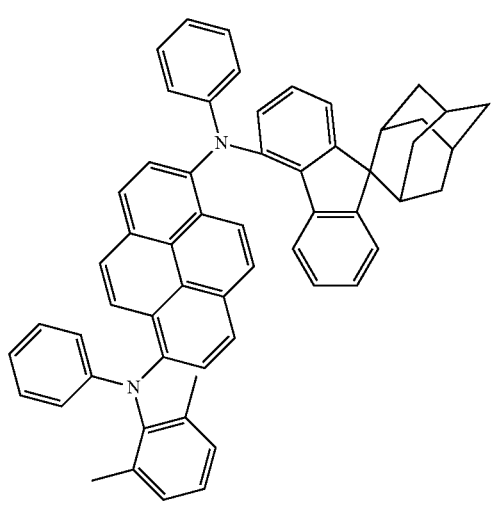
12
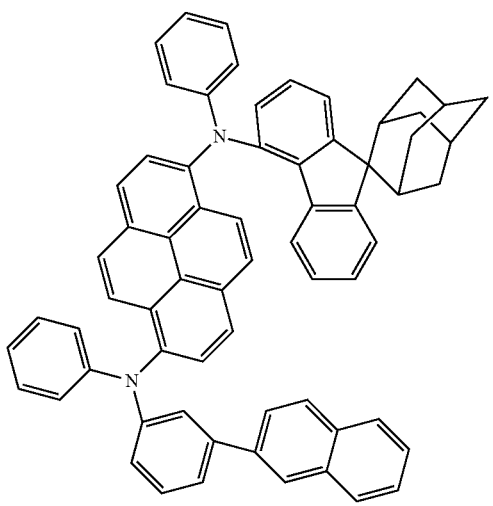
14
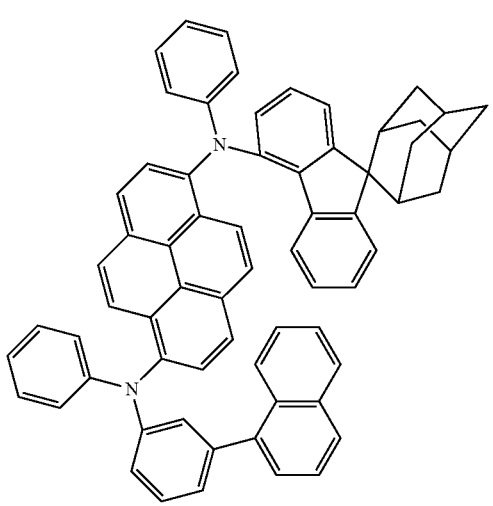
15

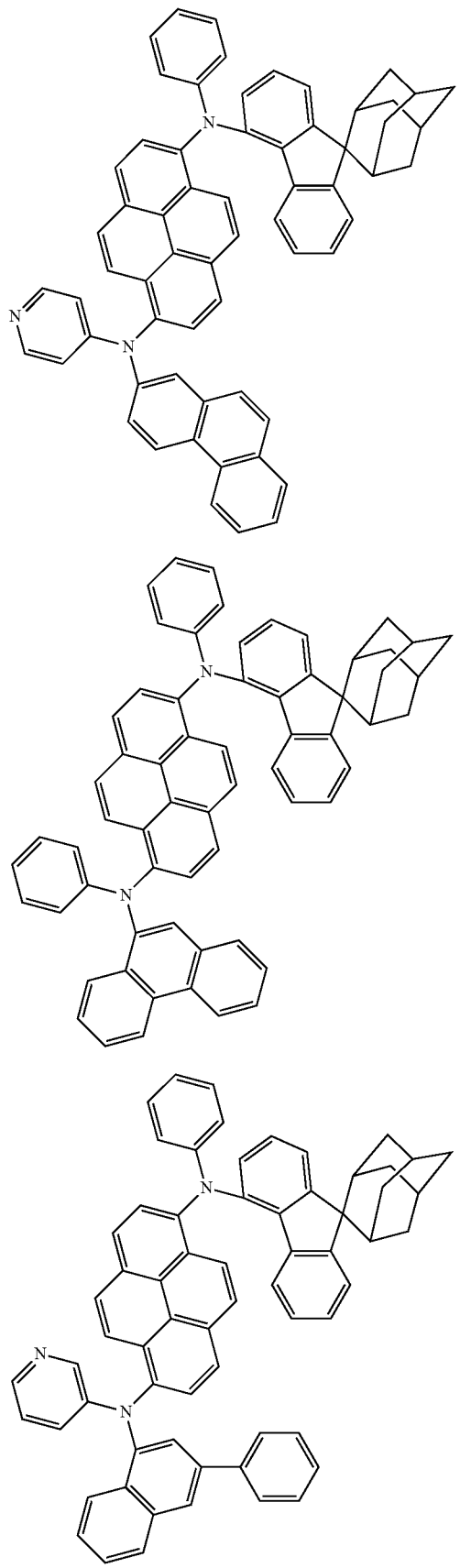

21
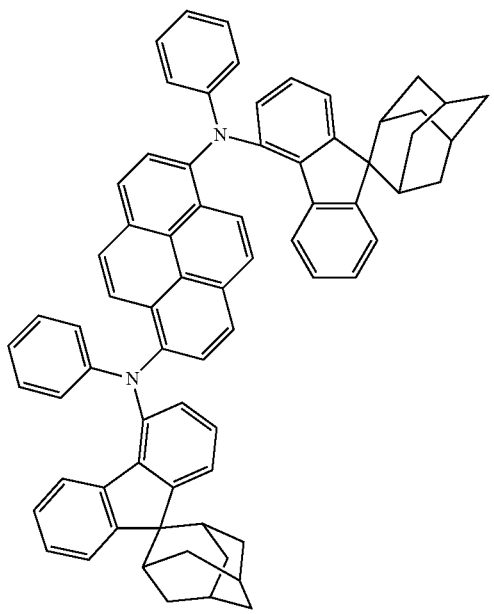
22
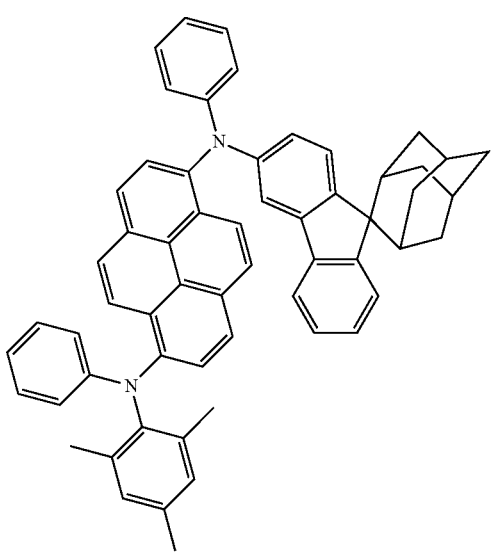
23
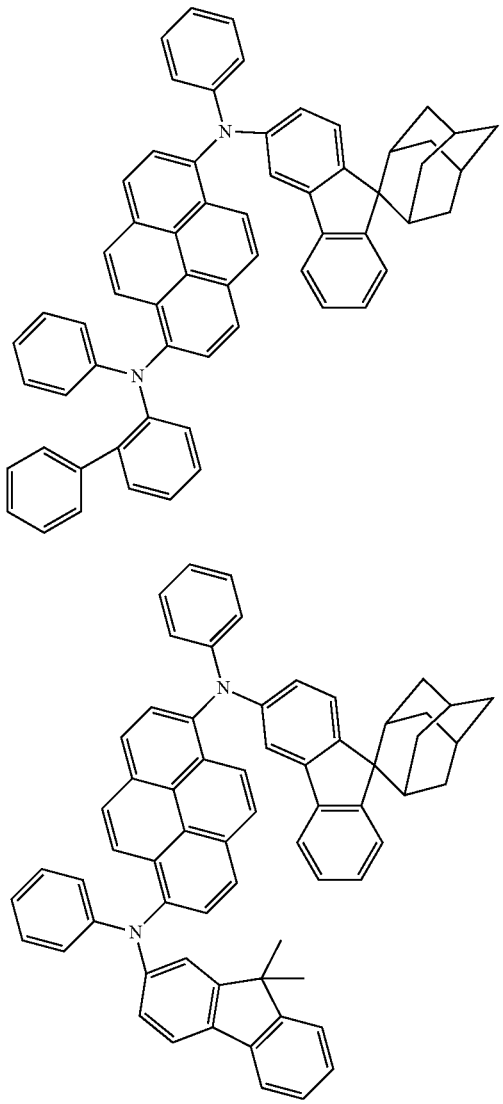
24
25
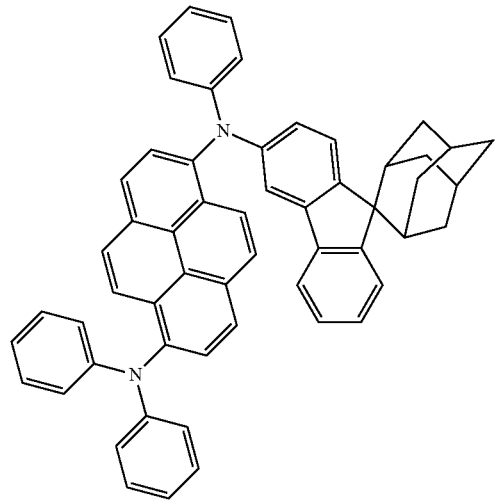

26
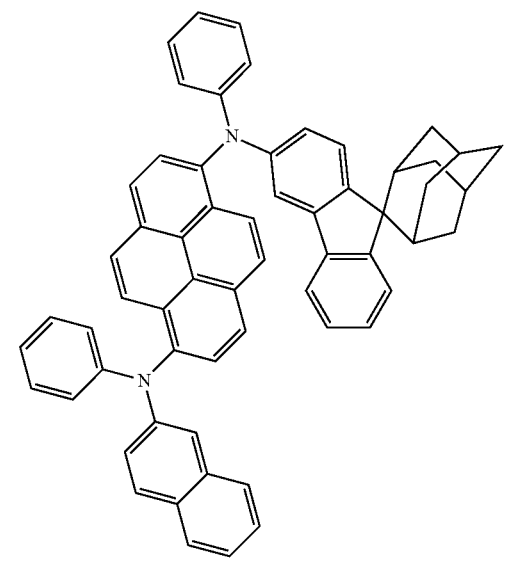
27
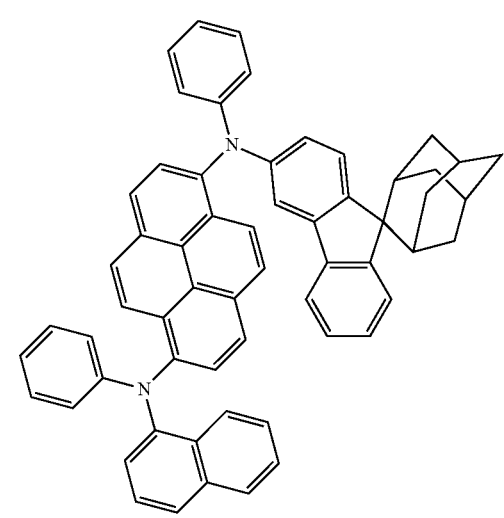
28
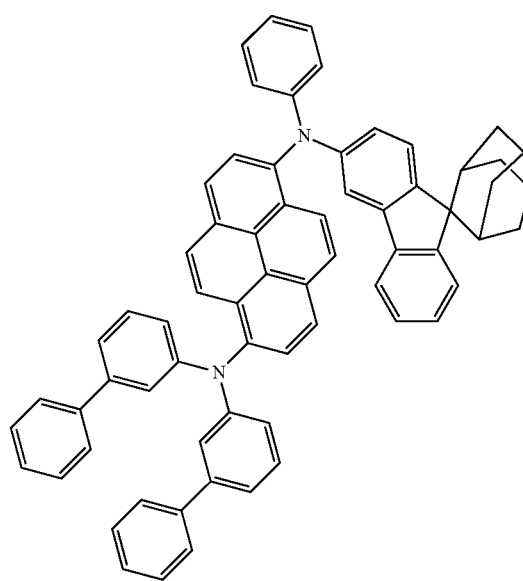
29
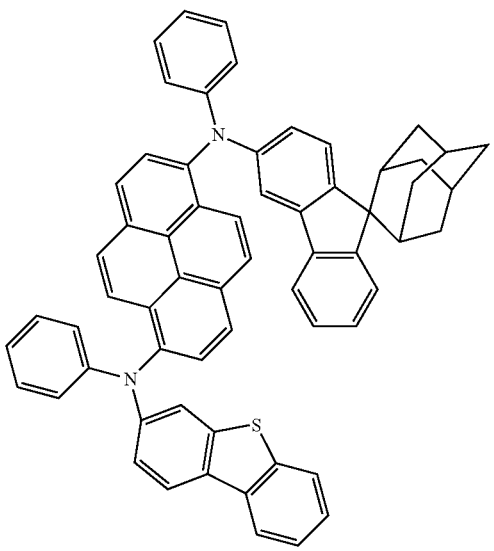
30
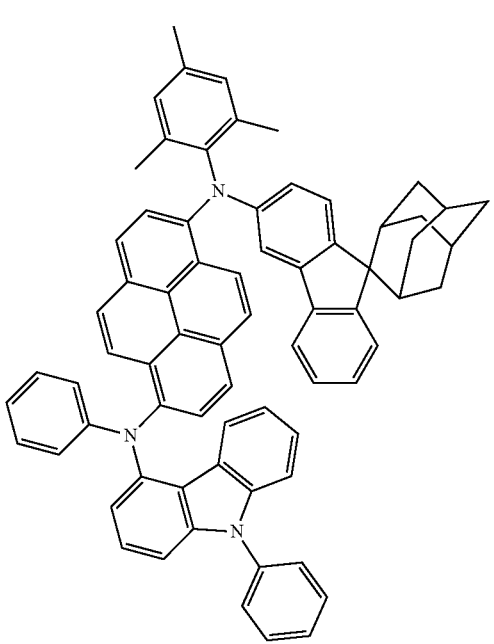

31
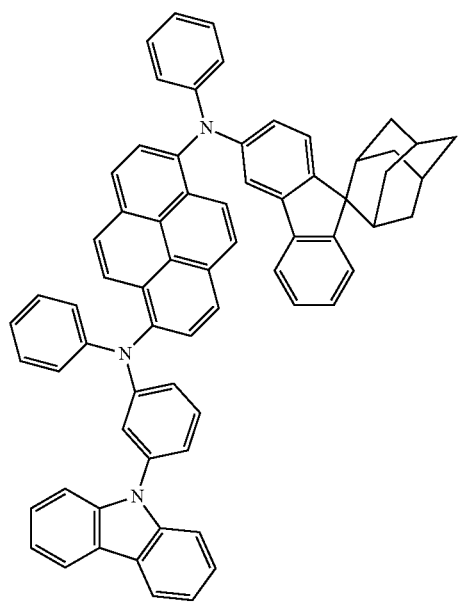
32
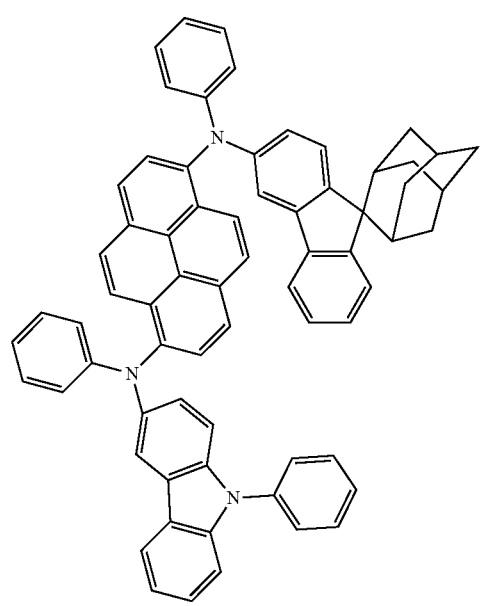
33
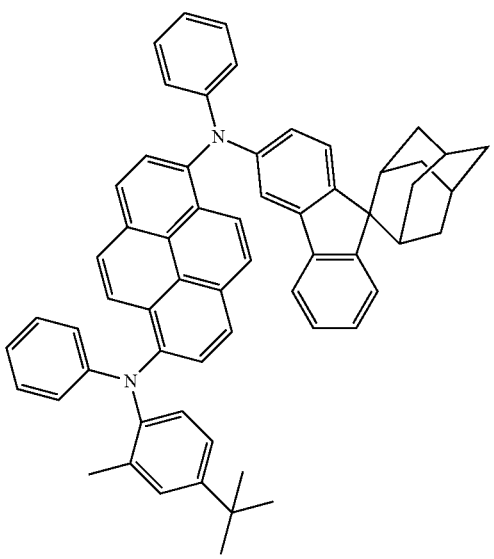
34
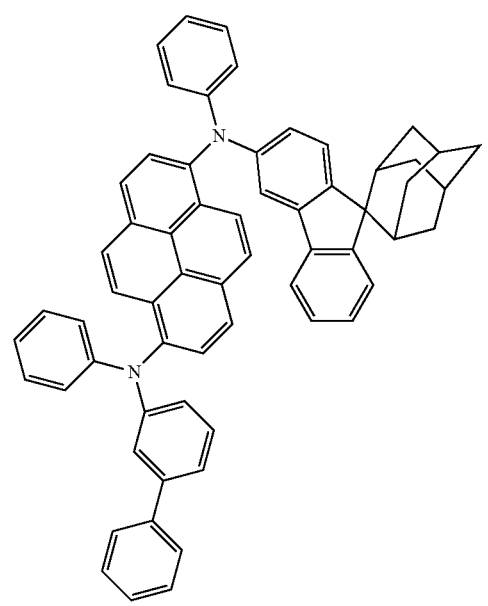
35
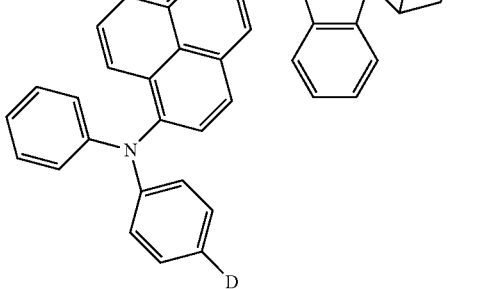

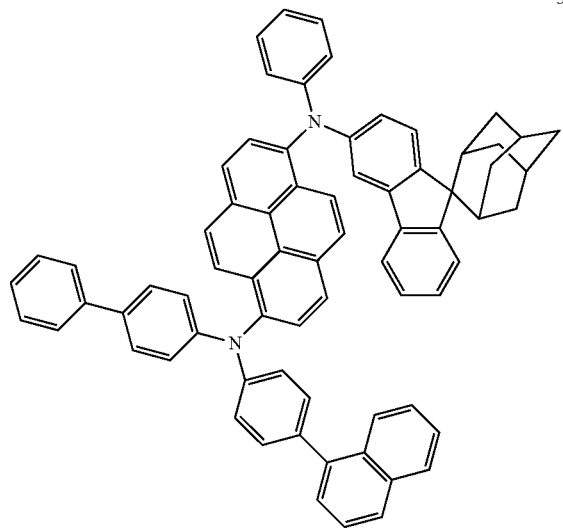
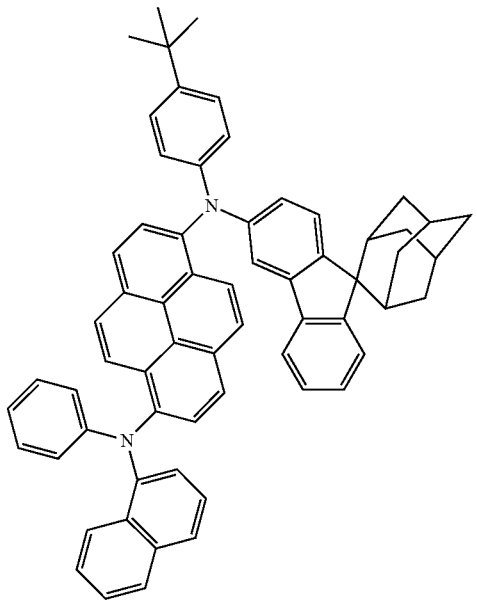

39
-continued
41
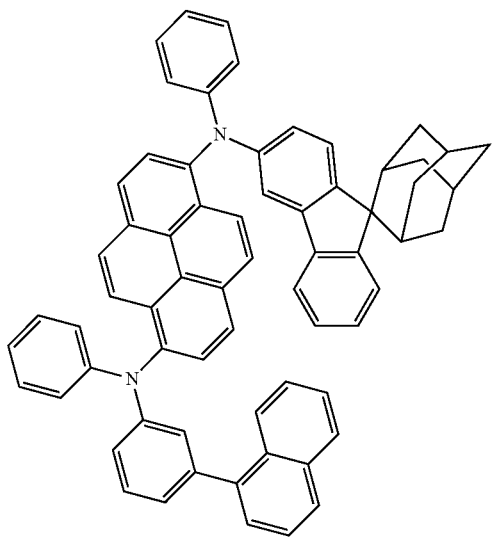
43
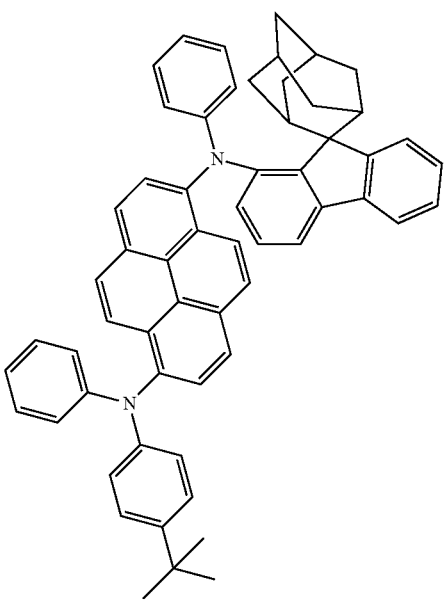
40
-continued
42
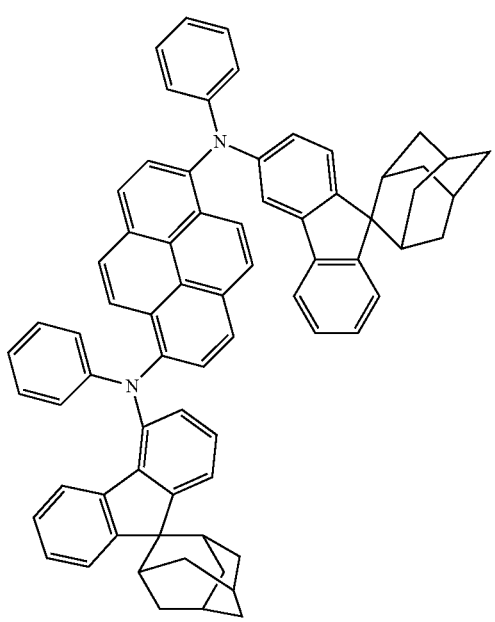
44
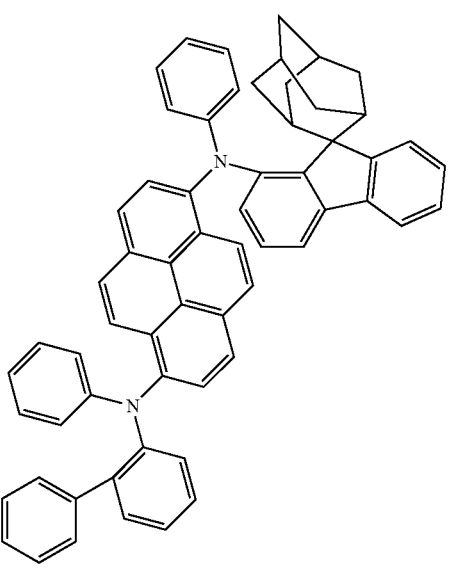

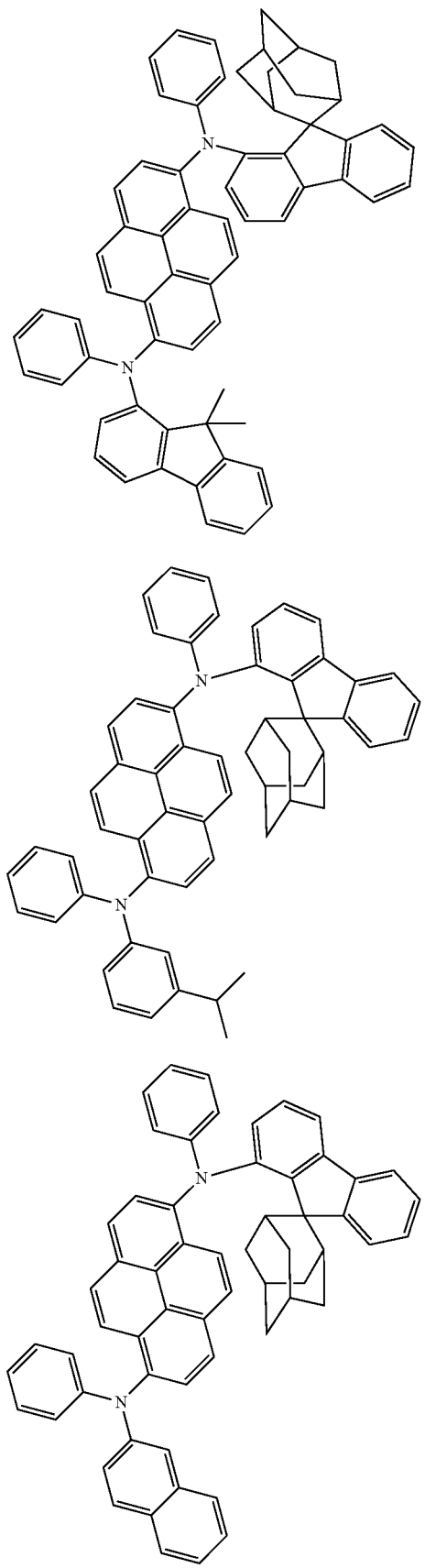
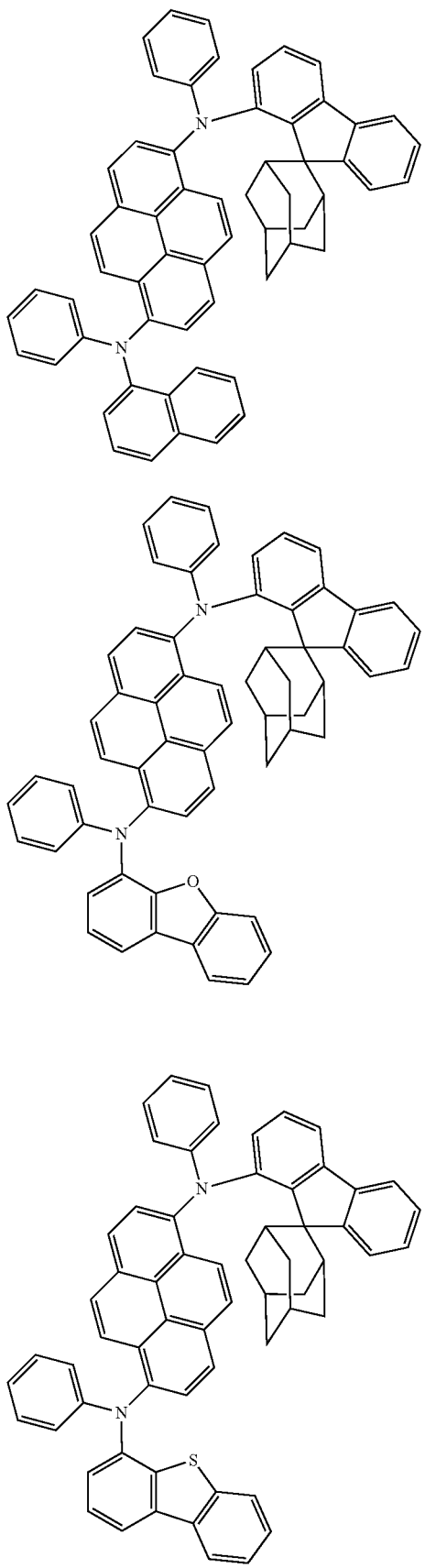

51
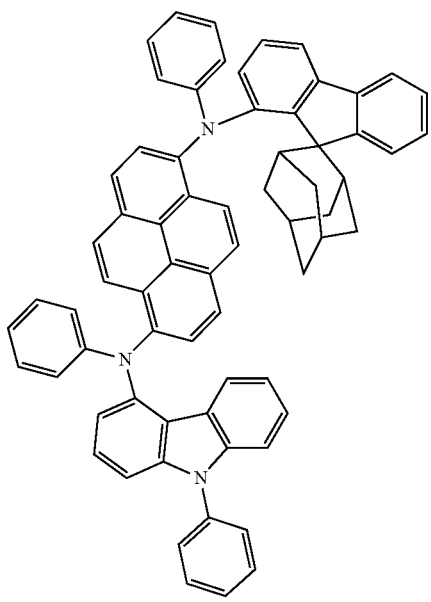
52
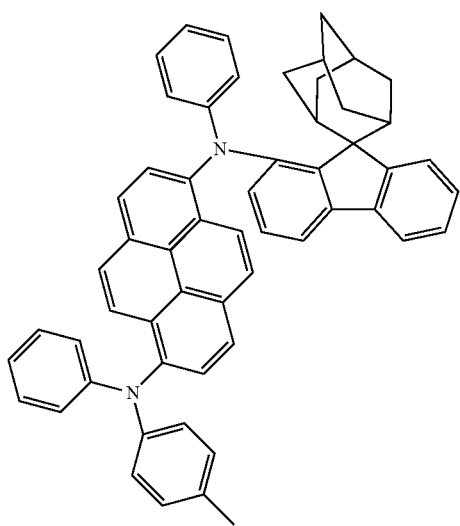
53
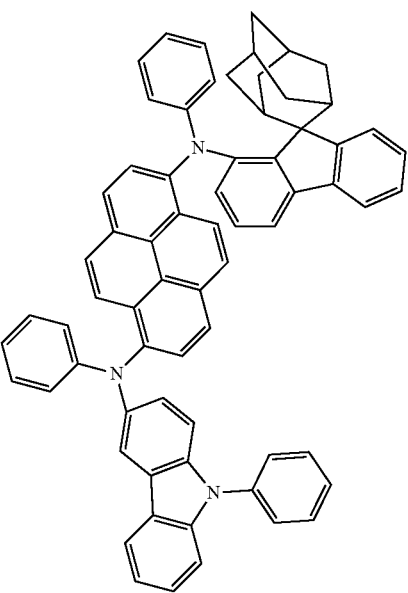
54
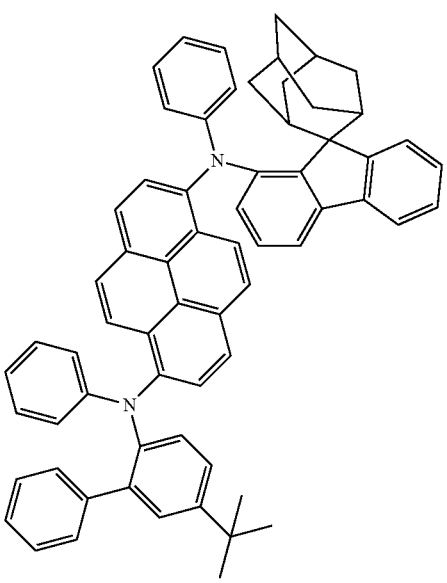

55
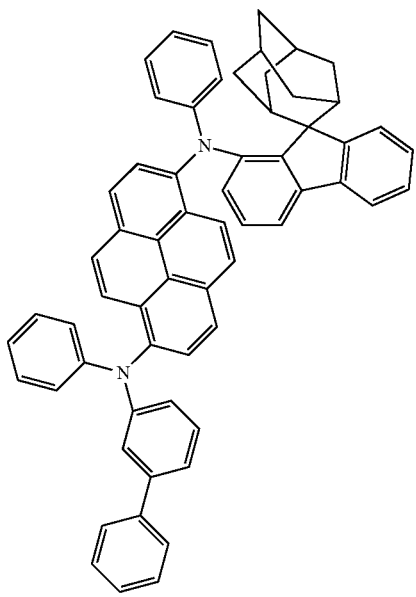
56
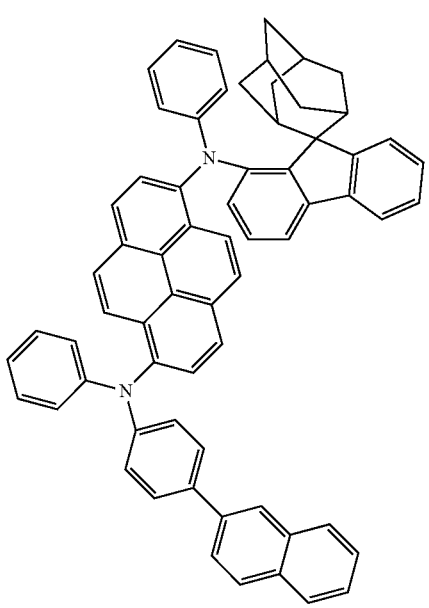
57
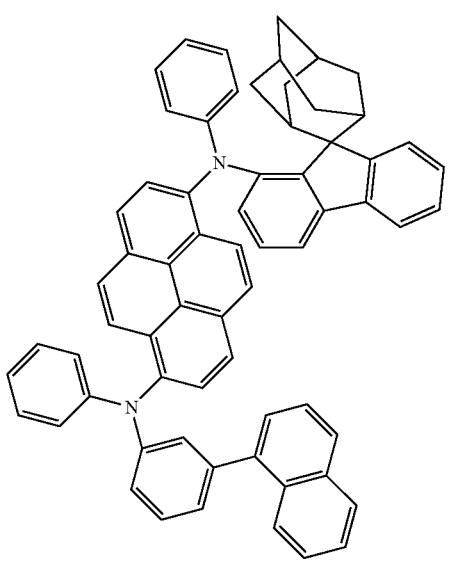
58
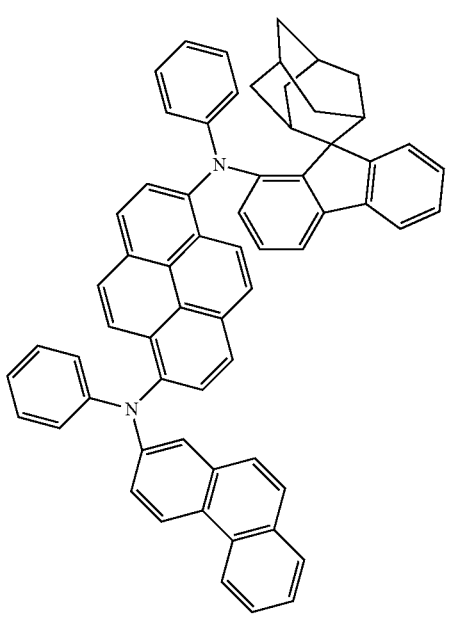

59
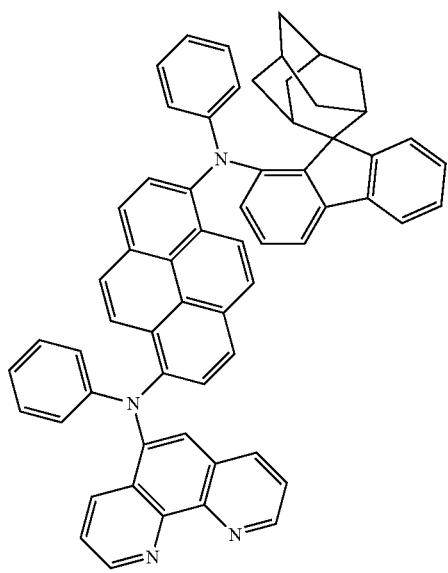
61
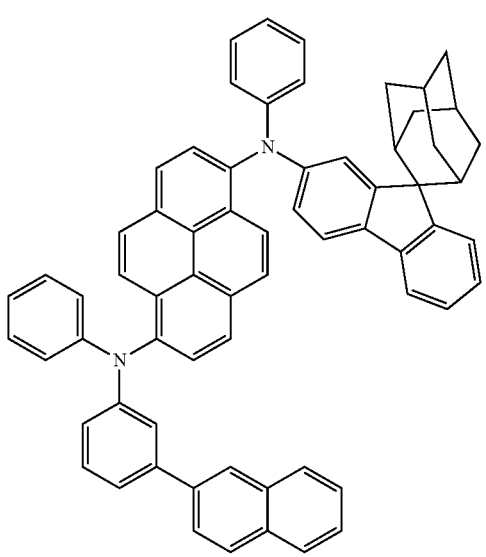
60
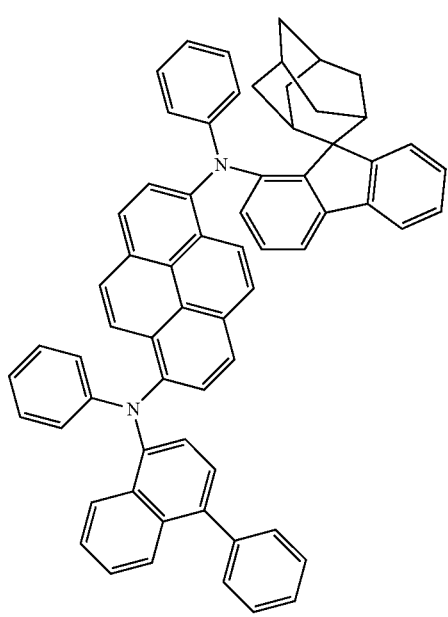
62
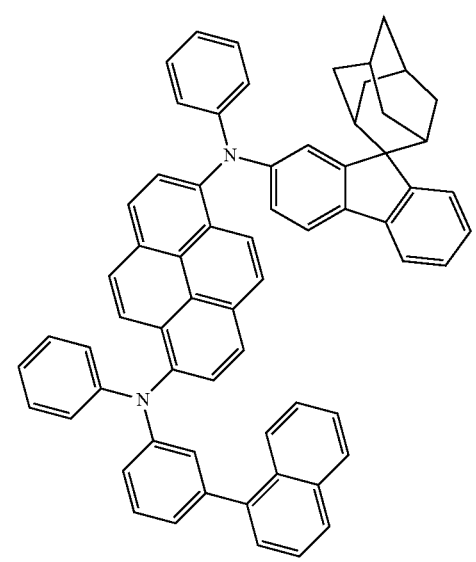

63
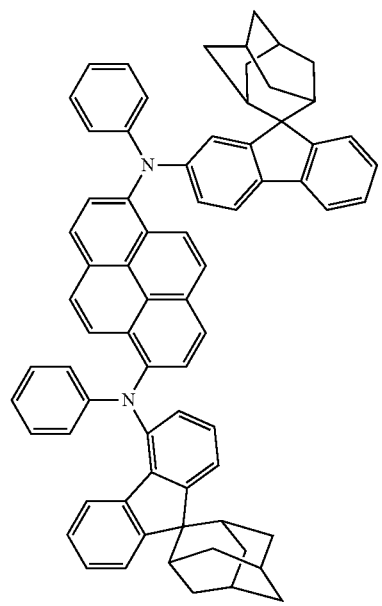
64
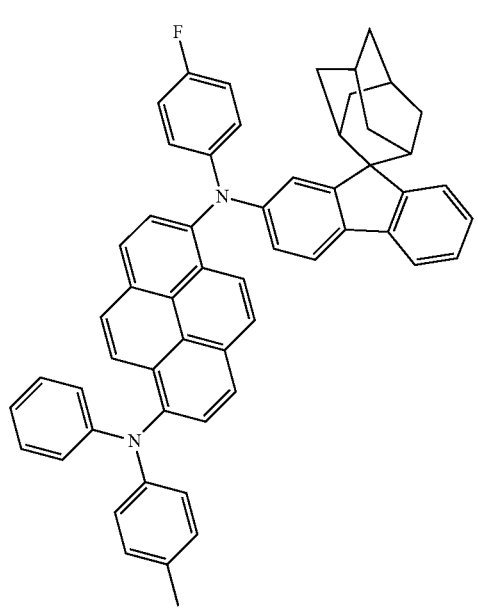
65
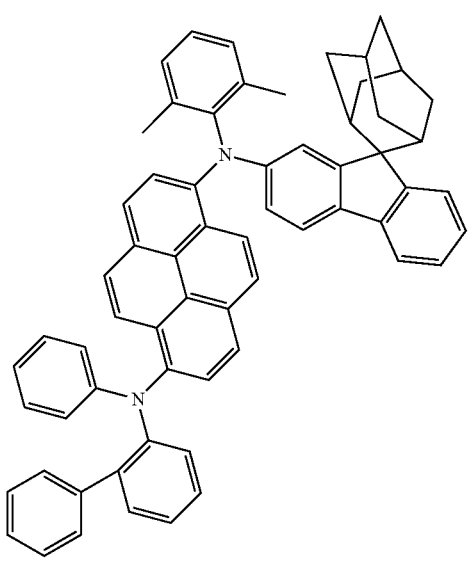
66
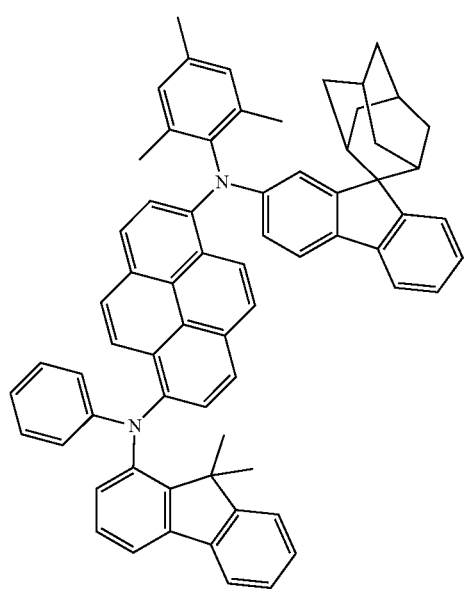

67
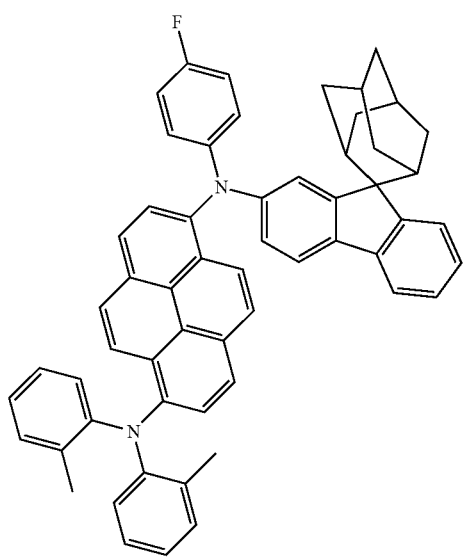
68
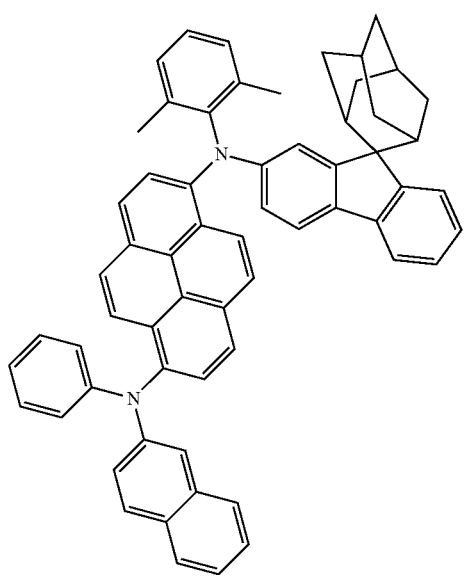
69
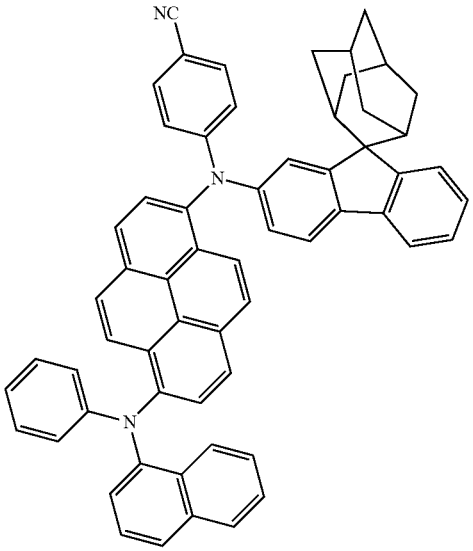
70
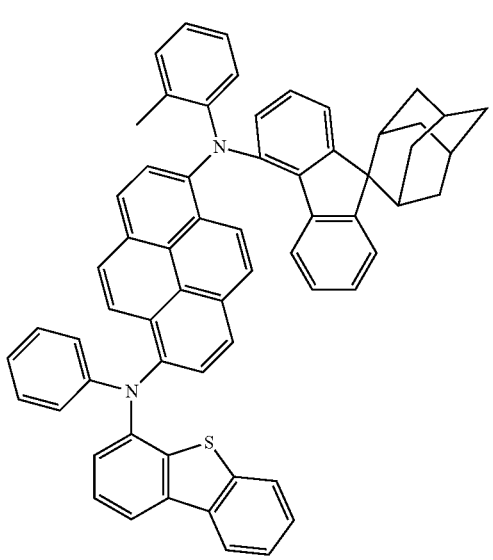
71

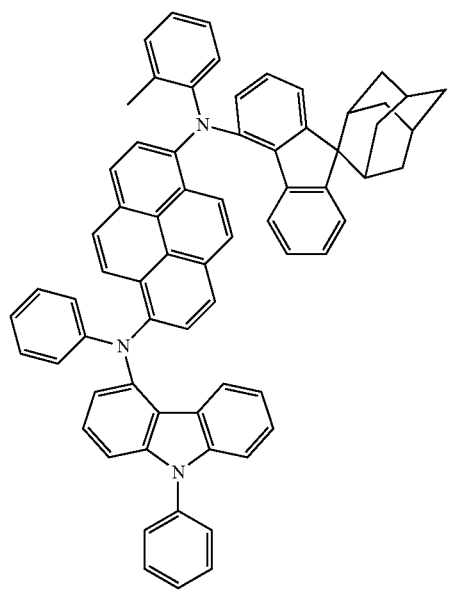
72
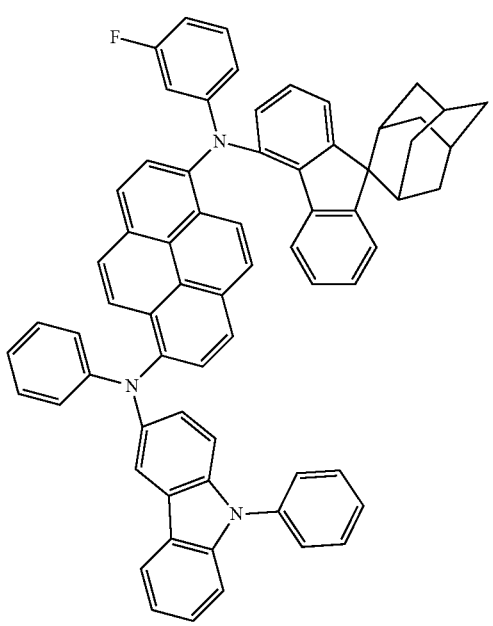
74
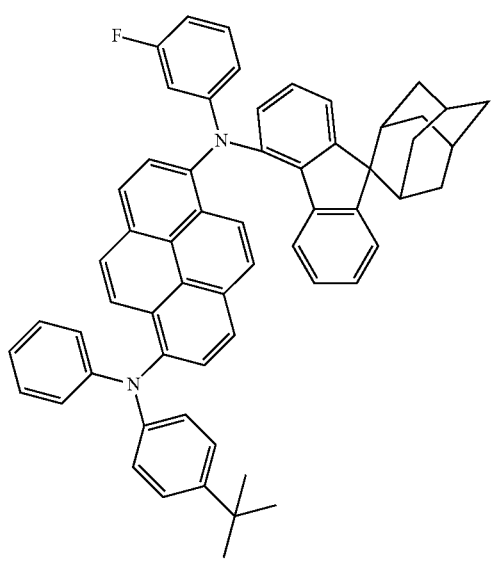
73
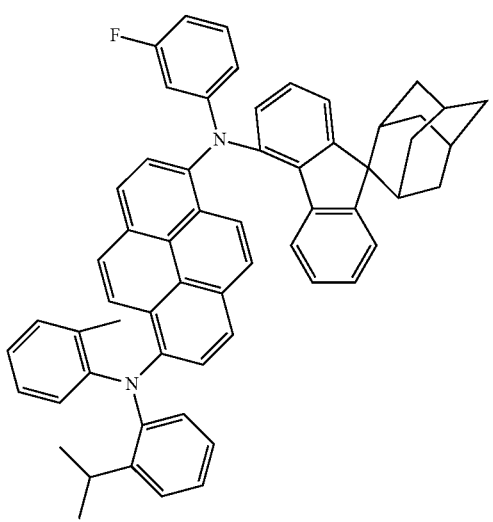
75

55
-continued
76
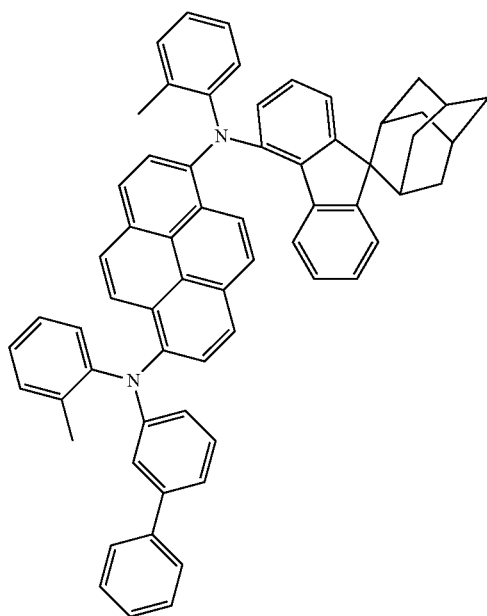
56
-continued
78
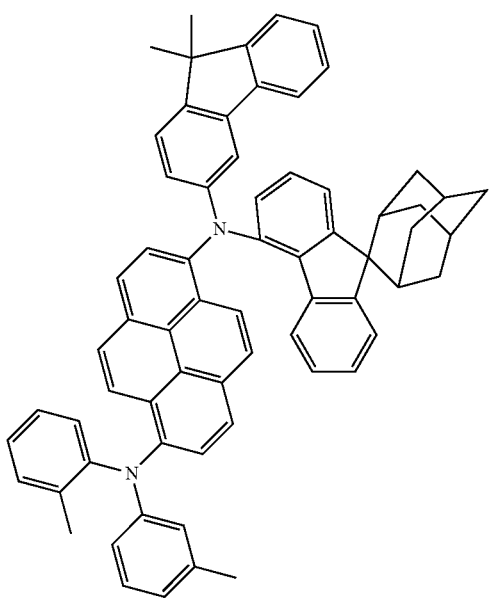
77
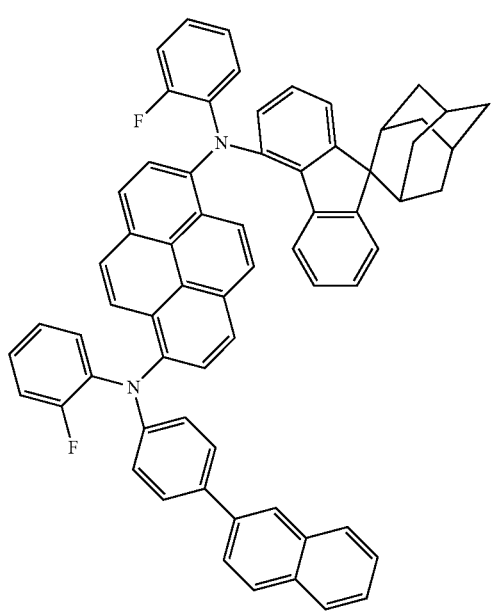
79
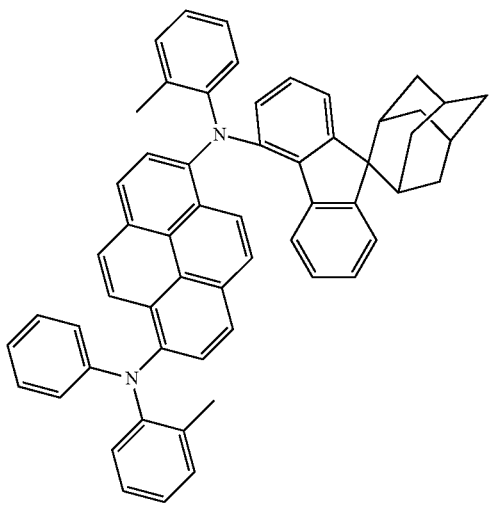

80
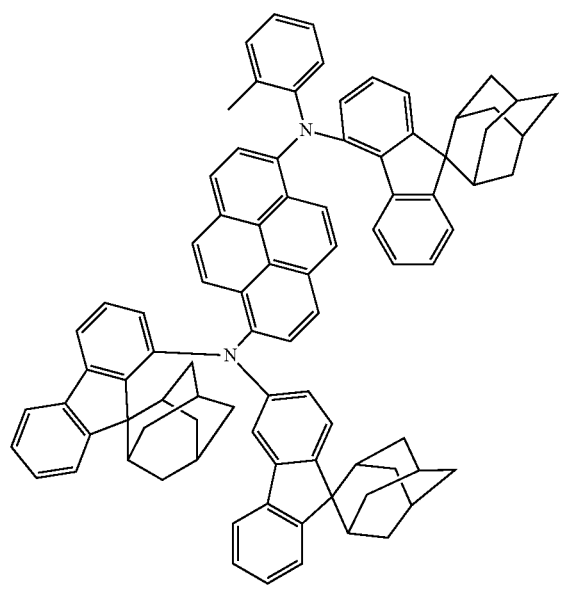
82
81
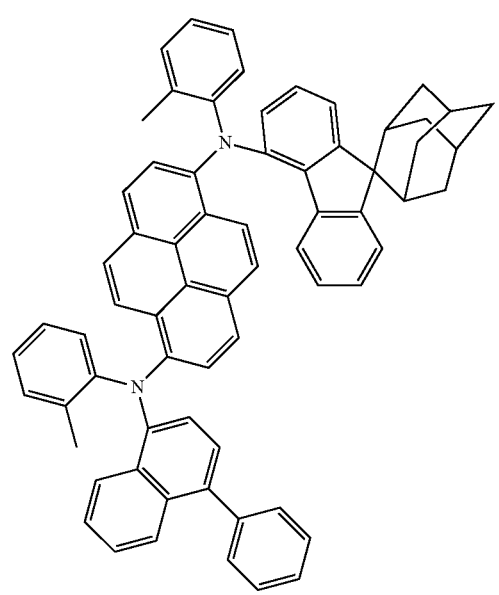
83
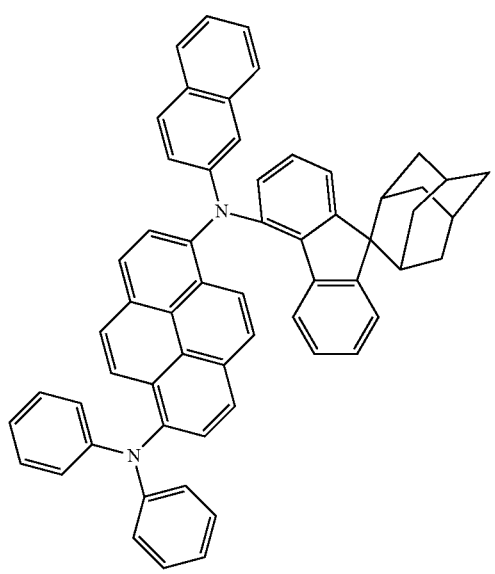

84
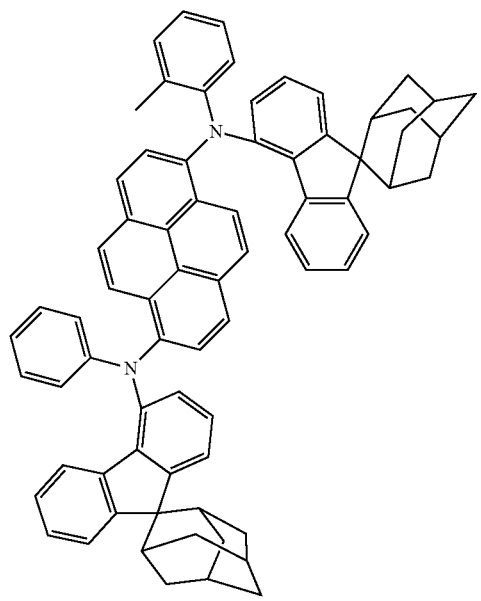
86
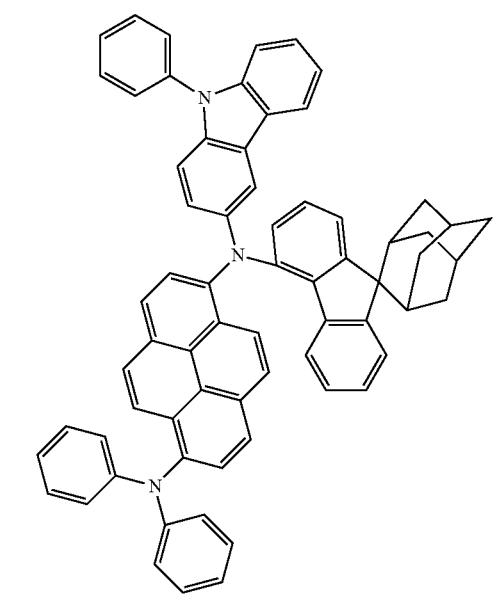
85
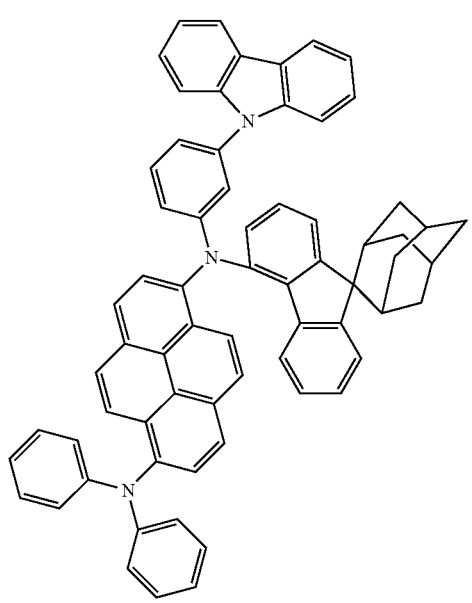
87
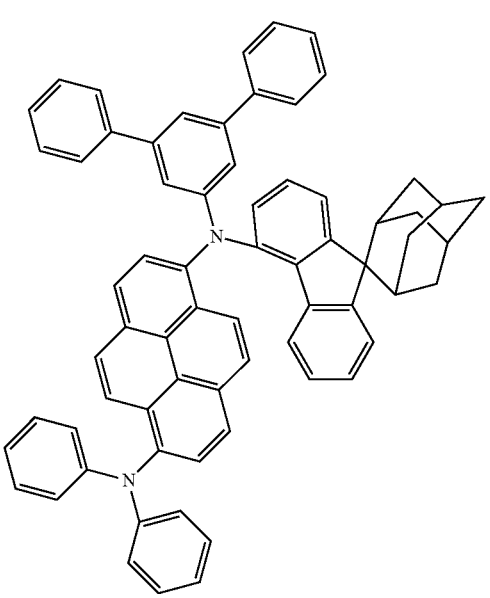

88
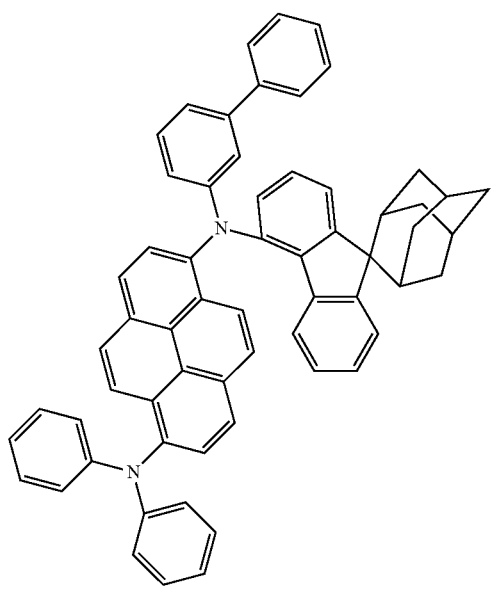
89
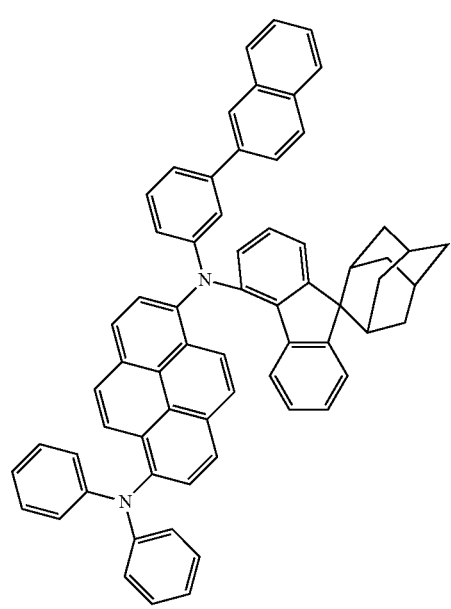
90
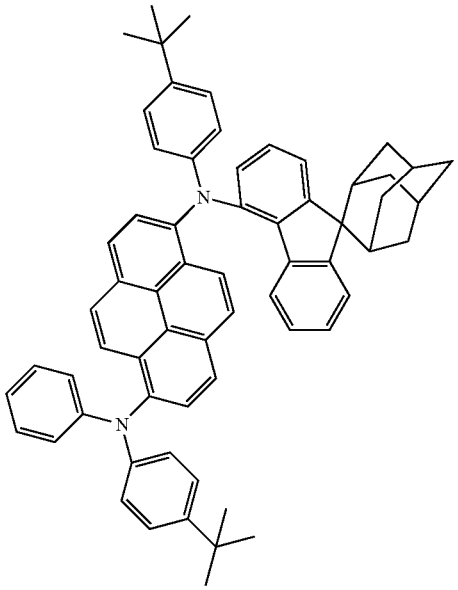
91
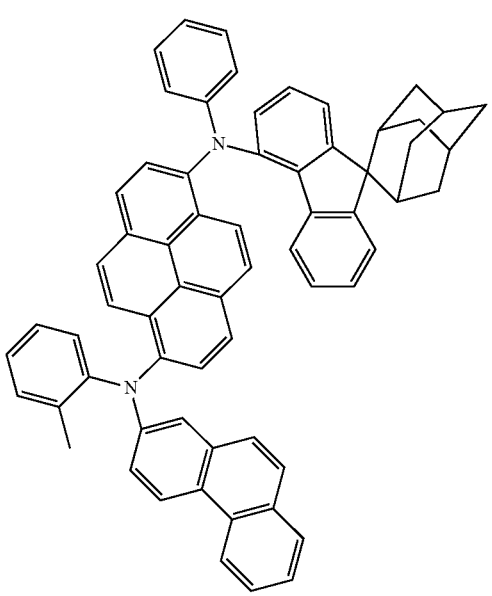

63
-continued
92
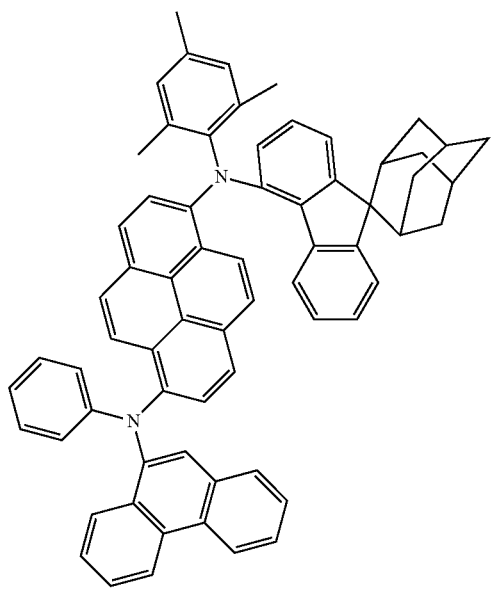
93
94
64
-continued
95
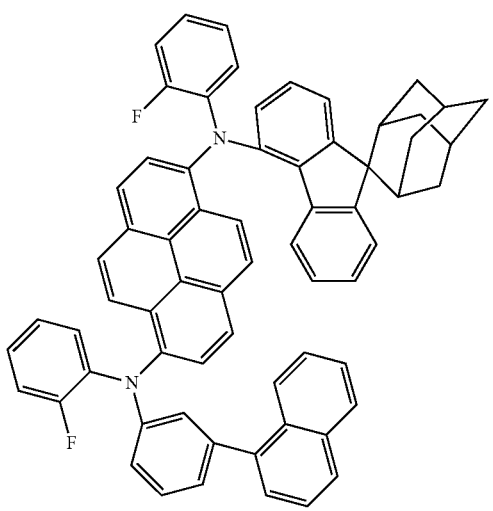
96
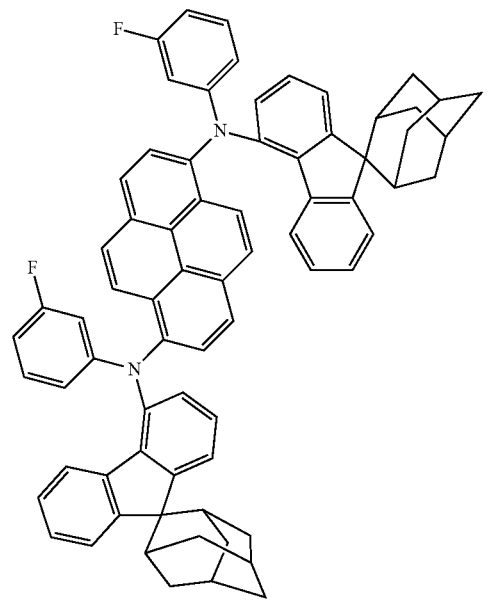
97
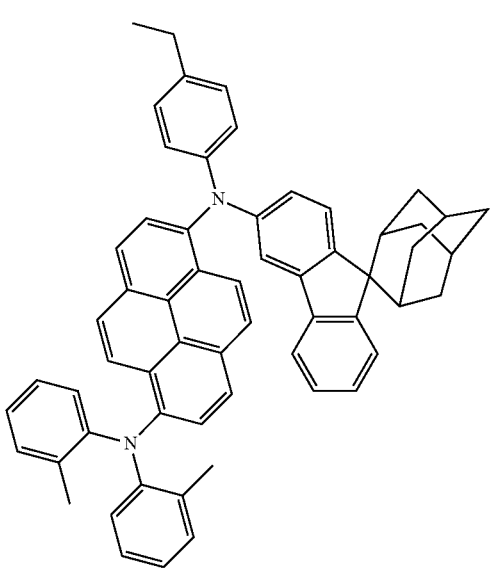

98
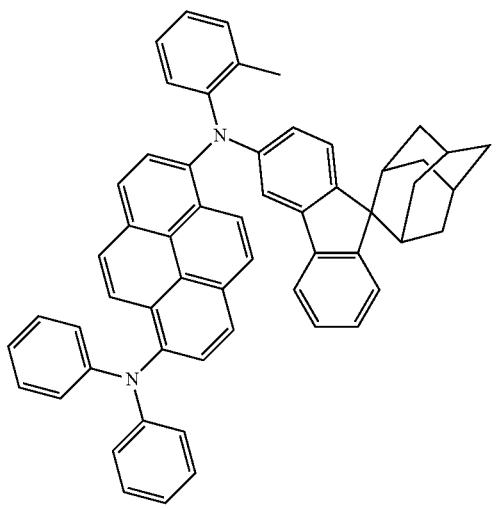
99
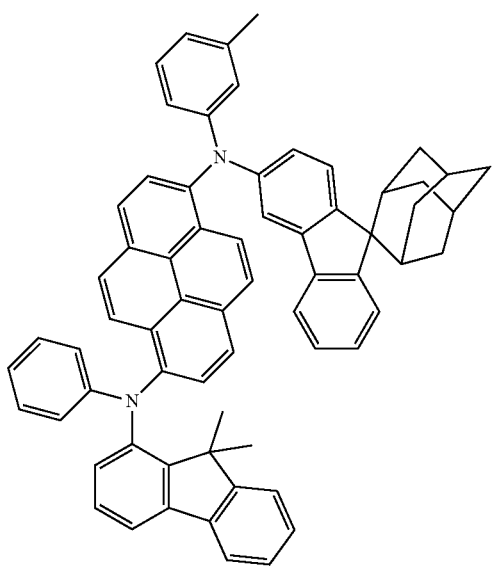
100
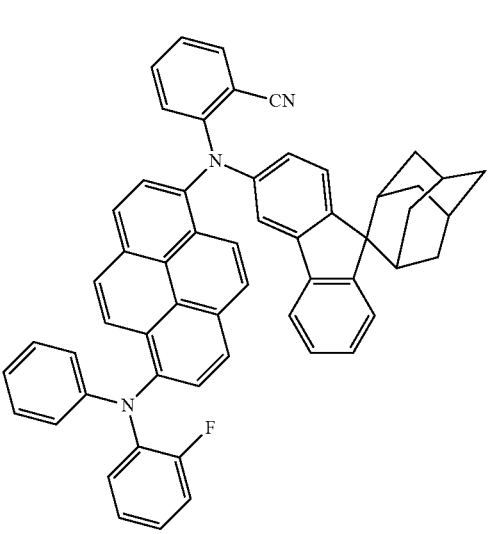
101
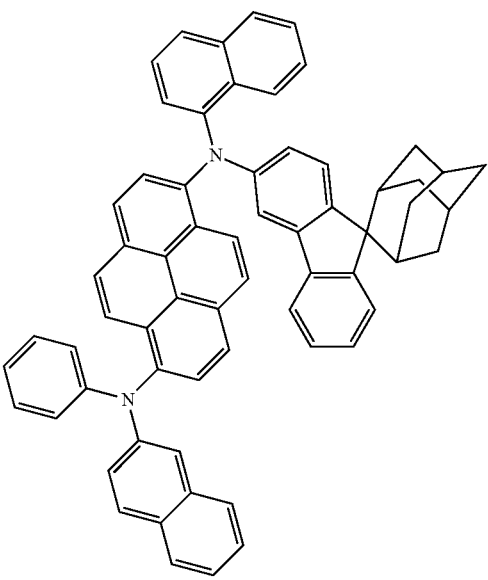
102
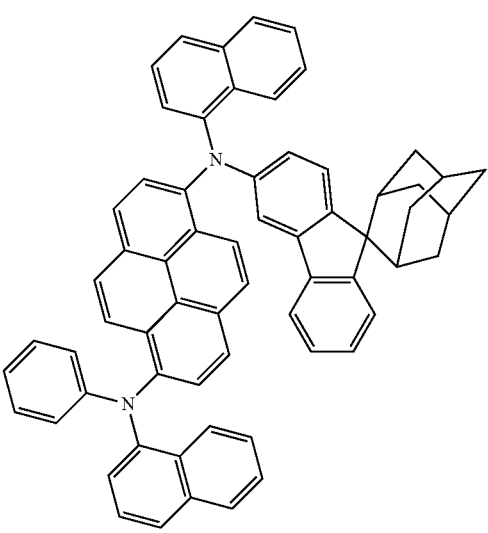

103
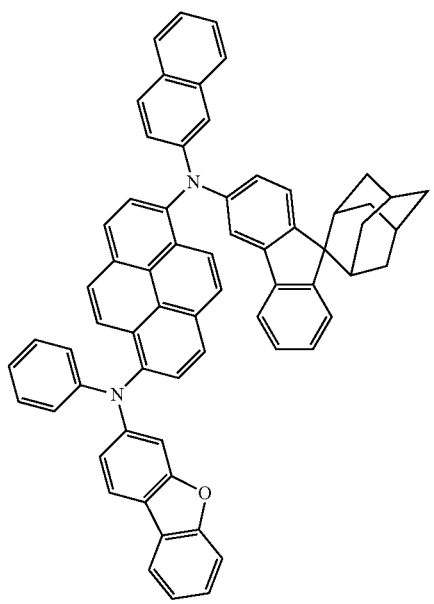
104
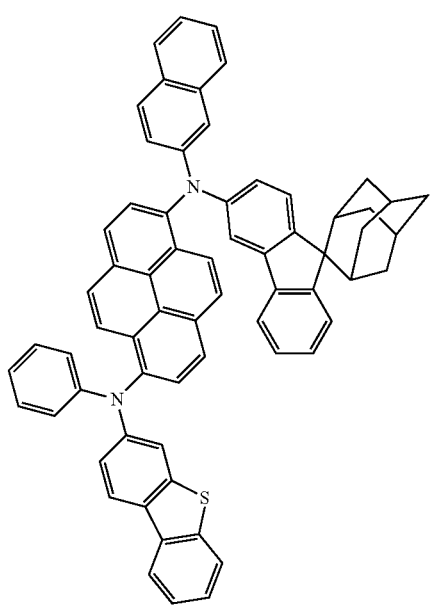
105
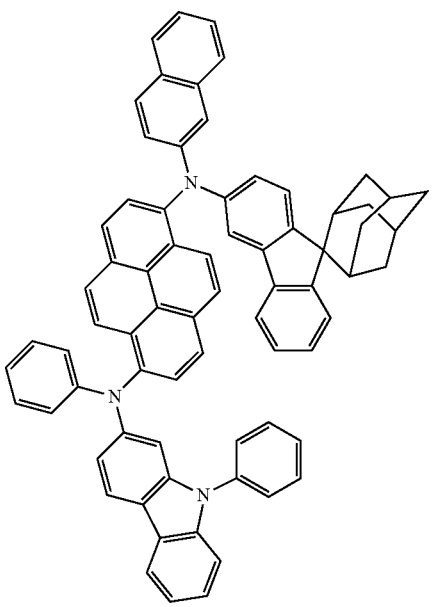
106
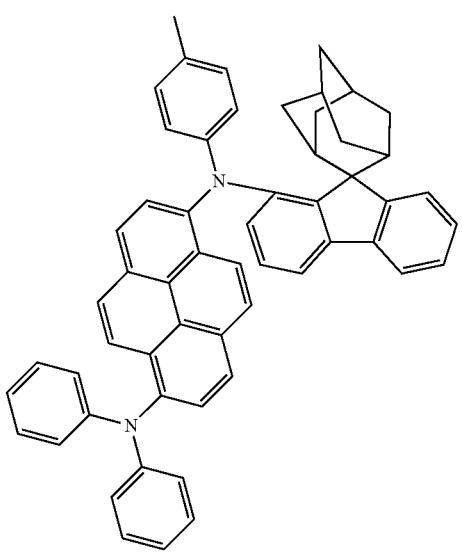

69
-continued
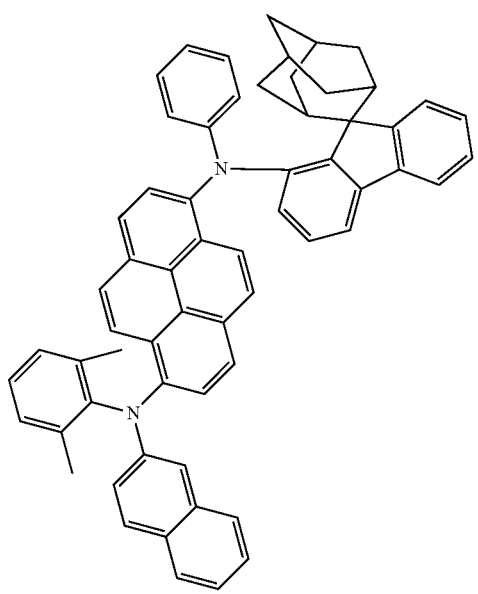
107
70
-continued
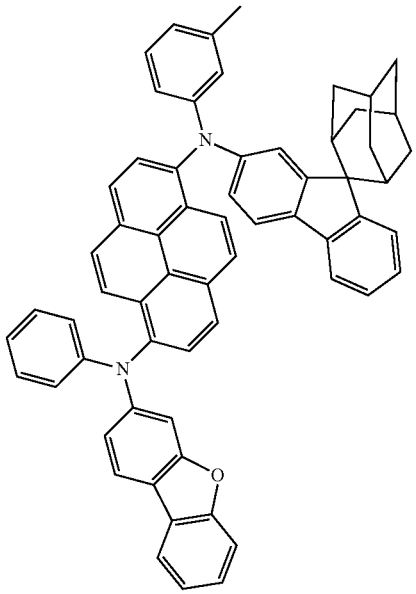
109
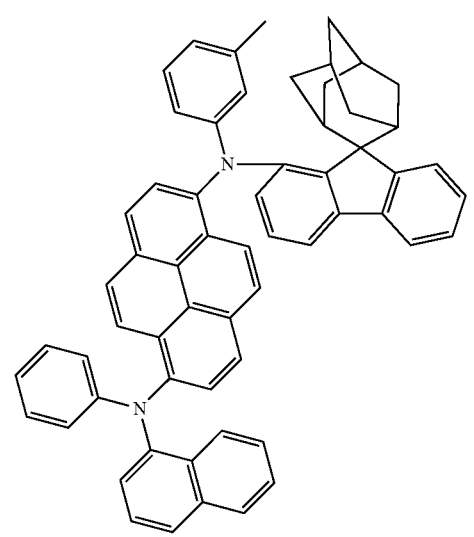
108
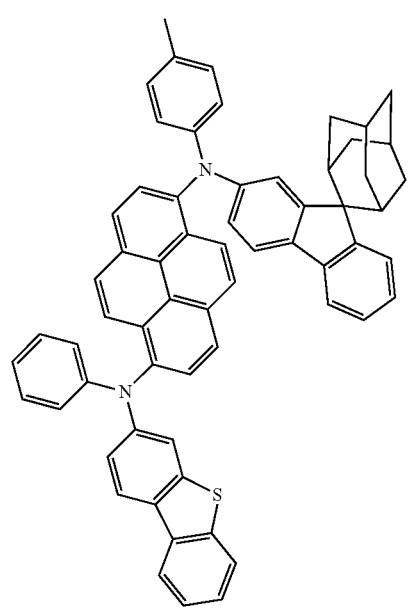
110

-continued
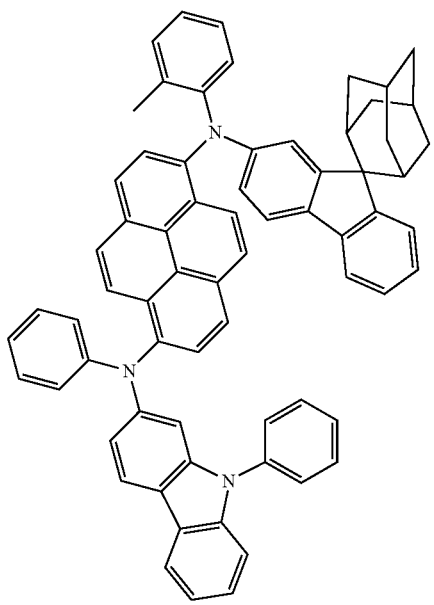
-continued
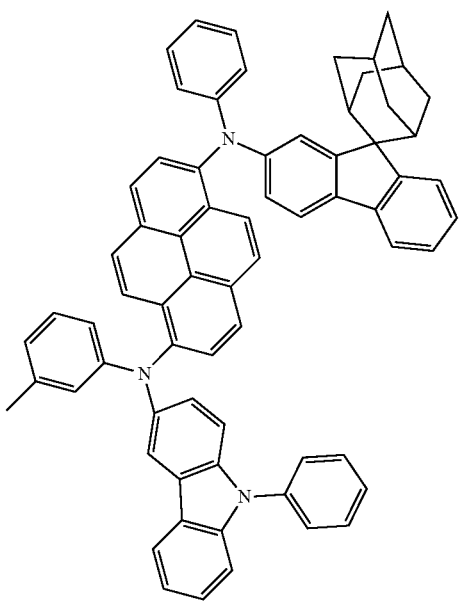

73
-continued
115
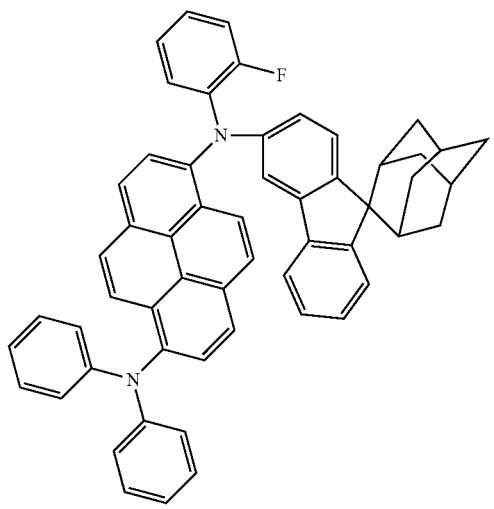
116
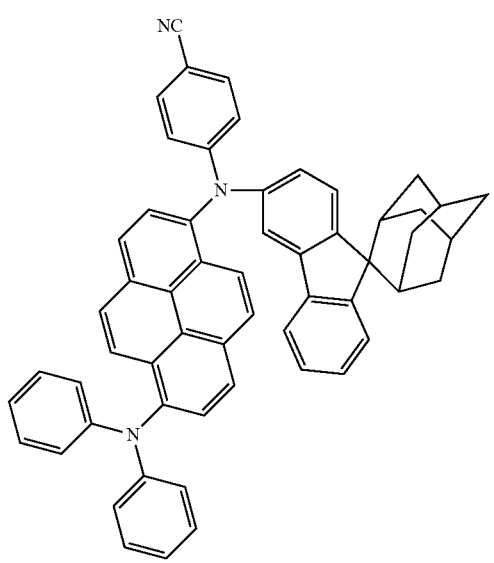
117
74
-continued
118
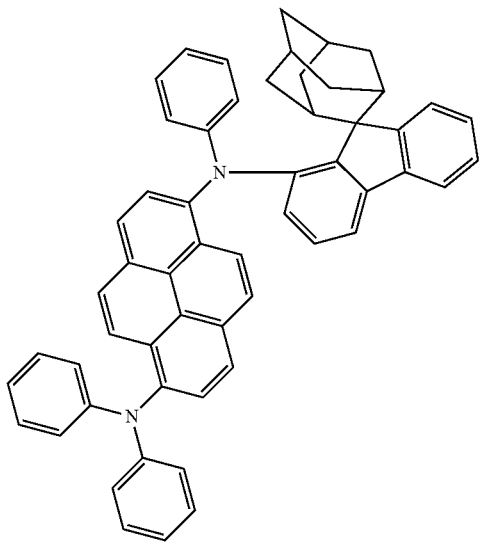
119
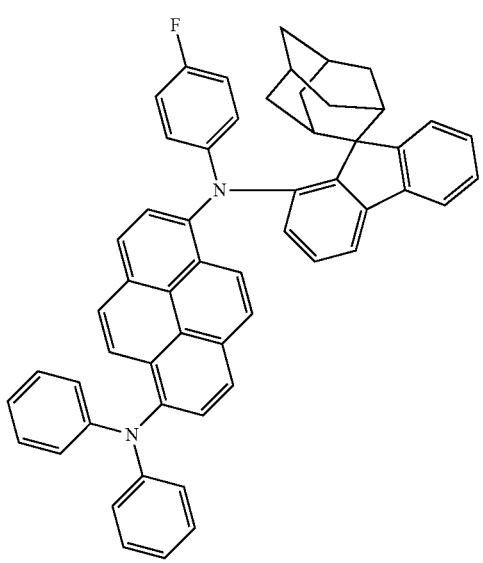

| 120 | 123 |
|---|---|
| 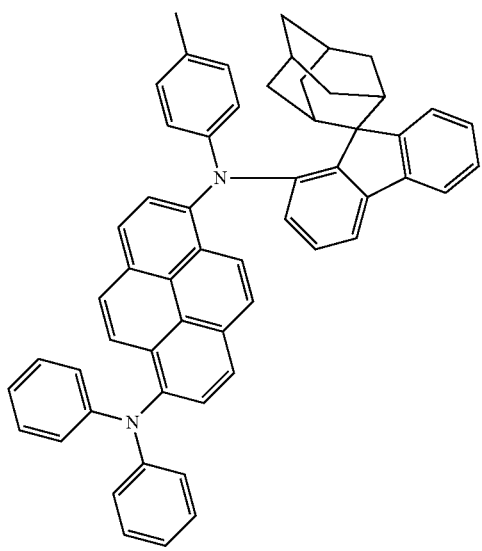 | 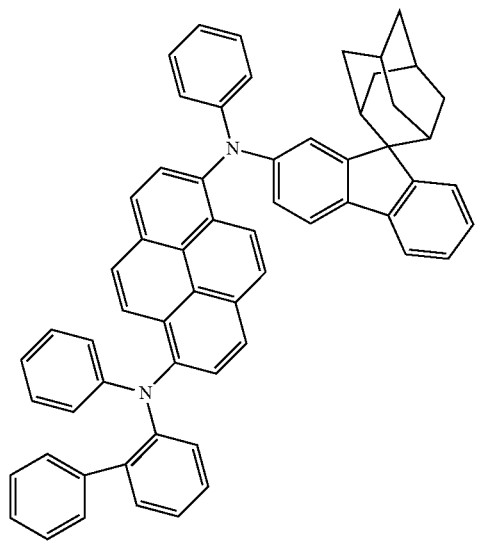 |
| 121 | 124 |
| 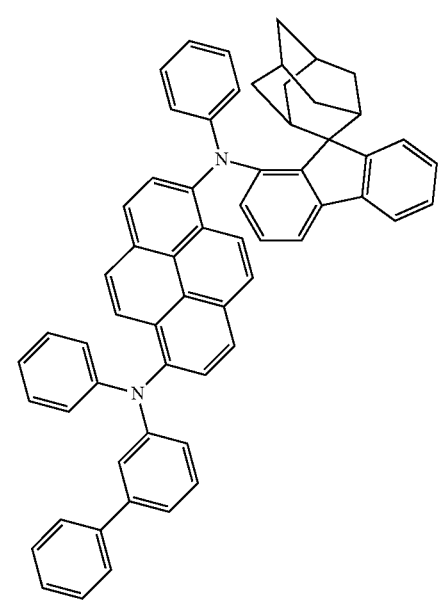 | 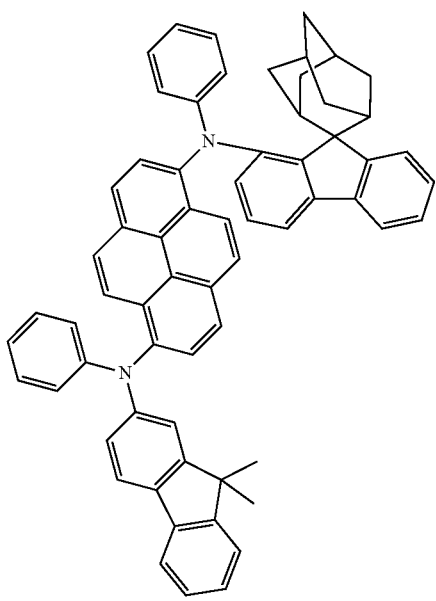 |
| 122 | 125 |
| | 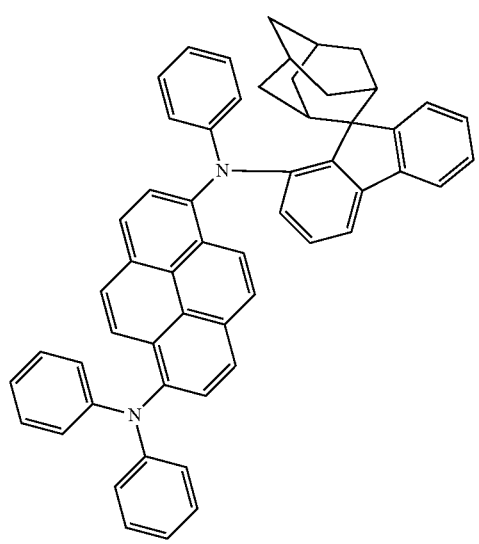 |

126
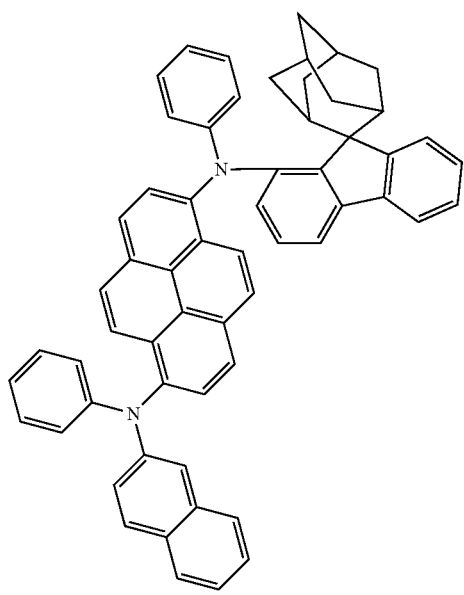
127
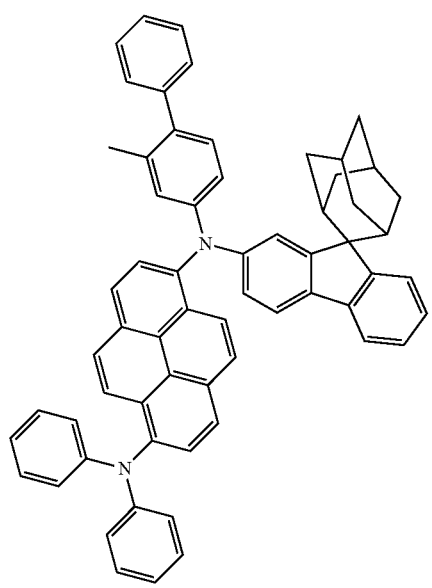
128
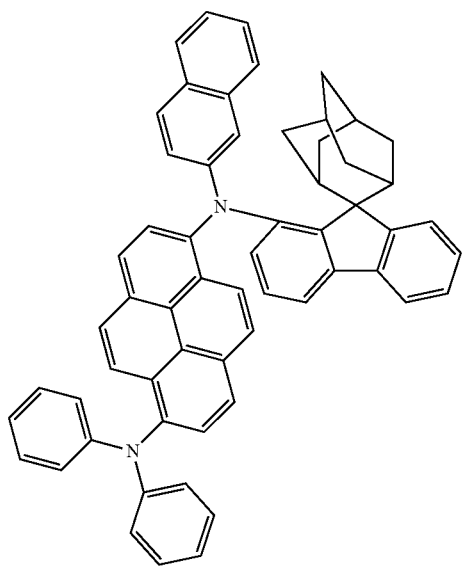
129
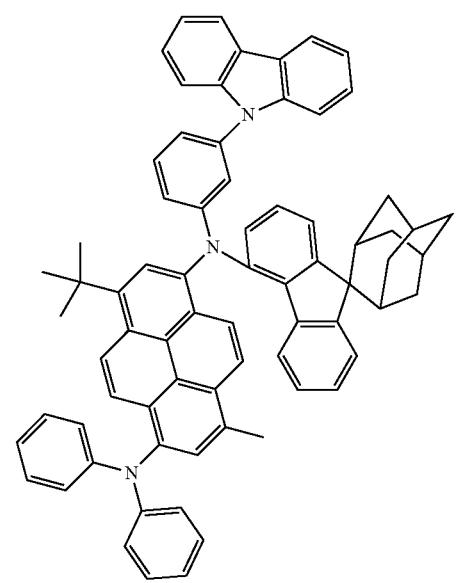

130
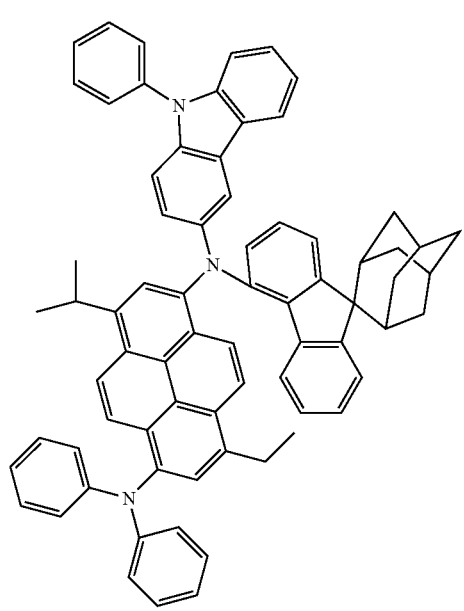
131
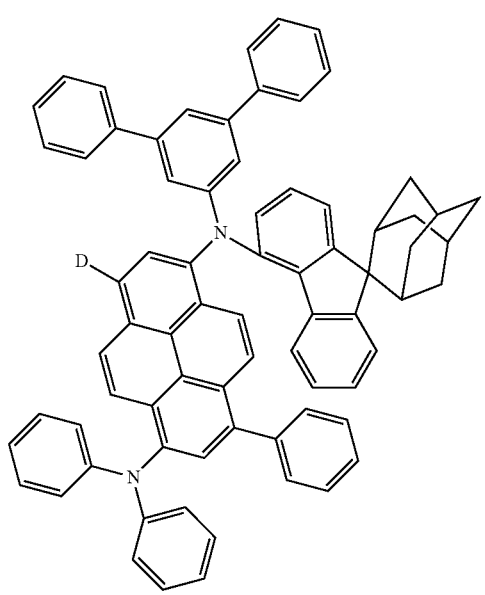
132
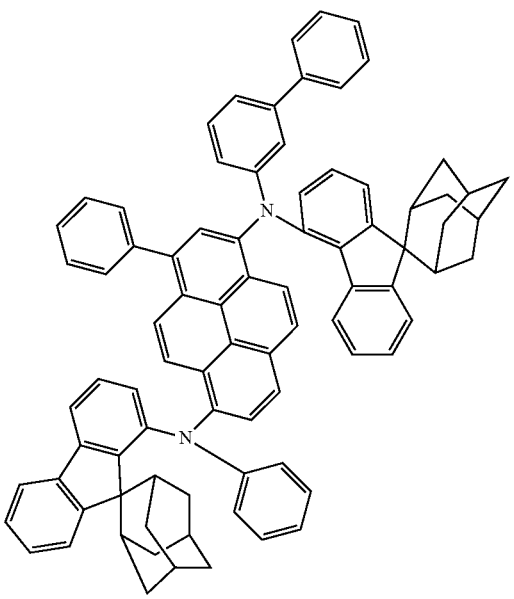
133
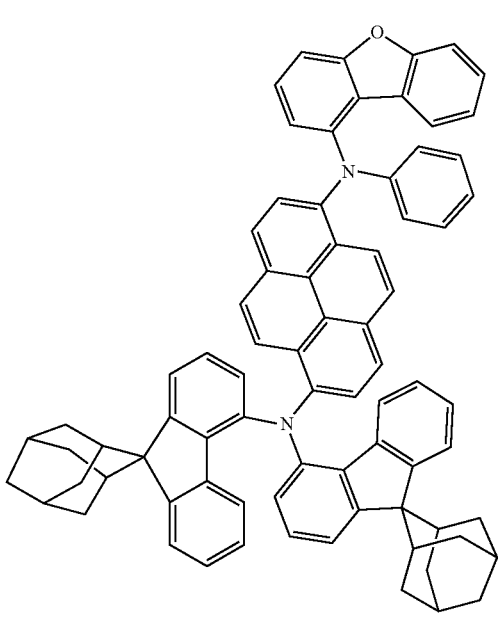

134
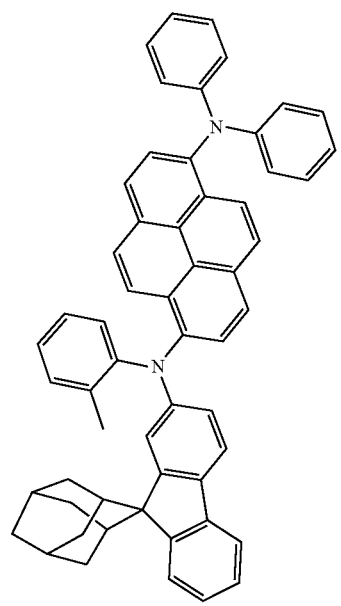
135
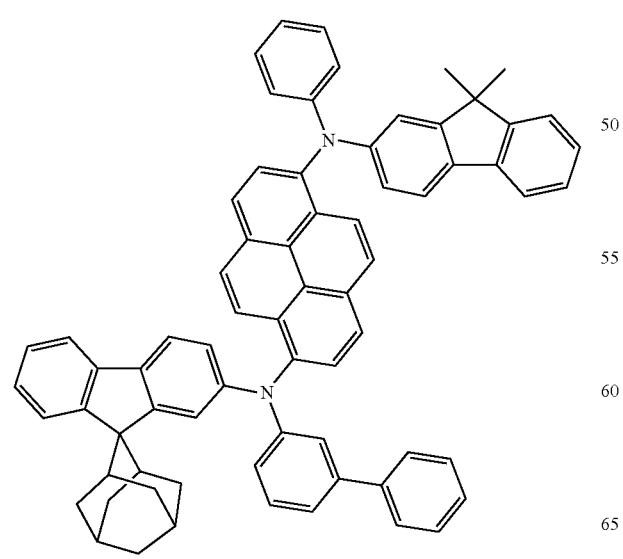
136
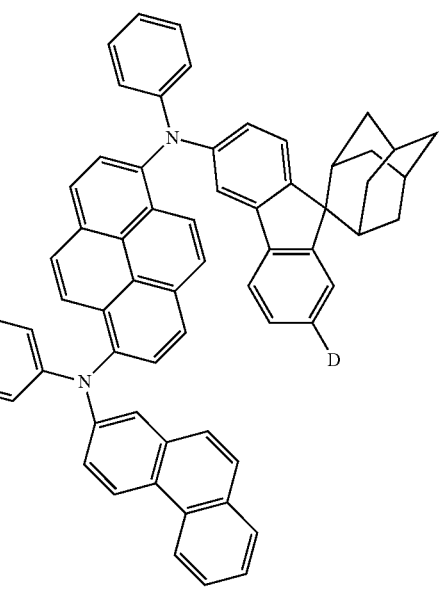
137

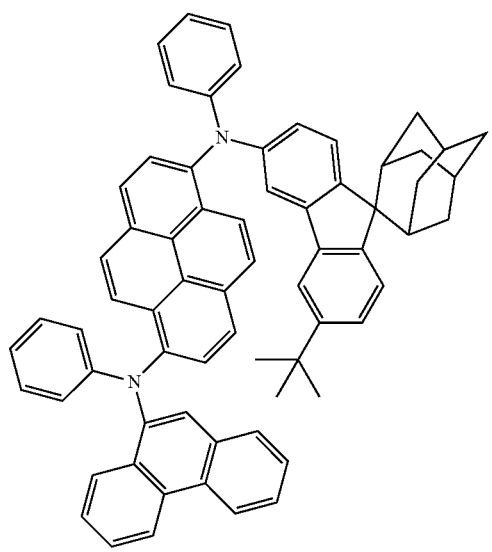
138
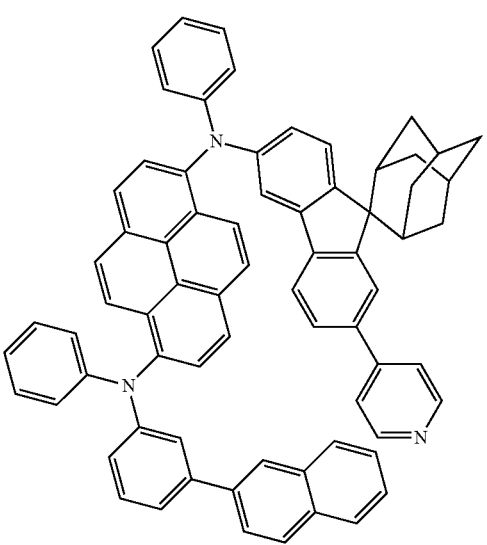
140
139
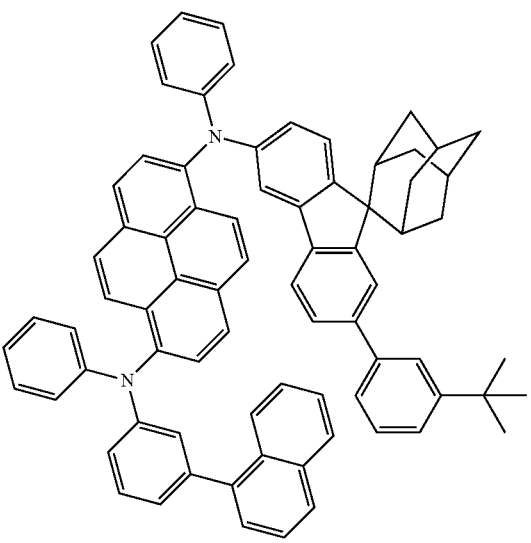
141

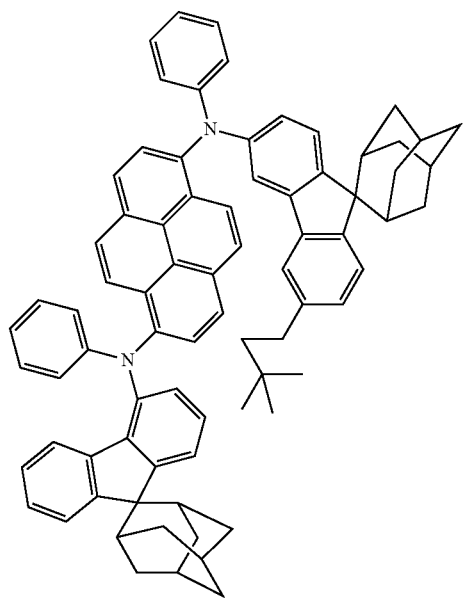
142
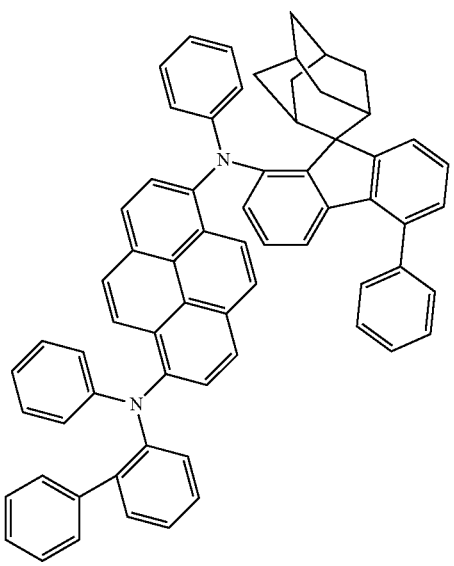
144
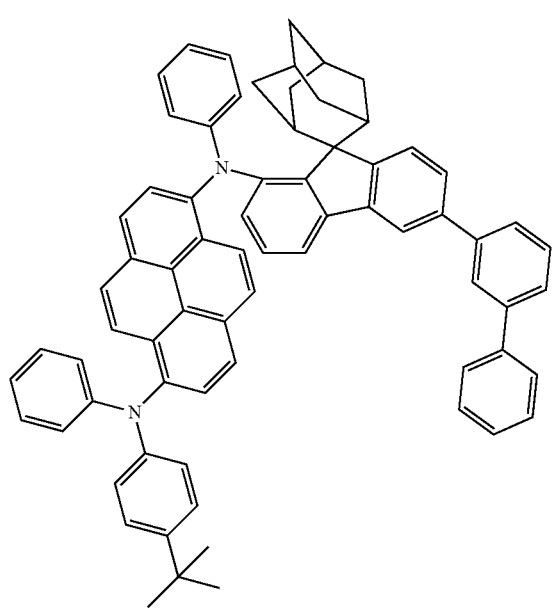
143
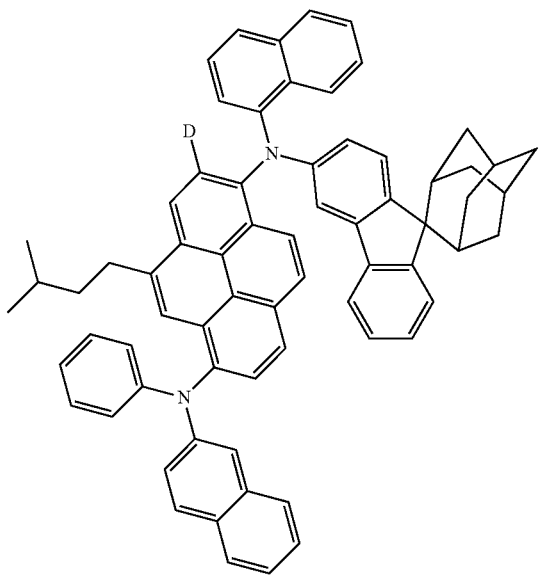
145

87
-continued
146
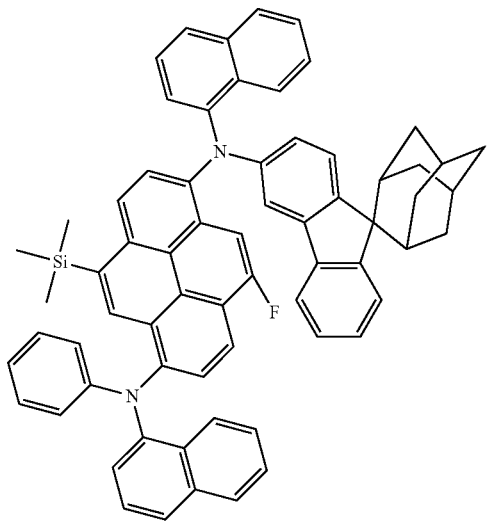
88
-continued
148
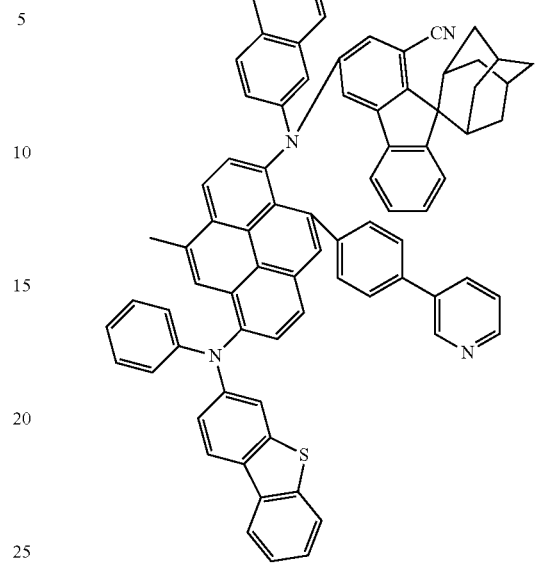
147
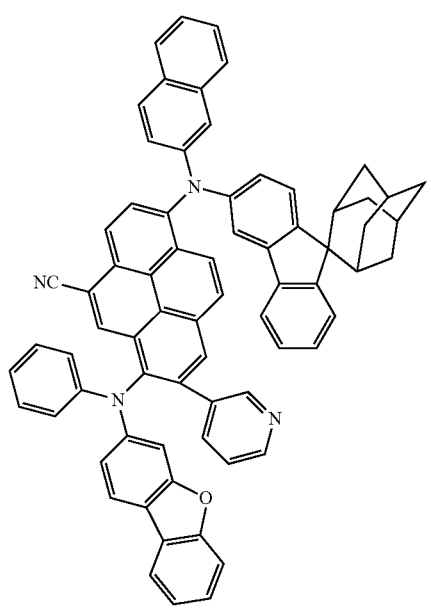
149
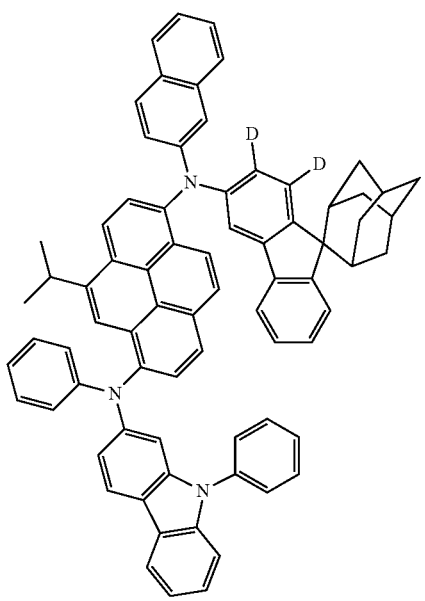

89
-continued
150
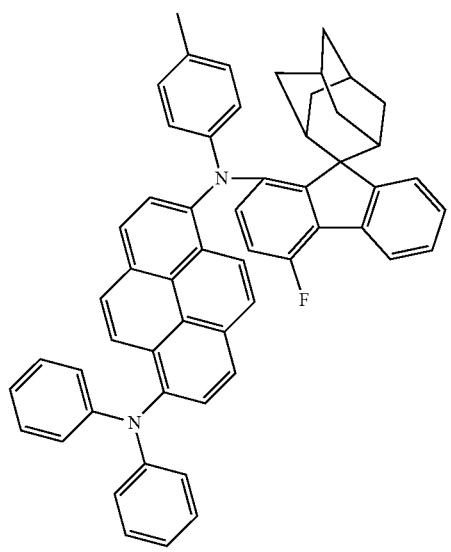
151
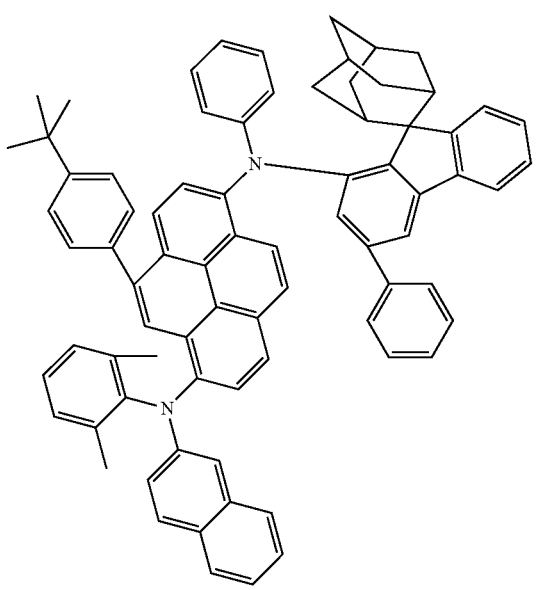
90
-continued
152
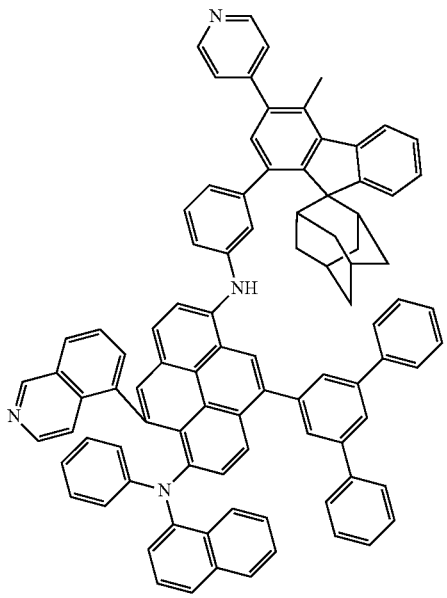
153
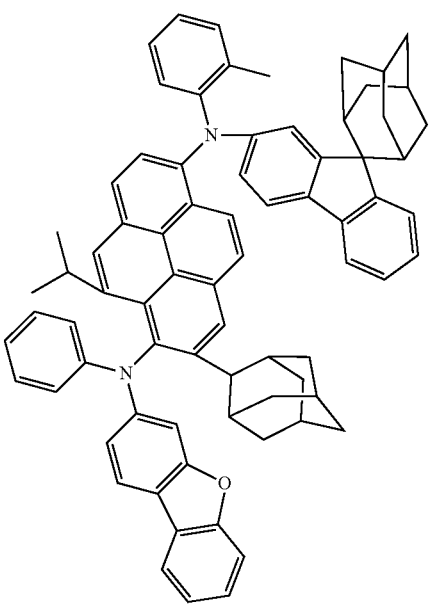

154

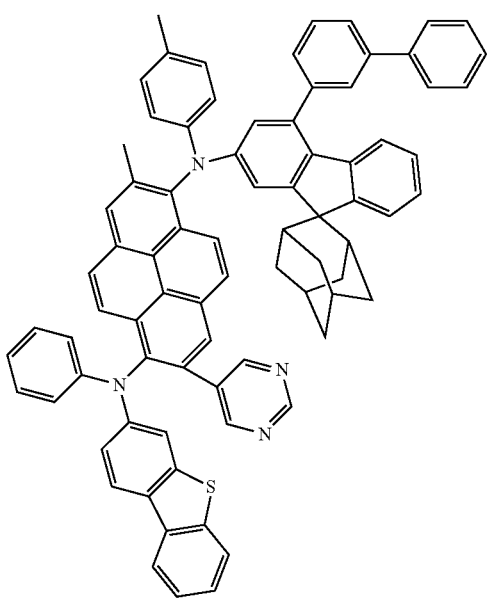

156

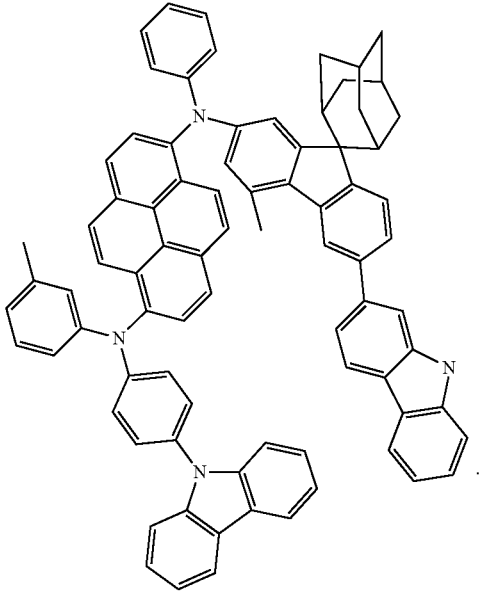

155

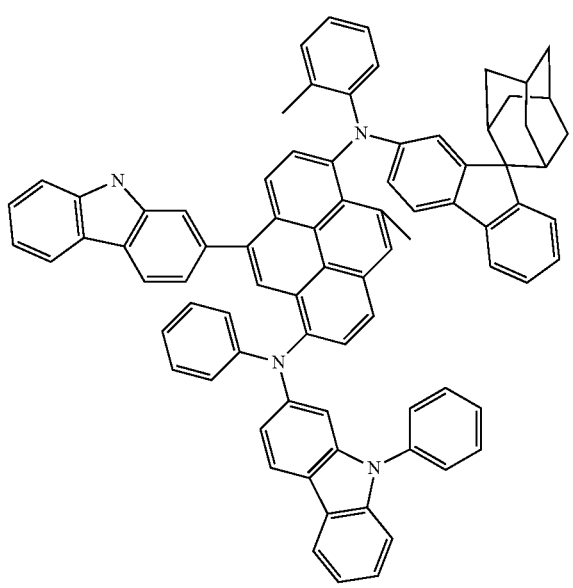

The present disclosure also provides an organic electroluminescent device, comprising an anode and a cathode that are arranged oppositely, and a functional layer arranged between the anode and the cathode, where the functional layer includes the nitrogen-containing compound of the present disclosure.

Optionally, the organic electroluminescent device of the present disclosure may be a blue light-emitting device.

For example, as shown in FIG. 1, the organic electroluminescent device includes an anode 100 and a cathode 200 that are arranged oppositely, and a functional layer 300 arranged between the anode 100 and the cathode 200, where the functional layer 300 includes the nitrogen-containing compound provided in the present disclosure.

Optionally, the functional layer 300 may include an organic electroluminescent layer 330, and the organic electroluminescent layer 330 includes the nitrogen-containing compound of the present disclosure.

Optionally, the organic electroluminescent layer 330 may be composed of a single light-emitting material, or may include a host material and a guest material. Optionally, the organic electroluminescent layer 330 may be composed of a host material and a guest material, where holes injected into the organic electroluminescent layer 330 and electrons injected into the organic electroluminescent layer 330 can recombine in the organic electroluminescent layer 330 to form excitons, the excitons transfer energy to the host material, and then the host material transfers energy to the guest material, such that the guest material can emit light.

The host material of the organic electroluminescent layer 330 may be a metal chelate compound, a bisstyryl derivative, an arylamine derivative, a dibenzofuran derivative, or the other materials, which is not particularly limited in the present disclosure. In an embodiment of the present disclosure, the host material of the organic electroluminescent layer 330 may be α, β-ADN.

The guest material of the organic electroluminescent layer 330 may be a compound with a condensed aryl ring or a derivative thereof, a compound with a heteroaryl ring or a derivative thereof, an arylamine derivative, or the like. In an embodiment of the present disclosure, the guest material of the organic electroluminescent layer 330 is the nitrogen-containing compound of the present disclosure.

In an embodiment of the present disclosure, the organic electroluminescent device may include an anode 100, a hole transport layer 321, an electron blocking layer 322, an organic electroluminescent layer 330 as an energy conversion layer, an electron transport layer 350, and a cathode 200 that are successively stacked. The nitrogen-containing compound provided by the present disclosure can be used for the organic electroluminescent layer 330 of the organic electroluminescent device, which can effectively improve the luminous efficiency and life span of the organic electroluminescent device and reduce the driving voltage of the organic electroluminescent device.

Optionally, the anode 100 may be preferably include a material with a large work function that facilitates the injection of holes into the functional layer. Specific examples of the anode material may include: metals, such as nickel, platinum, vanadium, chromium, copper, zinc, and gold or alloys thereof; metal oxides, such as zinc oxide, indium oxide, indium tin oxide (ITO), and indium zinc oxide (IZO); a recombination of a metal and an oxide, such as ZnO: Al or $SnO_2$: Sb; or conductive polymers, such as poly(3-methylthiophene), poly[3,4-(ethylene-1,2-dioxy)thiophene] (PEDT), polypyrrole, and polyaniline; but are not limited thereto. Preferably, a transparent electrode with indium tin oxide (ITO) may be adopted as the anode.

Optionally, the hole transport layer 321 may include one or more hole transport materials, and the hole transport materials may be selected from carbazole polymers, carbazole-linked triarylamine compounds, or other compounds, which is not particularly limited in the present disclosure. For example, in an embodiment of the present disclosure, the hole transport layer 321 is composed of Compound NPB.

Optionally, the electron blocking layer 322 may include one or more electron blocking materials, and the electron blocking materials may be carbazole polymers or other compounds, which is not particularly limited in the present disclosure. For example, in some embodiments of the present disclosure, the electron blocking layer 322 is composed of Compound TCTA.

Optionally, the electron transport layer 350 may have a single-layer structure or a multi-layer structure, which may include one or more electron transport materials. The electron transport materials may be benzimidazole derivatives, oxadiazole derivatives, quinoxaline derivatives, or other electron transport materials, which is not particularly limited in the present disclosure. For example, in one embodiment of the present disclosure, the electron transport layer 350 may be composed of DBimiBphen and LiQ.

Optionally, the cathode 200 may be include a material with a small work function that facilitates the injection of electrons into the functional layer. Specific examples of the cathode material may include: metals, such as magnesium, calcium, sodium, potassium, titanium, indium, yttrium, lithium, gadolinium, aluminum, silver, tin, and lead or alloys thereof, or multi-layer materials, such as LiF/Al, Liq/Al, $LiO_2$/Al, LiF/Ca, LiF/Al, and $BaF_2$/Ca; but are not limited thereto. Preferably, a metal electrode with magnesium and silver may be adopted as the cathode.

Optionally, as shown in FIG. 1, an hole injection layer 310 may be further provided between the anode 100 and the hole transport layer 321 to enhance the ability to inject holes into the hole transport layer 321. The hole injection layer 310 can be made of a benzidine derivative, a starburst arylamine compound, a phthalocyanine derivative, or another material, which is not particularly limited in the present disclosure. In an embodiment of the present disclosure, the hole injection layer 310 may be composed of m-MTDATA.

Optionally, as shown in FIG. 1, an electron injection layer 360 may be further provided between the cathode 200 and the electron transport layer 350 to enhance the ability to inject electrons into the electron injection layer 350. The electron injection layer 360 may include an inorganic material such as an alkali metal sulfide and an alkali metal halide, or may include a complex of an alkali metal and an organic substance. In an embodiment of the present disclosure, the electron injection layer 360 may include LiQ.

Optionally, an hole blocking layer 340 may also be provided between the organic electroluminescent layer 330 and the electron injection layer 350.

An embodiment of the present disclosure also provides an electronic apparatus, comprising the organic electroluminescent device described above. Since the electronic apparatus has the organic electroluminescent device, the electronic apparatus has the same beneficial effects as the organic electroluminescent device, which will not be repeated in the present disclosure.

Figure 2:
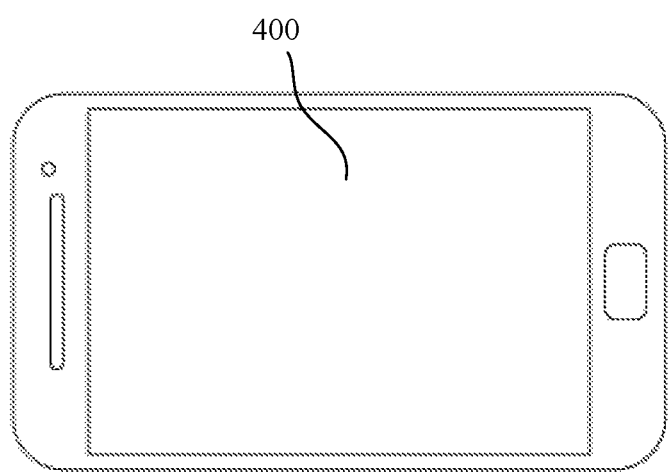
FIG. 2 is a schematic structure diagram of an electronic apparatus according to an embodiment of the present disclosure.

For example, as shown in FIG. 2, the present disclosure provides an electronic apparatus 400 comprising the organic electroluminescent device. The electronic apparatus 400 may be a display apparatus, a lighting apparatus, an optical communication apparatus, or another electronic apparatus, including but not limited to computer screen, mobile phone screen, television set, electronic paper, emergency light, optical module and the like. Since the electronic apparatus 400 has the organic electroluminescent device, the electronic apparatus has the same beneficial effects as the organic electroluminescent device, which will not be repeated in the present disclosure.

the present disclosure will be further described in detail below through examples. However, the following examples are only illustrations of the present disclosure, and do not limit the present disclosure.

Synthesis of Compound:

Synthesis of Intermediate-1-A

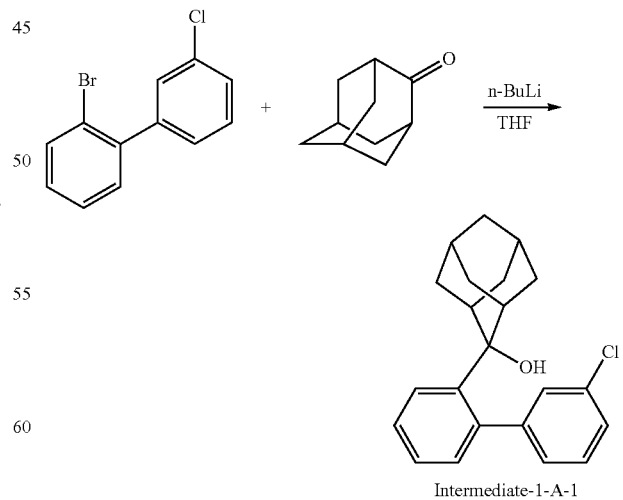

Intermediate-1-A-1

2'-bromo-3-chlorobiphenyl (100 g, 373.8 mmol) was added to a three-necked flask with tetrahydrofuran (THF) (1 L), and a resulting mixture was cooled to −80° C.; then n-butyl lithium (19.15 g, 299.06 mmol) was added dropwise, and a resulting mixture was incubated for 1 h; then adamantanone (44.92 g, 299.06 mmol) was added dropwise, and a resulting mixture was incubated for 1 h, then warmed to room temperature, and stirred overnight; a pH was adjusted to 7.0 with hydrochloric acid (2 mol/L), and a resulting reaction solution was filtered to obtain a white crude product; and the crude product was slurried with n-heptane to obtain Intermediate-1-A-1 as a white solid (92.86 g, yield: 87%).

Synthesis of Intermediate-1-B

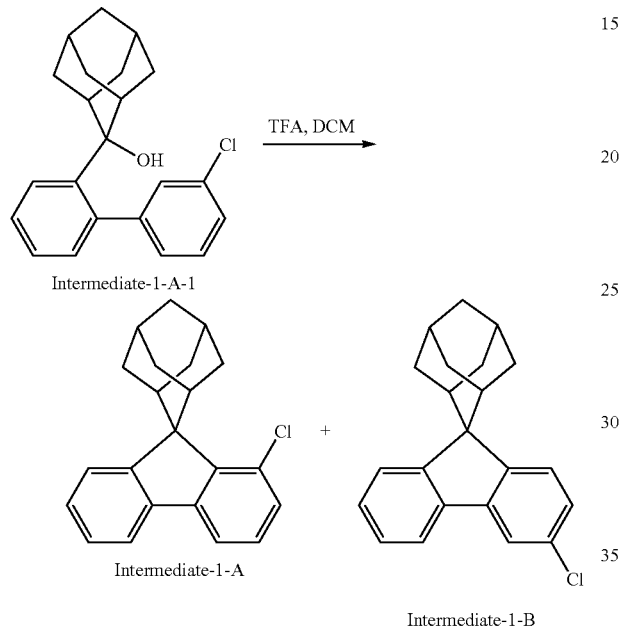

Intermediate-1-A-1 (92.86 g, 275.63 mmol), trifluoroacetic acid (94.28 g, 826.89 mmol), and dichloromethane (900 mL) were added to a three-necked flask, and a resulting mixture was stirred at room temperature for 2 h under nitrogen protection; a sodium hydroxide aqueous solution was added to the flask until a resulting reaction solution was neutral, then the reaction solution was allowed to be separated into layers, and a resulting organic phase was dried with anhydrous magnesium sulfate, filtered, and subjected to solvent removal under reduced pressure; and an obtained crude product was subjected to silica gel column chromatography with dichloromethane/n-heptane (1:2) to obtain Intermediate-1-A as a white solid (50.43 g, yield: 54%) and Intermediate-1-B (42.42 g, yield: 46%).

NMR data of Intermediate 1-B: $^1$HNMR (400 MHz, CDCl$_2$): 8.11 (d, 1H), 8.03 (d, 1H), 7.41-7.63 (m, 2H), 7.37-7.39 (m, 1H), 7.30-7.33 (m, 1H), 7.23-7.24 (m, 1H), 2.88-2.93 (m, 2H), 2.81-2.85 (m, 2H), 2.19 (s, 2H), 1.99 (s, 2H), 1.77-1.83 (m, 4H), 1.54 (s, 2H).

In the following examples, Intermediate-1-X-1 and Intermediate-1-X were synthesized by the same method as the synthesis method of Intermediate-1-A and Intermediate-1-B, except that Compound SM-1 in Table 1 was used instead of 2'-bromo-3-chlorobiphenyl, where X can be C. For example, Compound SM-1 can be 2-bromo-2'-chloro-1,1'-biphenyl, and each Compound SM-1 can lead to a unique Intermediate-1-X correspondingly. For example, the synthesis process can be shown in a reaction equation 1, and the reaction equation 1 can be:

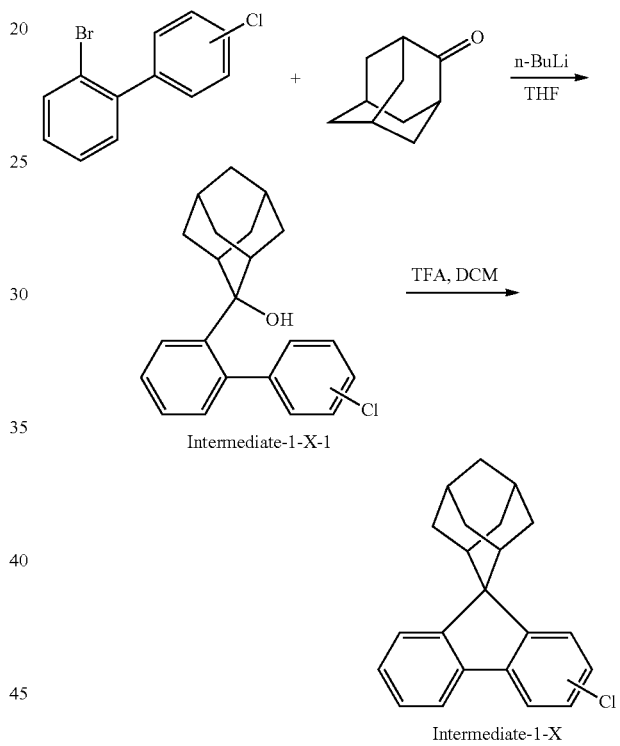

Synthesized Intermediate-1-X was Shown in Table 1

TABLE 1

| Synthesis List of Intermediate-1-X | | |
|---|---|---|
| | Intermediate-1-C | Intermediate-1-D |
| SM-1 | Br-C6H4-C6H4-Cl | Br-C6H4-C6H4-Cl |

TABLE 1-continued

Synthesis List of Intermediate-1-X

| | Intermediate-1-C | Intermediate-1-D |
|---|---|---|
| Intermediate-1-X-1 | ![structure] | ![structure] |
| Intermediate-1-X | ![structure] | ![structure] |
| Mass (g) | 75.21 | 73.32 |
| Yield (%) | 81 | 80 |

Synthesis of Intermediate-2-A

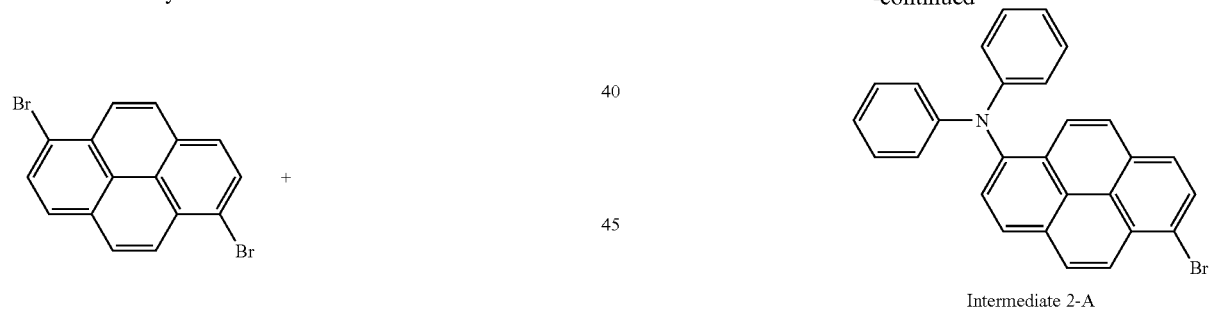

Intermediate 2-A

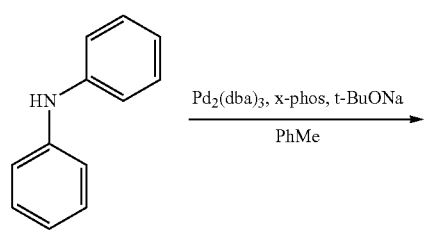

1,6-dibromopyrene(50.00 g, 138.87 mmol), diphenylamine(23.50 g, 138.87 mmol), tris(dibenzylideneacetone)dipalladium(1.27 g, 1.38 mmol), 2-dicyclohexylphosphino-2',4',6'-triisopropylbiphenyl(1.14 g, 2.77 mmol), sodium tert-butoxide (20.01 g, 208.31 mmol), and toluene (500 mL) were added to a 500 mL of reaction flask, and a resulting mixture was heated to 110° C. under nitrogen protection and then stirred for 3 h under reflux; a resulting reaction solution was cooled to room temperature, dichloromethane and water were added to the reaction solution for extraction, and a resulting organic phase was dried with anhydrous magnesium sulfate and then filtered to obtain a filtrate; the filtrate was passed through a short silica gel column, the solvent was removed from the filtrate under reduced pressure; and a crude product was purified through recrystallization with a dichloromethane/n-heptane system (1:3) to obtain an Intermediate-2-A (50.43 g, yield: 81%).

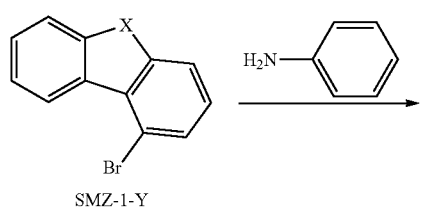

SMZ-1-Y

In the following examples, Intermediate-2-X was synthesized by the same method as the synthesis method of Intermediate-2-A, except that Compound SM-2 was used instead of diphenylamine, where X was B, C, D, E, F, G, H, or I. For example, Compound SM-2 can be N-phenyl-3-biphenylamine, N-phenyl-2(9,9-dimethyl-9H-fluorene)amine, 1-naphthylaminobenzene, 2-methyldiphenylamine, di(3-biphenyl)amine, N-(4-(1-naphthyl)phenyl)-4-biphenylamine, N-2,6-diphenyl-2-naphthylamine, N-phenyl-2-naphthylamine, SMZ-1 or SMZ-2, and each Compound SM-2 can lead to a unique Intermediate-2-X correspondingly. For example, the synthesis process can be shown in a reaction equation 2, and the reaction equation 2 can be:

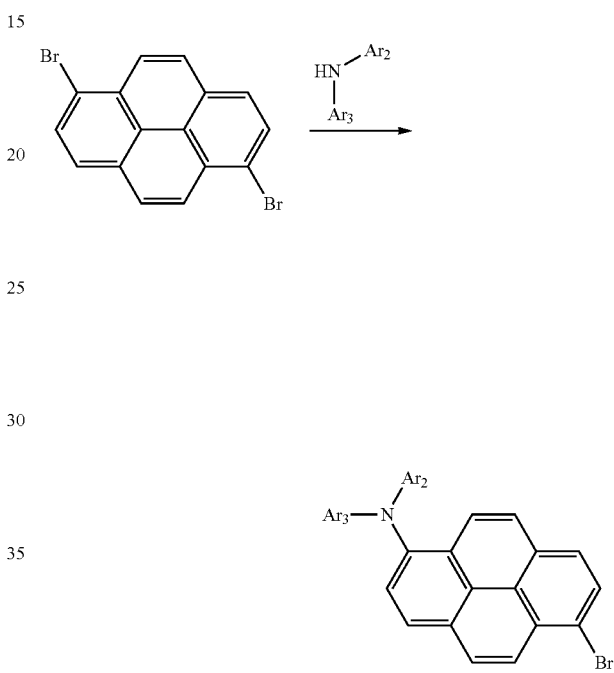

SMZ-Y was synthesized by the same method as the synthesis method of Intermediate-2-A, except that SMZ was used instead of 1,6-dibromopyrene, and phenylamine was used instead of diphenylamine, where Y can be 1 or 2 and X can be O or S. For example, SMZ-1-Y can be 1-bromodibenzofuran or 1-bromodibenzothiophene. Each SMZ formed by X can lead to corresponding SMZ-Y

| SMZ-1-Y | Diphenylamine | SMZ-Y | Mass (g) | Yield (%) |
|---|---|---|---|---|
| SMZ-1-1 | H₂N-phenyl | SMZ-1 | 10.03 | 72 |
| SMZ-1-2 | H₂N-phenyl | SMZ-2 | 11.31 | 71 |

Synthesized Intermediate-2-X was Shown in Table 2

TABLE 2

Synthesis List of Intermediate-2-X

| Intermediate No. | SM-2 | Structural formula | Mass (g) | Yield (%) |
|---|---|---|---|---|
| Intermediate-2-B | | | 59 | 81 |
| Intermediate-2-C | | | 62.7 | 80 |
| Intermediate-2-D | | | 57.4 | 83 |
| Intermediate-2-E | | | 51.3 | 80 |

TABLE 2-continued
Synthesis List of Intermediate-2-X
| Intermediate No. | SM-2 | Structural formula | Mass (g) | Yield (%) |
|---|---|---|---|---|
| Intermediate-2-F | | | 68.3 | 82 |
| Intermediate-2-G | | | 73.1 | 81 |
| Intermediate-2-H | | | 58.4 | 80 |
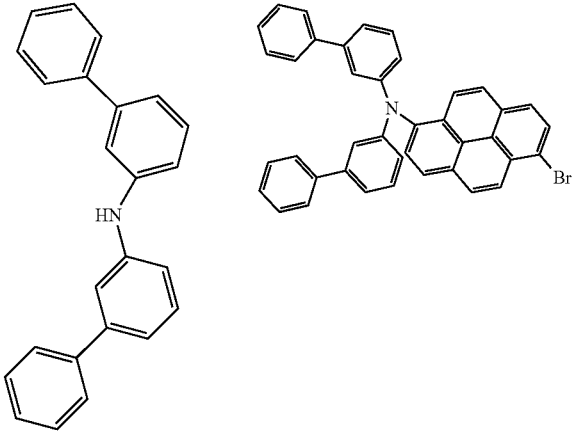
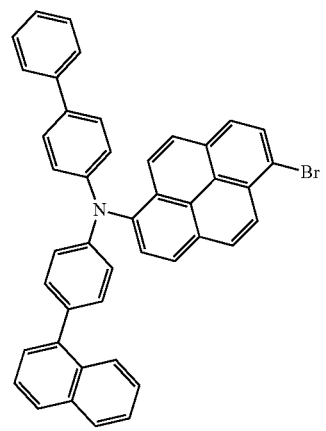 [SMILES: Brc1ccc2ccc3c(N(c4ccc(-c5ccccc5)cc4)c4ccc(-c5cccc6ccccc56)cc4)ccc4ccc1c2c43]
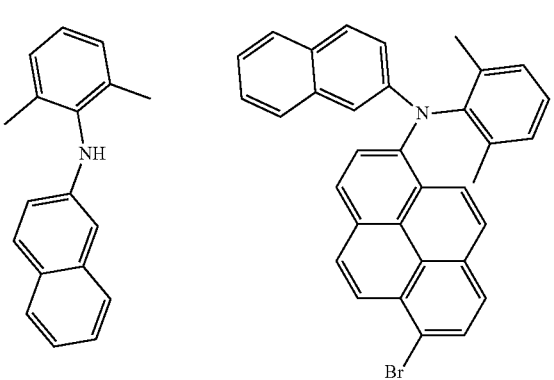

TABLE 2-continued

Synthesis List of Intermediate-2-X

| Intermediate No. | SM-2 | Structural formula | Mass (g) | Yield (%) |
|---|---|---|---|---|
| Intermediate-2-I | | | 56.7 | 82 |
| Intermediate-2-J | SMZ-1 | | 55.8 | 79 |
| Intermediate-2-K | SMZ-2 | | 53.4 | 77 |

Synthesis of Intermediate-3-A

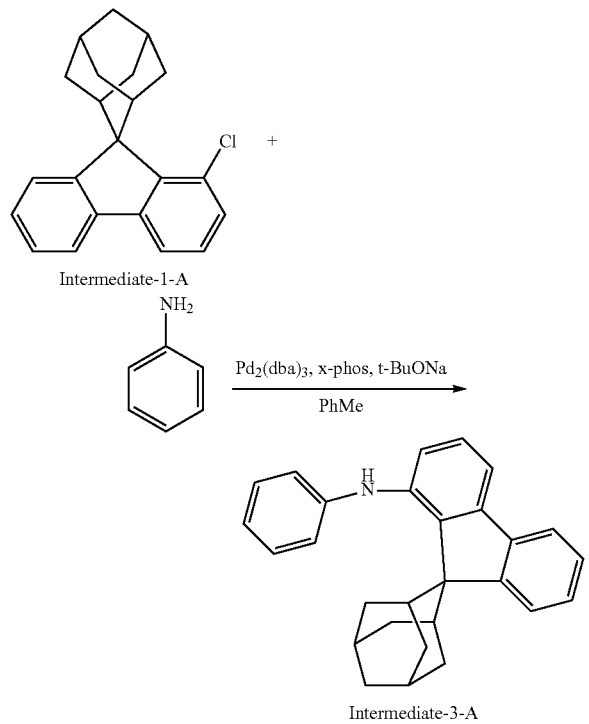

Intermediate-1-A (5.0 g, 15.58 mmol), phenylamine (1.45 g, 15.58 mmol), tris(dibenzylideneacetone)dipalladium (0.14 g, 0.15 mmol), 2-dicyclohexylphosphino-2',4',6'-triisopropylbiphenyl (0.12 g, 0.31 mmol), sodium tert-butoxide (2.25 g, 23.37 mmol), and toluene (50 mL) were added to a 100 mL reaction flask, and a resulting mixture was heated to 110° C. under nitrogen protection and then stirred for 5 h under reflux; a resulting reaction solution was cooled to room temperature, dichloromethane and water were added to the reaction solution for extraction, and a resulting organic phase was dried with anhydrous magnesium sulfate and then filtered to obtain a filtrate; the filtrate was passed through a short silica gel column, and the solvent was removed from the filtrate under reduced pressure; and a crude product was purified through recrystallization with a dichloromethane/n-heptane system (1:5) to obtain Intermediate-3-A (4.70 g, yield: 80%).

Intermediate-1-C (5.0 g, 14.8 mmol), ammonia water (0.25 g, 14.84 mmol), tris(dibenzylideneacetone)dipalladium (0.67 g, 0.74 mmol), 2-dicyclohexylphosphino-2',4',6'-triisopropylbiphenyl (9.12 g, 22.26 mmol), sodium tert-butoxide (0.07 g, 0.74 mmol), and toluene (50 mL) were added to a 100 mL reaction flask, and a resulting mixture was heated to 110° C. under nitrogen protection and then stirred for 5 h under reflux; a resulting reaction solution was cooled to room temperature, dichloromethane and water were added to the reaction solution for extraction, and a resulting organic phase was dried with anhydrous magnesium sulfate and then filtered to obtain a filtrate; the filtrate was passed through a short silica gel column, and the solvent was removed from the filtrate under reduced pressure; and a crude product was purified through recrystallization with a dichloromethane/n-heptane system (1:5) to obtain Intermediate-1-C-1 (3.91 g, yield: 83%).

In the following examples, Intermediate-3-X was synthesized by the same method as the synthesis method of Intermediate-3-A, except that Intermediate-1-X in Table 3 was used instead of Intermediate-1-A, and Compound SM-3 in Table 3 was used instead of phenylamine; where X was B, C, D, E, F, G, H, I, G, K, or L. For example, Compound SM-3 can be phenylamine, o-toluidine, 3-amino-1,1-biphenyl, 2-naphthylamine, 4-fluoroaniline, 4-cyanoaniline, p-toluidine, 3-methylaniline, or 4-amino-1,1-biphenyl, and each Compound SM-3 can lead to a unique Intermediate-3-X correspondingly. For example, the synthesis process can be shown in a reaction equation 3, and the reaction equation 3 can be:

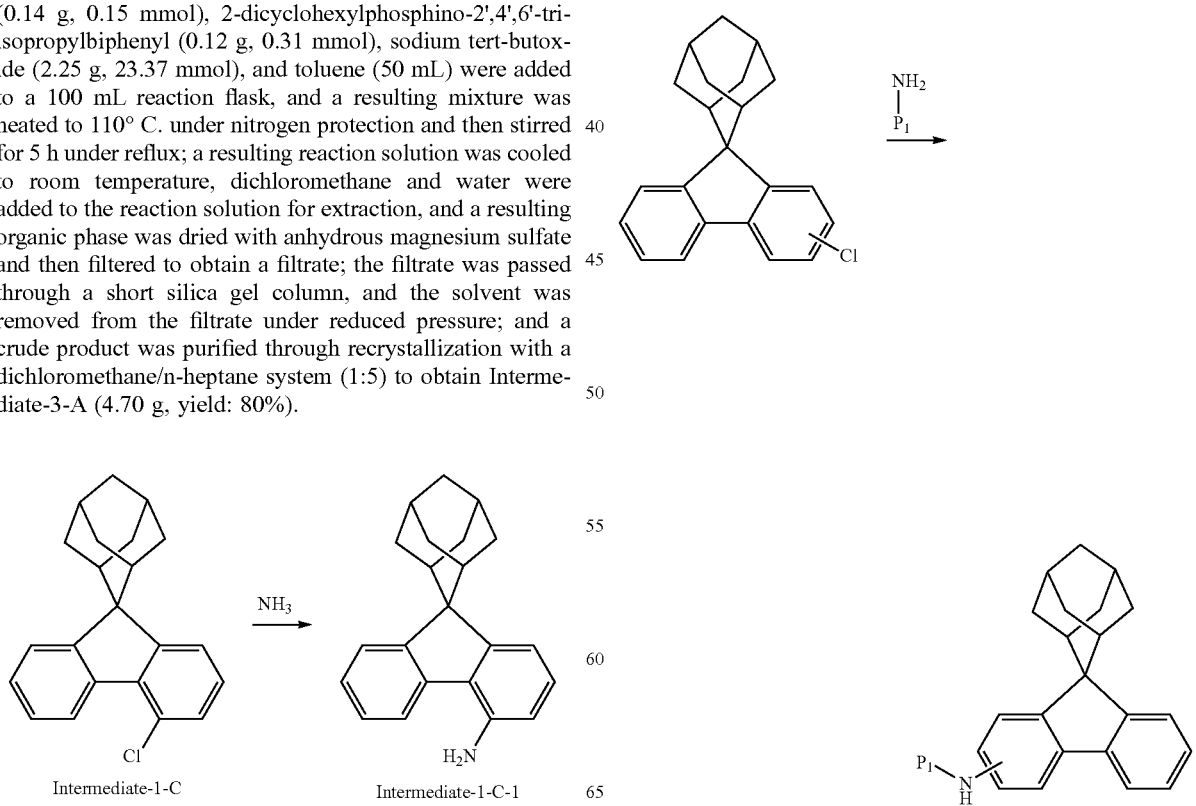

Synthesized Intermediate-3-X was shown in Table 3
TABLE 3
Synthesis List of Intermediate-3-X
| Intermediate-1-X | SM-3 | Intermediate-3-X | Mass (g) | Yield (%) |
|---|---|---|---|---|
| 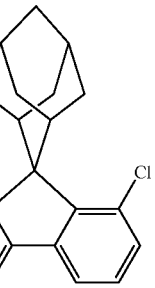<br>Intermediate-1-A | 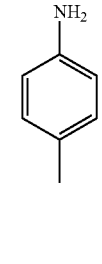 | 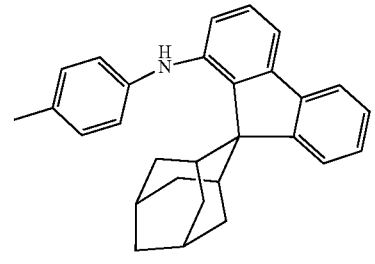<br>Intermediate-3-B | 4.64 | 80 |
| | 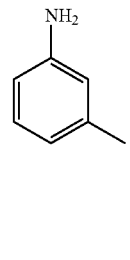 | 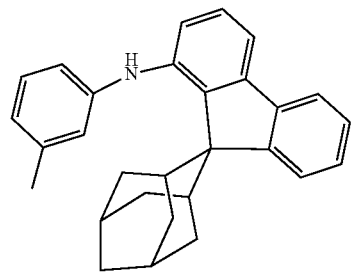<br>Intermediate-3-C | 4.58 | 79 |
| | 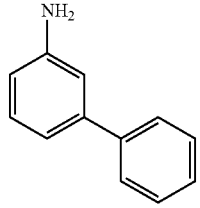 [SMILES: Nc1cccc(-c2ccccc2)c1] | 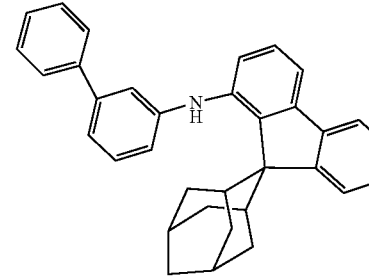<br>Intermediate-3-D | 5.24 | 78 |
| | 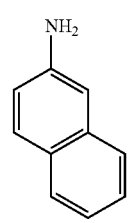 [SMILES: Nc1ccc2ccccc2c1] | 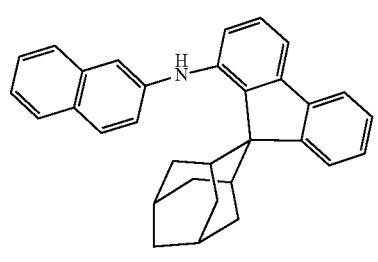<br>Intermediate-3-E | 4.75 | 75 |

TABLE 3-continued

Synthesis List of Intermediate-3-X

| Intermediate-1-X | SM-3 | Intermediate-3-X | Mass (g) | Yield (%) |
|---|---|---|---|---|
| Intermediate-1-B | aniline (NH₂–C₆H₅) | Intermediate-3-F | 4.26 | 76 |
| Intermediate-1-B | 4-fluoroaniline | Intermediate-3-G | 4.33 | 73 |
| Intermediate-1-B | 4-aminobenzonitrile | Intermediate-3-H | 4.53 | 76 |
| Intermediate-1-C | aniline | Intermediate-3-I | 4.20 | 75 |

TABLE 3-continued

Synthesis List of Intermediate-3-X

| Intermediate-1-X | SM-3 | Intermediate-3-X | Mass (g) | Yield (%) |
|---|---|---|---|---|
| | o-toluidine (NH₂, CH₃) | Intermediate-3-J | 4.18 | 72 |
| | 4-aminobiphenyl | Intermediate-3-K | 4.77 | 71 |
| | 2-aminonaphthalene | Intermediate-3-L | 4.62 | 73 |

TABLE 3-continued

Synthesis List of Intermediate-3-X

| Intermediate-1-X | SM-3 | Intermediate-3-X | Mass (g) | Yield (%) |
| --- | --- | --- | --- | --- |
| Intermediate-1-C-1 | | Intermediate-3-M | 4.35 | 70 |
| Intermediate-1-D | | Intermediate-3-N | 4.31 | 71 |
| | | Intermediate-3-O | 4.25 | 70 |

Synthesis of Compound 107

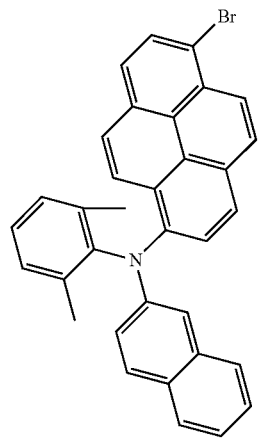

Intermediate-2-H

+

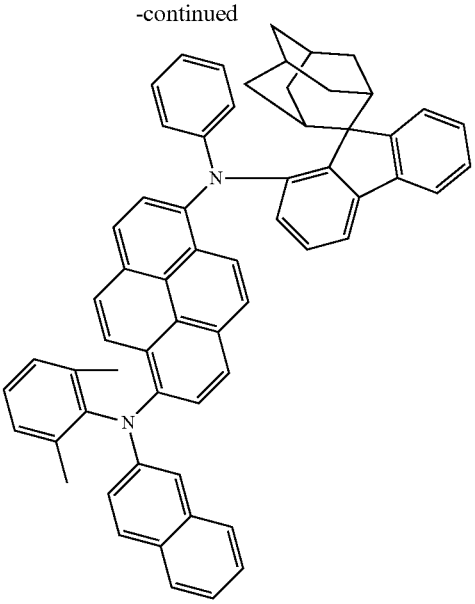

Compound 107

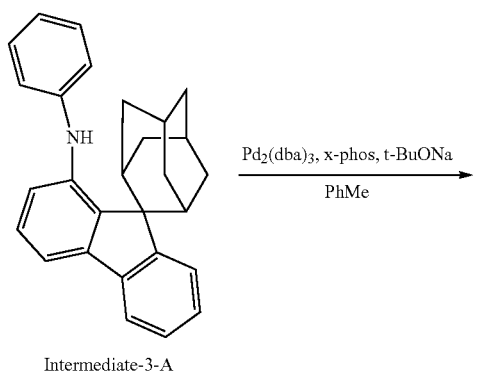

Intermediate-3-A

Intermediate-2-H (5.0 g, 9.49 mmol), Intermediate-3-A (3.59 g, 9.49 mmol), tris(dibenzylideneacetone)dipalladium (0.08 g, 0.095 mmol), 2-dicyclohexylphosphino-2',4',6'-triisopropylbiphenyl (0.07 g, 0.18 mmol), sodium tert-butoxide (1.37 g, 14.24 mmol), and toluene (50 mL) were added to a 100 mL reaction flask, and a resulting mixture was heated to 110° C. under nitrogen protection and then stirred for 10 h under reflux; a resulting reaction solution was cooled to room temperature, dichloromethane and water were added to the reaction solution for extraction, and a resulting organic phase was dried with anhydrous magnesium sulfate and then filtered to obtain a filtrate; the filtrate was passed through a short silica gel column, and the solvent was removed from the filtrate under reduced pressure; and a crude product was purified through recrystallization with a dichloromethane/n-heptane system (1:3) to obtain Compound 107 (6.16 g, yield: 79%), m/z=823.4[M+H]$^+$.

In the following examples, Compound X was synthesized by the same method as the synthesis method of Compound 107, except that Intermediate-2-X was used instead of Intermediate-2-H, and Intermediate-3-X was used instead of Intermediate-3-A. For example, Intermediate-2-X can be Intermediate-2-A, Intermediate-2-B, Intermediate-2-C, Intermediate-2-D, and the like; and Intermediate-3-X can be Intermediate-3-B, Intermediate-3-C, Intermediate-3-D, and the like, from which a unique Compound X can be prepared correspondingly. The number, structure, raw material, last-step synthesis yield, and characterization data for specific compounds were shown in Table 4.

TABLE 4
Structure, Preparation, and Characterization data of Compound
| Intermediate-3-X | Intermediate-2-X | Compound X | Mass (g) | Yield (%) | MS [M + H]+ |
|---|---|---|---|---|---|
| 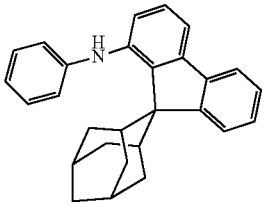<br>Intermediate-3-A | 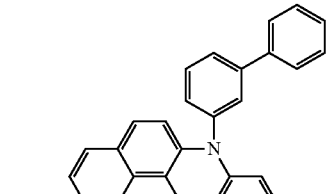<br>Intermediate-2-B | 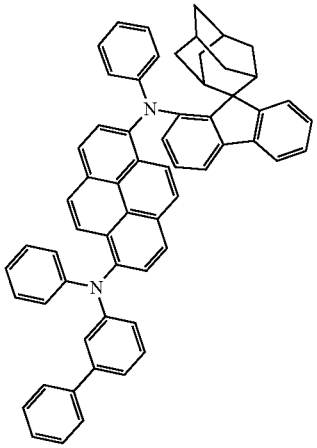<br>122 | 8.15 | 75 | 821.4 |
| | 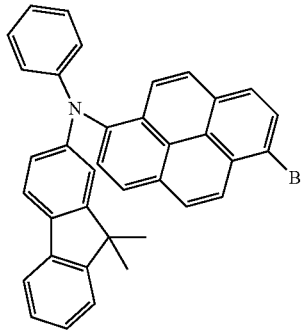<br>Intermediate-2-C | 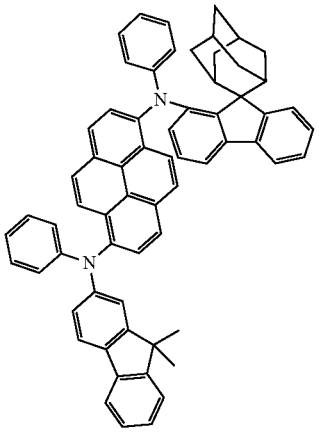<br>124 | 8.43 | 74 | 861.4 |
| | 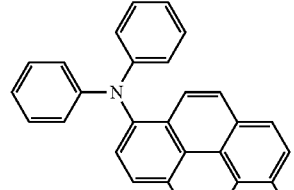<br>Intermediate-2-A | 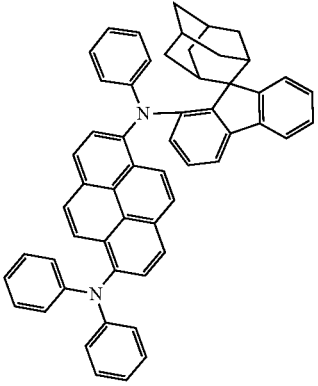<br>125 | 7.59 | 77 | 745.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| | Intermediate-2-I | 126 | 7.67 | 73 | 795.4 |
| Intermediate-3-B | Intermediate-2-A | 106 | 7.36 | 76 | 759.4 |
| Intermediate-3-C | Intermediate-2-D | 108 | 7.43 | 72 | 809.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| Intermediate-3-D | Intermediate-2-A | 121 | 6.69 | 74 | 821.4 |
| Intermediate-3-E | Intermediate-2-A | 128 | 6.96 | 75 | 795.4 |
| Intermediate-3-F | Intermediate-2-G | 36 | 8.9 | 71 | 947.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| | Intermediate-2-F | 28 | 8.55 | 72 | 897.4 |
| Intermediate-3-G | Intermediate-2-A | 116 | 6.94 | 72 | 763.3 |
| Intermediate-3-H | Intermediate-2-A | 117 | 7.17 | 75 | 770.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| Intermediate-3-I | Intermediate-2-B | 1 | 7.71 | 71 | 821.4 |
| | Intermediate-2-C | 3 | 7.98 | 70 | 861.4 |
| | Intermediate-2-A | 4 | 7.39 | 75 | 745.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| Intermediate-3-J | Intermediate-2-E | 79 | 7.20 | 73 | 773.4 |
| Intermediate-3-K | Intermediate-2-A | 82 | 6.60 | 73 | 821.4 |
| Intermediate-3-L | Intermediate-2-A | 83 | 6.78 | 73 | 795.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| Intermediate-3-I | Intermediate-2-J | 8 | 6.63 | 70 | 851.3 |
| | Intermediate-2-K | 7 | 6.16 | 70 | 835.4 |
| Intermediate-3-M | Intermediate-2-K | 133 | 7.35 | 70 | 1043.4 |

TABLE 4-continued

Structure, Preparation, and Characterization data of Compound

| Intermediate-3-X | Intermediate-2-X | Compound X | Mass (g) | Yield (%) | MS [M + H]+ |
|---|---|---|---|---|---|
| 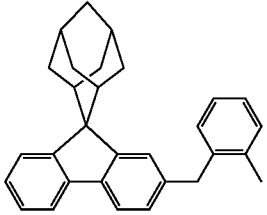
Intermediate-3-N | 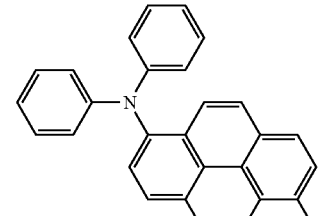
Intermediate-2-A | 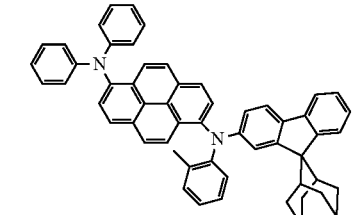
134 | 6.03 | 75 | 775.4 |
| 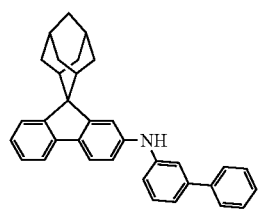
Intermediate-3-O | 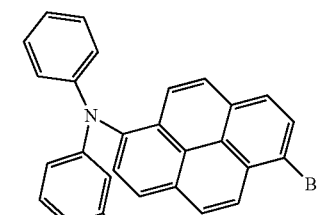
Intermediate-2-C | 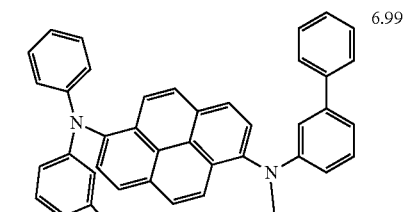
135 | 6.99 | 73 | 953.3 |

NMR data of Compound 1:

$^1$H NMR (400 Hz, CD$_2$Cl$_2$): 8.20 (d, 1H), 7.95 (d, 1H), 7.81-7.72 (m, 4H), 7.58-7.48 (m, 5H), 7.46-7.39 (m, 2H), 7.34-7.21 (m, 8H), 7.18 (d, 1H), 7.15-7.08 (m, 1H), 7.6(d, 1H), 6.99 (s, 1H), 6.93 (d, 1H), 6.91-6.89 (m, 7H), 6.87 (d, 1H), 2.84 (d, 2H), 2.76 (d, 2H), 2.16 (s, 1H), 2.13 (s, 1H), 1.96 (s, 2H), 1.75 (t, 4H), 1.46 (s, 2H).

NMR data of Compound 36:

$^1$H NMR (400 Hz, CD$_2$Cl$_2$): 8.21 (d, 2H), 7.90 (d, 1H), 7.80-7.73 (m, 6H), 7.68 (d, 1H), 7.56-7.47 (m, 6H), 7.43-7.36 (m, 7H), 7.27-7.20 (m, 5H), 7.19-7.13 (m, 3H), 7.08 (d, 1H), 7.03 (d, 2H), 6.99-6.93 (m, 4H), 6.90 (d, 2H), 2.83 (d, 2H), 2.74 (d, 2H), 2.16 (s, 1H), 2.13 (s, 1H), 1.96 (s, 2H), 1.75 (t, 4H), 1.46 (s, 2H).

Production and Evaluation of Organic Electroluminescent Device

Example 1

A blue organic electroluminescent device was produced by the following method.

An ITO substrate (manufactured by Corning) with a thickness of 1,500 Å was cut into a size of 40 mm (length)× 40 mm (width)×0.7 mm (thickness), then the substrate was processed through photolithography into an experimental substrate with a cathode, an anode, and insulating layer patterns, and the experimental substrate was subjected to a surface treatment with ultraviolet (UV)-ozone and O$_2$:N$_2$ plasma to increase a work function of the anode (experimental substrate) and remove scums.

4,4',4"-tris(N-3-methylphenyl-N-phenylamino)triphenylamine(m-MTDATA) was vacuum deposited on the experimental substrate (anode) to form an hole injection layer (HIL) with a thickness of 100 Å, and then the Compound NPB was vacuum-deposited on the hole injection layer to form an hole transport layer with a thickness of 1,000 Å.

The compound 4,4',4"-tris(carbazol-9-yl)-triphenylamine (TCTA) was vacuum deposited on the hole transport layer to form an electron blocking layer (EBL) with a thickness of 100 Å. α,β-ADN as a host material and a doped compound 1 as a guest material were vacuum deposited in a film thickness ratio of 20:1 to form an organic electroluminescent layer (EML) with a thickness of 220 Å.

4,7-diphenyl-2,9-bis(4-(1-phenyl-1H-benzo[d]imidazol-2-yl)phenyl)-1,10-phenanthroline (DBimiBphen) and 8-hydroxyquinolinolato-lithium (LiQ) were vacuum deposited in a film thickness ratio of 1:1 to form an electron transport layer (ETL) with a thickness of 300 Å, then LiQ was vacuum deposited on the electron transport layer to form an electron injection layer (EIL) with a thickness of 10 Å, and then magnesium (Mg) and silver (Ag) were vacuum deposited in a film thickness ratio of 1:9 on the electron injection layer to form a cathode with a thickness of 120 Å.

In addition, CP-1 was vacuum deposited on the cathode to form an organic capping layer (CPL) with a thickness of 650 Å, thereby completing the production of the organic electroluminescent device.

During the production of the blue organic electroluminescent device, structures of materials used were as follows:

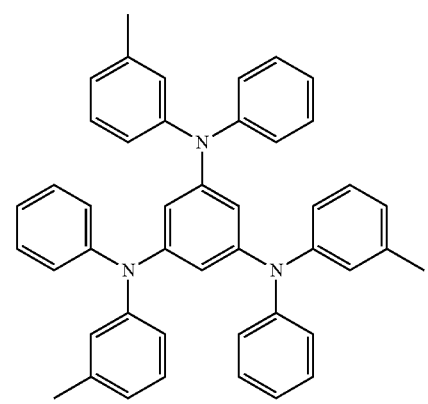

m-MTDATA

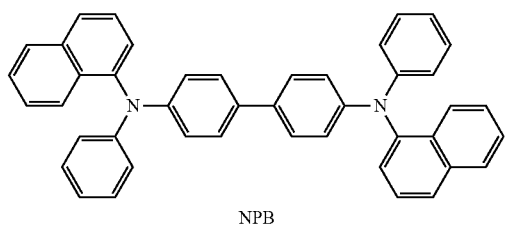

NPB

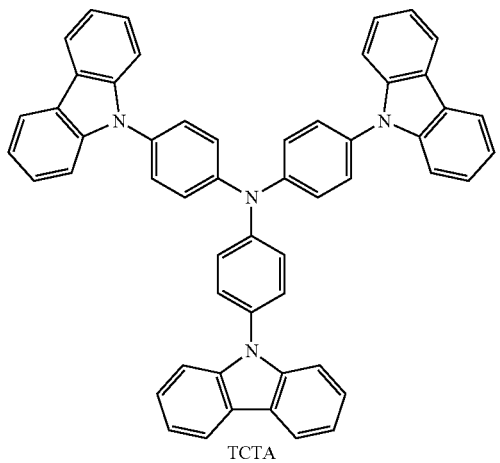

TCTA

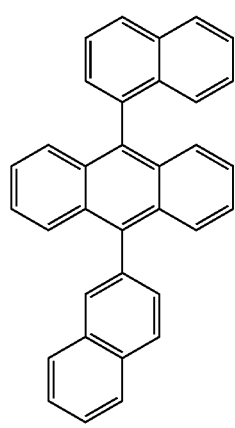

α,β-ADN

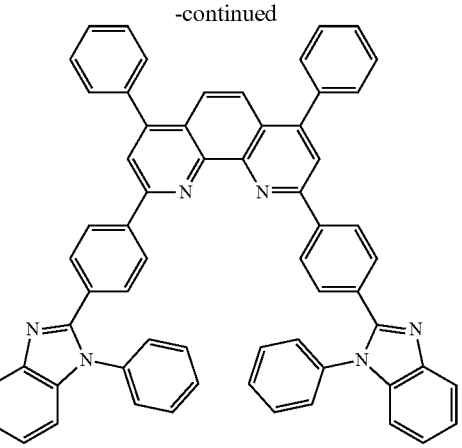

DBimiBphen

LiQ

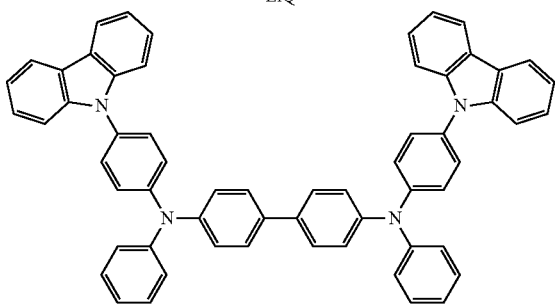

CP-1

Examples 2 to 24

Blue organic electroluminescent devices were produced by the same method as Example 1, except that compounds 3, 4, 7, 8, 28, 36, 79, 82, 83, 106, 107, 108, 116, 117, 121, 122, 124, 125, 126, 128, 133, 134, or 135 was each used instead of Compound 1 co-deposited with α,β-ADN of the organic electroluminescent layer in Example 1.

Comparative Example 1

A blue organic electroluminescent device was produced by the same method as Example 1, except that Compound A was used instead of Compound 1 co-deposited with α,β-ADN of the organic electroluminescent layer in Example 1.

Comparative Example 2

A blue organic electroluminescent device was produced by the same method as Example 1, except that Compound B was used instead of Compound 1 co-deposited with α,β-ADN of the organic electroluminescent layer in Example 1.

Comparative Example 3

A blue organic electroluminescent device was produced by the same method as Example 1, except that Compound C was used instead of Compound 1 co-deposited with α,β-ADN of the organic electroluminescent layer in Example 1.

Comparative Example 4

A blue organic electroluminescent device was produced by the same method as Example 1, except that Compound D was used instead of Compound 1 co-deposited with α,β-ADN of the organic electroluminescent layer in Example 1.

Structures of Compound A, Compound B, Compound C, and Compound D were as follows:

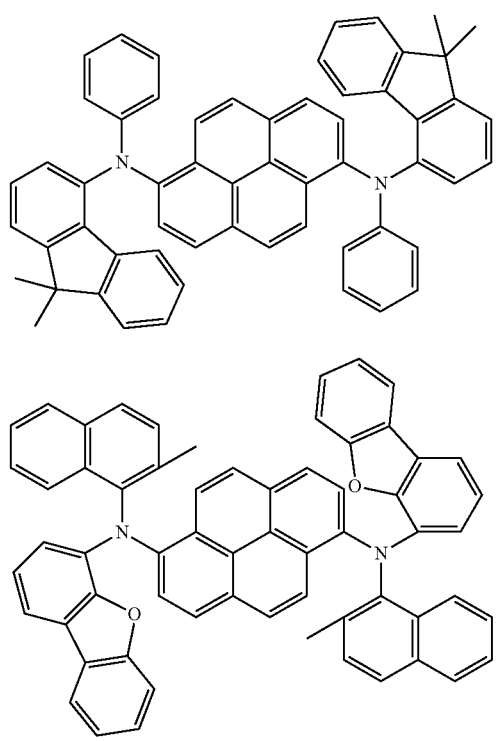

A

B

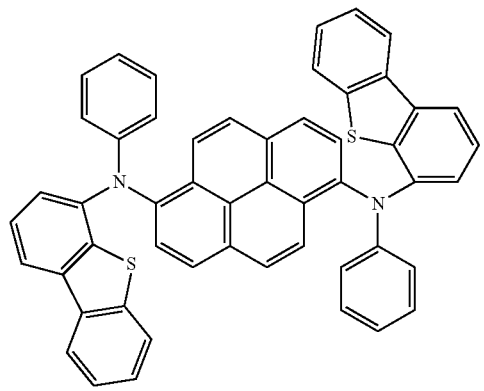

C

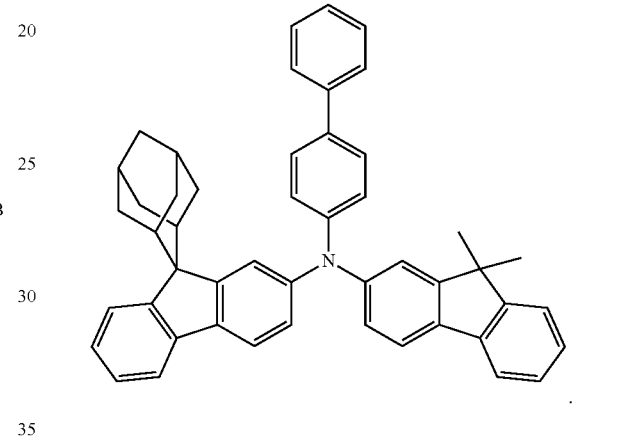

D

The blue organic electroluminescent devices produced in Examples 2 to 24 and Comparative Examples 1 to 3 were subjected to a performance test. The IVL (current, voltage, and luminance) data were test results at 10 mA/cm$^2$, and the life span was a test result at a current density of 15 mA/cm$^2$. Specific results were shown in Table 5

TABLE 5

Performance test results of the blue organic electroluminescent elements

| Example No. | Compound | Driving voltage (V) | Luminous efficiency (Cd/A) | External quantum efficiency (EQE) (%) | Chromaticity coordinate CIEy | T95 life span (h) |
|---|---|---|---|---|---|---|
| Example 1 | Compound 1 | 3.89 | 6.8 | 13.5 | 0.047 | 206 |
| Example 2 | Compound 3 | 3.89 | 6.6 | 14.0 | 0.047 | 204 |
| Example 3 | Compound 4 | 3.84 | 6.6 | 13.5 | 0.047 | 209 |
| Example 4 | Compound 7 | 3.90 | 6.7 | 13.7 | 0.047 | 200 |
| Example 5 | Compound 8 | 3.87 | 6.7 | 13.4 | 0.047 | 209 |
| Example 6 | Compound 28 | 3.94 | 6.2 | 12.8 | 0.047 | 176 |
| Example 7 | Compound 36 | 3.98 | 6.4 | 13.1 | 0.047 | 187 |
| Example 8 | Compound 79 | 3.82 | 6.6 | 13.5 | 0.047 | 198 |
| Example 9 | Compound 82 | 3.85 | 6.7 | 13.7 | 0.047 | 217 |
| Example 10 | Compound 83 | 3.89 | 6.8 | 13.8 | 0.047 | 205 |
| Example 11 | Compound 106 | 3.90 | 6.5 | 13.8 | 0.047 | 201 |
| Example 12 | Compound 107 | 3.81 | 6.8 | 13.7 | 0.047 | 216 |
| Example 13 | Compound 108 | 3.82 | 6.8 | 13.9 | 0.047 | 214 |
| Example 14 | Compound 116 | 3.97 | 6.2 | 12.8 | 0.047 | 178 |
| Example 15 | Compound 117 | 3.94 | 6.4 | 13.1 | 0.047 | 173 |
| Example 16 | Compound 121 | 3.80 | 6.6 | 13.9 | 0.047 | 211 |
| Example 17 | Compound 122 | 3.83 | 6.5 | 14.0 | 0.047 | 205 |
| Example 18 | Compound 124 | 3.82 | 6.7 | 13.7 | 0.047 | 229 |
| Example 19 | Compound 125 | 3.90 | 6.5 | 13.5 | 0.047 | 216 |

TABLE 5-continued

Performance test results of the blue organic electroluminescent elements

| Example No. | Compound | Driving voltage (V) | Luminous efficiency (Cd/A) | External quantum efficiency (EQE) (%) | Chromaticity coordinate CIEy | T95 life span (h) |
|---|---|---|---|---|---|---|
| Example 20 | Compound 126 | 3.90 | 6.8 | 13.9 | 0.047 | 200 |
| Example 21 | Compound 128 | 3.89 | 6.7 | 13.6 | 0.047 | 205 |
| Example 22 | Compound 133 | 3.8 | 6.7 | 13.8 | 0.047 | 220 |
| Example 23 | Compound 134 | 3.98 | 6.4 | 13.1 | 0.047 | 184 |
| Example 24 | Compound 135 | 3.96 | 6.2 | 12.8 | 0.047 | 175 |
| Comparative Example 1 | Compound A | 4.25 | 4.3 | 8.9 | 0.047 | 132 |
| Comparative Example 2 | Compound B | 4.17 | 4.9 | 10.1 | 0.047 | 138 |
| Comparative Example 3 | Compound C | 4.28 | 4.6 | 9.5 | 0.047 | 146 |
| Comparative Example 4 | Compound D | 4.2 | 4.8 | 9.9 | 0.047 | 125 |

According to the above table, compared with the blue organic electroluminescent device produced in Comparative Example 1, the blue organic electroluminescent devices produced in Examples 1 to 24 have a driving voltage reduced by at least 0.27 V, a luminous efficiency increased by at least 44.9%, an external quantum efficiency increased by at least 43.8%, and a life span increased by at least 31.10%; compared with the blue organic electroluminescent device produced in Comparative Example 2, the blue organic electroluminescent devices produced in Examples 1 to 24 have a driving voltage reduced by at least 0.19 V, a luminous efficiency increased by at least 27.1%, an external quantum efficiency increased by at least 26.7%, and a life span increased by at least 25.4%; compared with the blue organic electroluminescent device produced in Comparative Example 3, the blue organic electroluminescent devices produced in Examples 1 to 24 have a driving voltage reduced by at least 0.30 V, a luminous efficiency increased by at least 35.4%, an external quantum efficiency increased by at least 34.7%, and a life span increased by at least 18.5%; and compared with the blue organic electroluminescent device produced in Comparative Example 4, the blue organic electroluminescent devices produced in Examples 1 to 24 have a driving voltage reduced by at least 0.22 V, a luminous efficiency increased by at least 29.8%, an external quantum efficiency increased by at least 29.3%, and a life span increased by at least 38.4%. Among Examples 1 to 24, organic electroluminescent devices obtained by the compounds with substituents at positions 1 and 4 (Examples 1 to 5, 8 to 13, and 16 to 22) show better performance than organic electroluminescent devices obtained by the compounds with substituents at positions 2 and 3 (Examples 6 to 7, 14 to 15, and 23 to 24), where for tested organic electroluminescent devices, an average voltage difference is 0.10 V, an average luminous efficiency difference is 0.4 Cd/A, an average external quantum efficiency difference is 0.7%, and an average life span difference is 30 h. Therefore, the nitrogen-containing compound of the present disclosure can be used as a guest material in the organic electroluminescent layer to produce a blue organic electroluminescent device with high luminous efficiency and long span life, and compounds with substituents at positions 1 and 4 are preferred for the organic electroluminescent device production.

The nitrogen-containing compound of the present disclosure includes pyrenyl and spiro(adamantyl-fluorenyl). The pyrenyl has a large rigid conjugated structure, strong chemical stability, blue light emission, high fluorescence quantum efficiency and other excellent fluorescence properties, and high thermal stability. In the present disclosure, in order to avoid the aggregation of pyrenyl, pyrenyl is modified with large groups to avoid π-aggregation or exciplex resulting from the direct accumulation of conjugate planes through steric hindrance. An arylamine compound with spiro(adamantyl-fluorenyl) has a large molecular weight, which can effectively increase a glass transition temperature of the nitrogen-containing compound. Moreover, a structure of the arylamine compound has large steric hindrance, which makes the nitrogen-containing compound difficult to crystallize or agglomerate, such that the nitrogen-containing compound has a long life span in the organic electroluminescent device. The nitrogen atom on the arylamine has a strong electron-donating ability, and can improve the hole mobility, such that electrons and holes move rapidly to a recombination region and recombine for light emission, and finally reach a dynamic balance, thereby the efficiency of the organic electroluminescent device is improved.

What is claimed is:

1. A nitrogen-containing compound having a structure shown in Chemical formula 1:

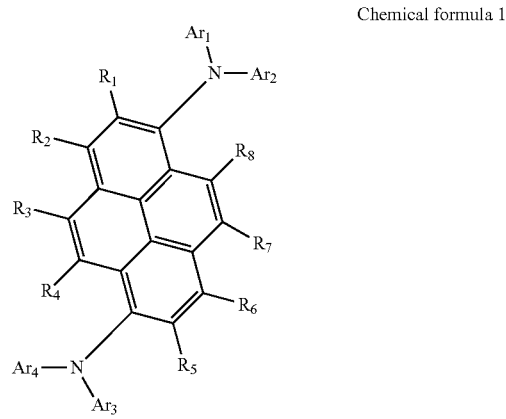

Chemical formula 1 wherein, $Ar_3$ and $Ar_4$ are the same or different, and are respectively independently selected from: a substituted or unsubstituted aryl with 6 to 30 carbon atoms, or a substituted or unsubstituted heteroaryl with 3 to 30 carbon atoms; and $Ar_1$ and $Ar_2$ are the same or different, and are respectively independently selected from: a substituted or unsubstituted aryl with 6 to 30 carbon atoms, or a substituted or unsubstituted heteroaryl with 3 to 30 carbon atoms, or

141

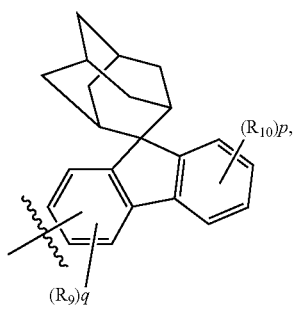

wherein,

represents a chemical bond;
- p is selected from: 1, 2, 3, or 4, and when p is greater than or equal to 2, any two $R_{10}$ groups are the same or different; and
- q is selected from: 1, 2, or 3, and when q is greater than or equal to 2, any two $R_9$ groups are the same or different; and
- $R_1$ to $R_{10}$ are the same or different, and are respectively independently selected from: hydrogen, deuterium, an unsubstituted alkyl with 1 to 5 carbon atoms;
- substituents of $Ar_1$, $Ar_2$, $Ar_3$, and $Ar_4$ are the same or different, and are respectively independently selected from: deuterium, cyano, a halogen, a linear alkyl with 1 to 3 carbon atoms, a branched alkyl with 3 to 7 carbon atoms, an aryl with 6 to 18 carbon atoms, or a heteroaryl with 3 to 18 carbon atoms

142

2. The nitrogen-containing compound according to claim 1, wherein $R_2$ and $R_6$ are not hydrogen, and $R_1$, $R_3$, $R_4$, $R_5$, $R_7$, $R_8$, $R_9$, and $R_{10}$ are all hydrogen.

3. The nitrogen-containing compound according to claim 1, wherein $Ar_3$ and $Ar_4$ are the same or different, and are respectively independently selected from a substituted or unsubstituted aryl with 6 to 25 carbon atoms; $Ar_1$ and $Ar_2$ are the same or different, and are respectively independently selected from: a substituted or unsubstituted aryl with 6 to 25 carbon atoms; or

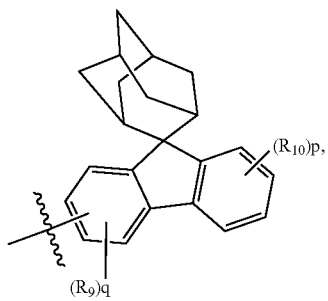

- p is selected from: 1, 2, 3, or 4, and when p is greater than or equal to 2, the any two $R_{10}$ groups are the same or different; and
- q is selected from: 1, 2, or 3, and when q is greater than or equal to 2, the any two $R_9$ groups are the same or different; and
- $R_9$ and $R_{10}$ are the same or different, and are respectively independently selected from: hydrogen or deuterium.

4. The nitrogen-containing compound according to claim 1, wherein $Ar_1$ and $Ar_2$ are respectively independently selected from a group consisting of the following groups:

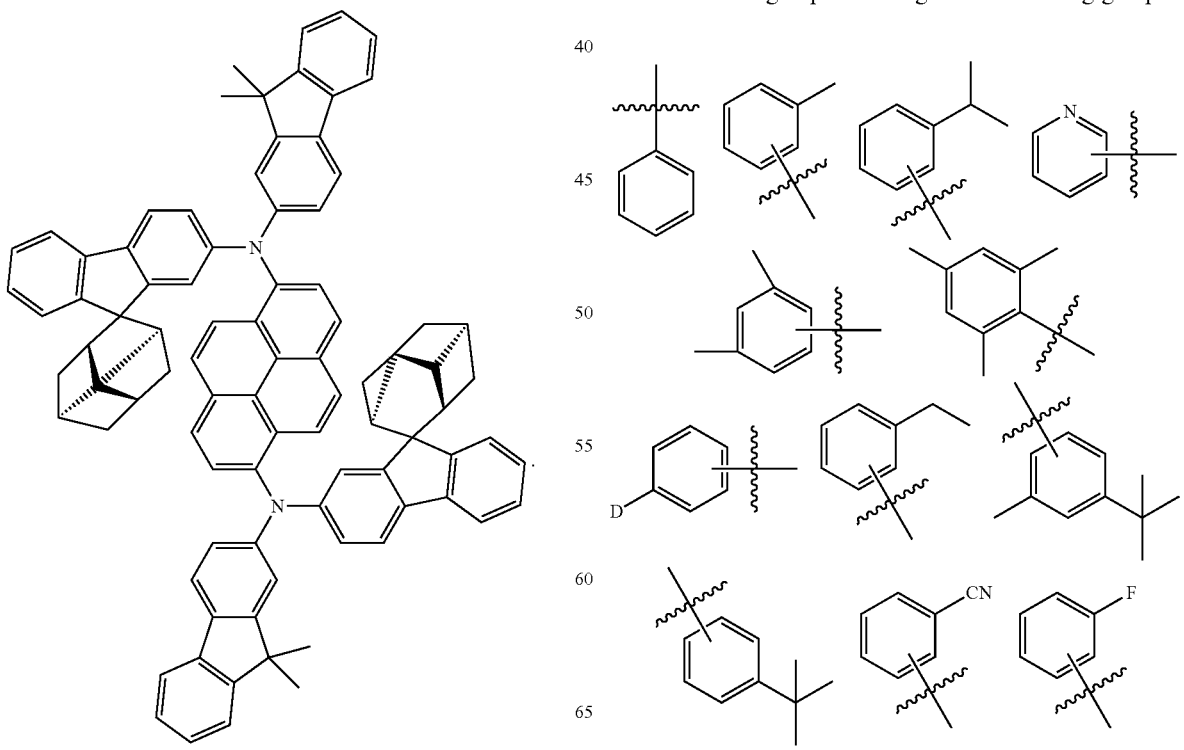

-continued
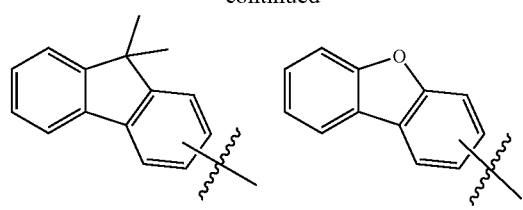
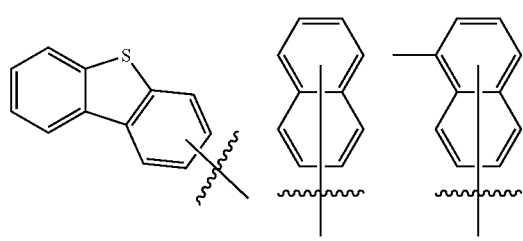
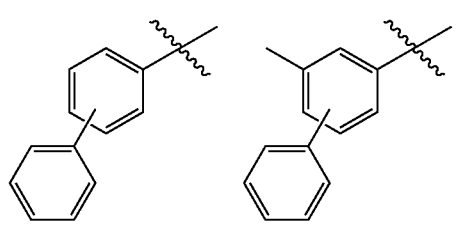
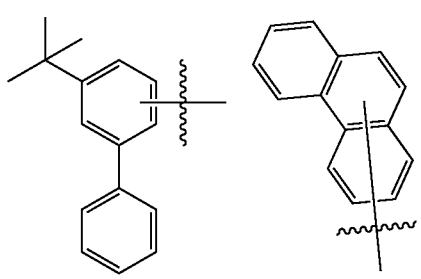
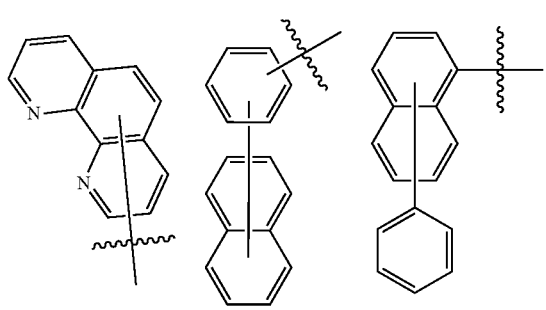
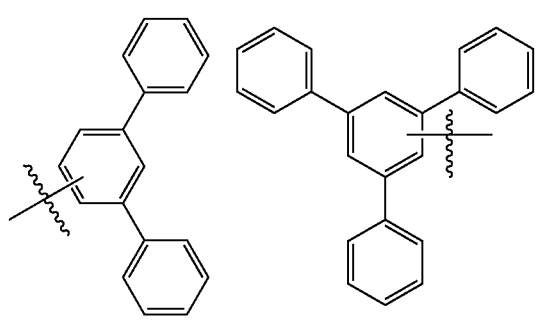
-continued
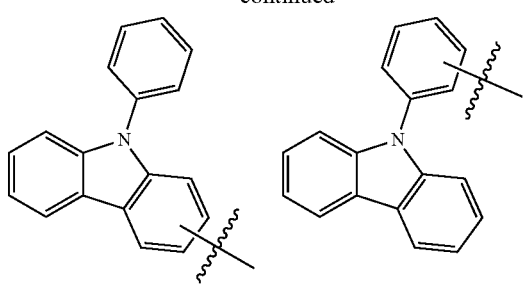
and
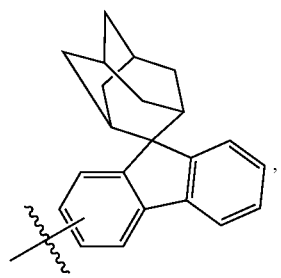
and at least one of Ar$_1$ and Ar$_2$ is
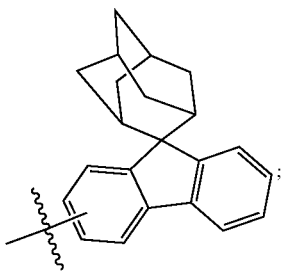
;
wherein Ar$_3$ and Ar$_4$ are respectively independently selected from a group consisting of the following groups:
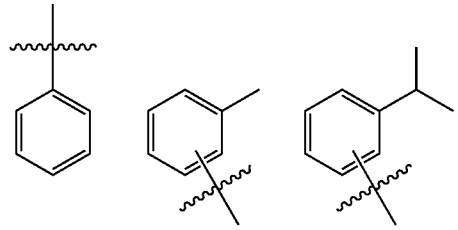
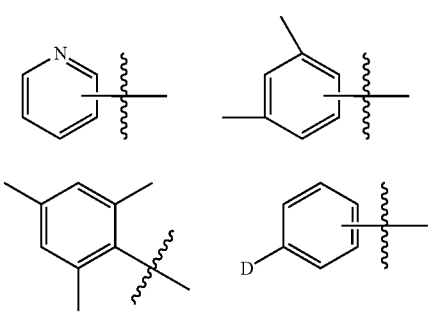

145
-continued

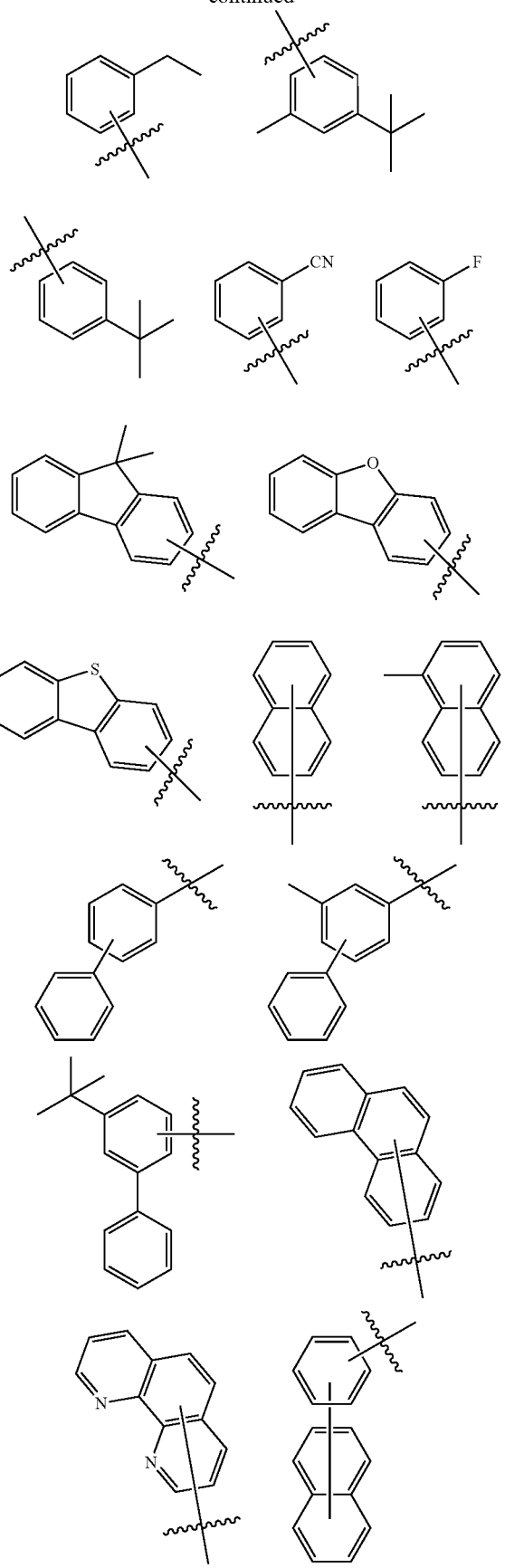

146
-continued

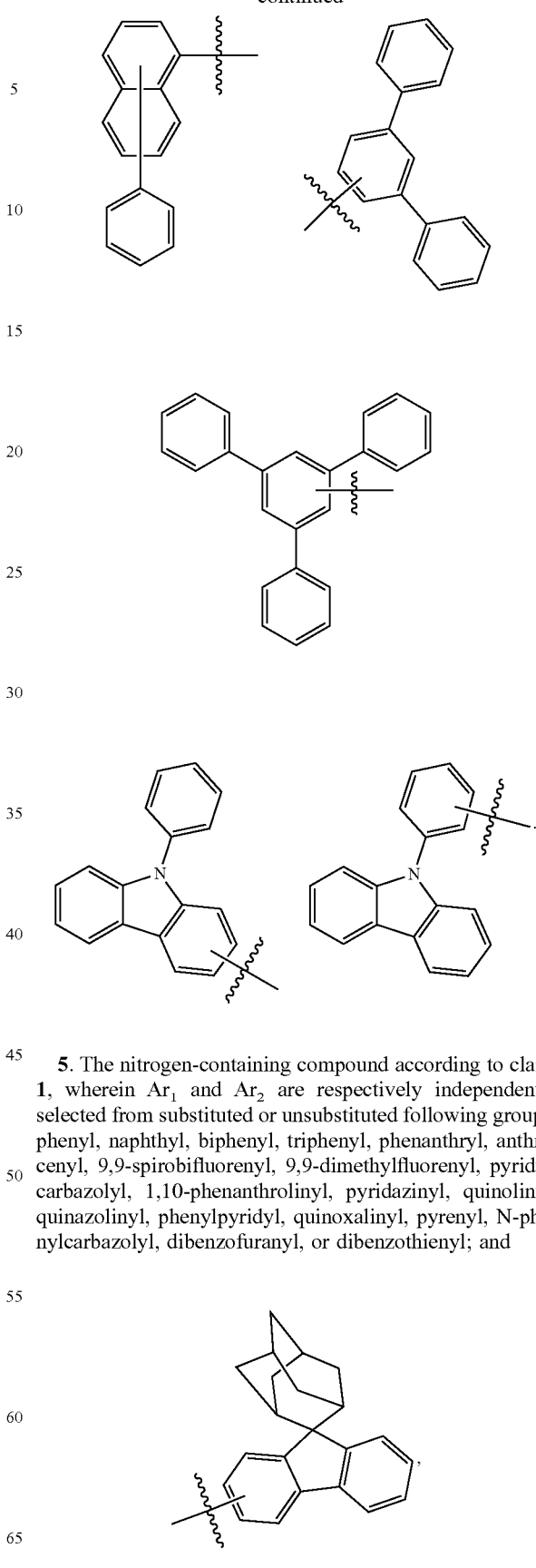

5. The nitrogen-containing compound according to claim 1, wherein Ar₁ and Ar₂ are respectively independently selected from substituted or unsubstituted following groups: phenyl, naphthyl, biphenyl, triphenyl, phenanthryl, anthracenyl, 9,9-spirobifluorenyl, 9,9-dimethylfluorenyl, pyridyl, carbazolyl, 1,10-phenanthrolinyl, pyridazinyl, quinolinyl, quinazolinyl, phenylpyridyl, quinoxalinyl, pyrenyl, N-phenylcarbazolyl, dibenzofuranyl, or dibenzothienyl; and and at least one of Ar₁ and Ar₂ is

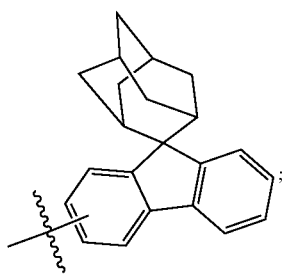

wherein Ar₃ and Ar₄ are respectively independently selected from substituted or unsubstituted following groups: phenyl, naphthyl, biphenyl, triphenyl, phenanthryl, anthracenyl, 9,9-spirobifluorenyl, 9,9-dimethylfluorenyl, pyridyl, carbazolyl, 1,10-phenanthrolinyl, pyridazinyl, quinolinyl, quinazolinyl, phenylpyridyl, quinoxalinyl, pyrenyl, N-phenylcarbazolyl, dibenzofuranyl, or dibenzothienyl; and substituents of the groups are selected from: deuterium, fluorine, chlorine, cyano, methyl, ethyl, isopropyl, tert-butyl, phenyl, naphthyl, pyridyl, dibenzofuranyl, carbazolyl, or dibenzothienyl; and when there are a plurality of substituents, the plurality of substituents are the same or different.

6. The nitrogen-containing compound according to claim 1, wherein the nitrogen-containing compound is selected from a group consisting of the following compounds:

1

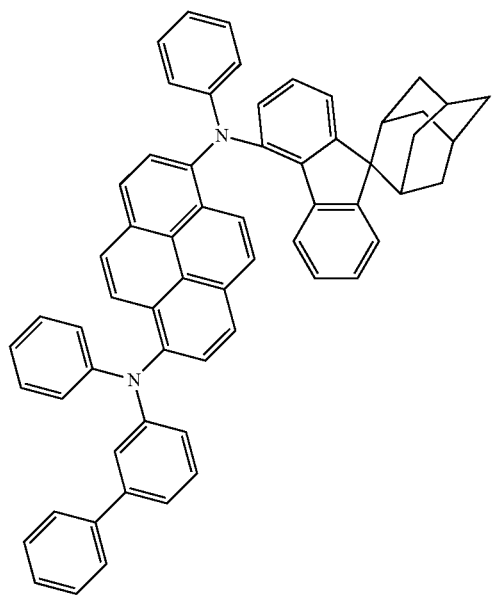

3

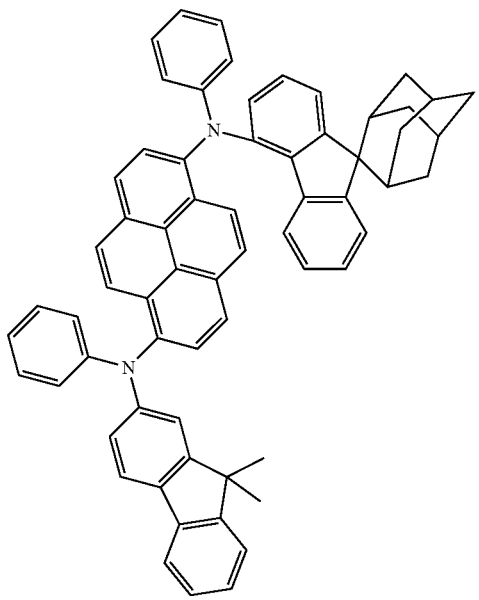

4

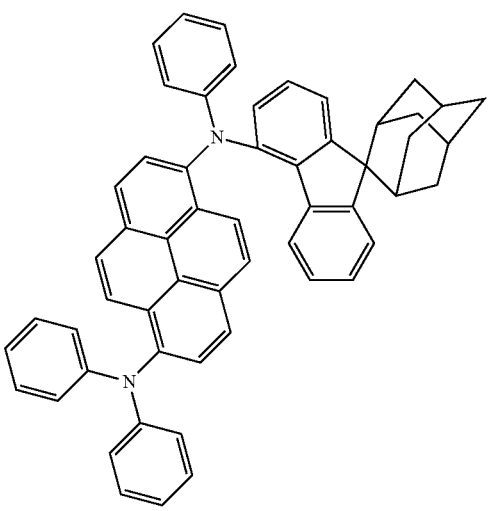

5

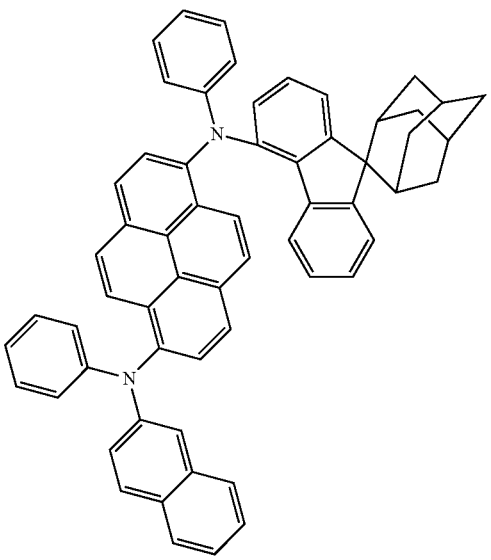

149
-continued
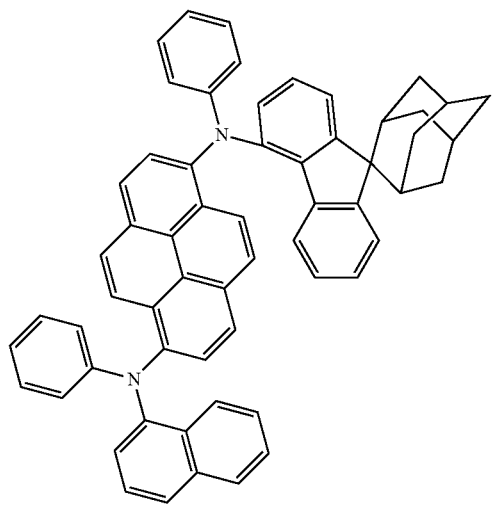
150
-continued
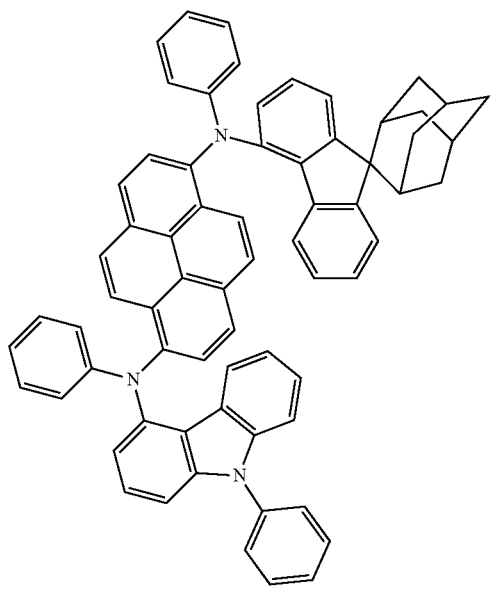
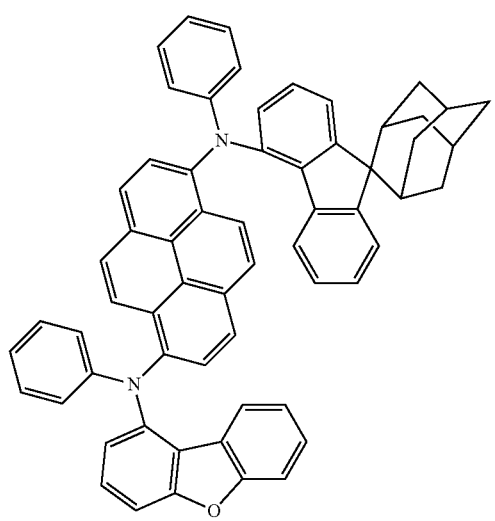
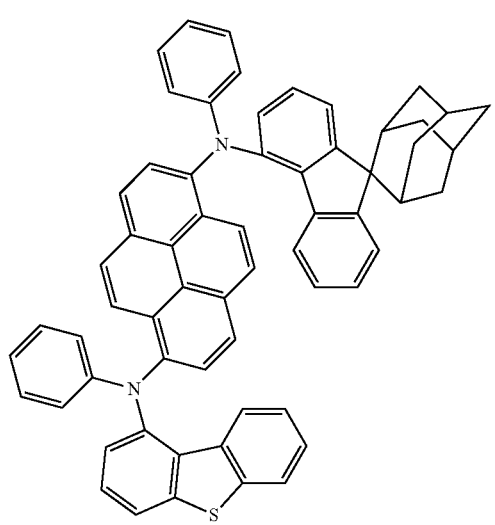
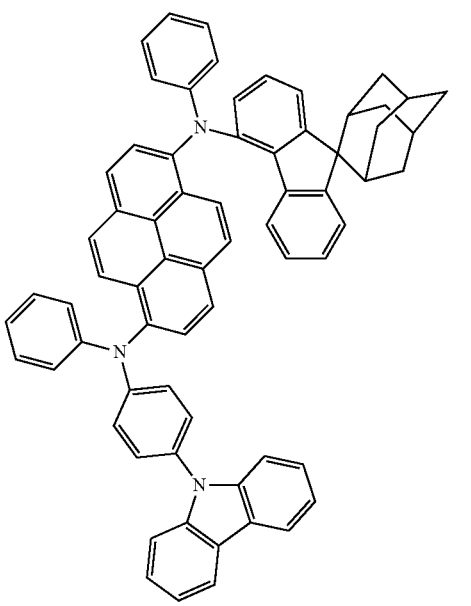

151
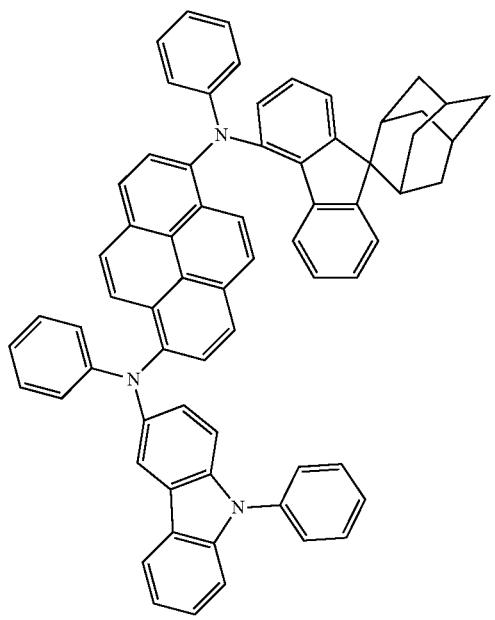
11
152
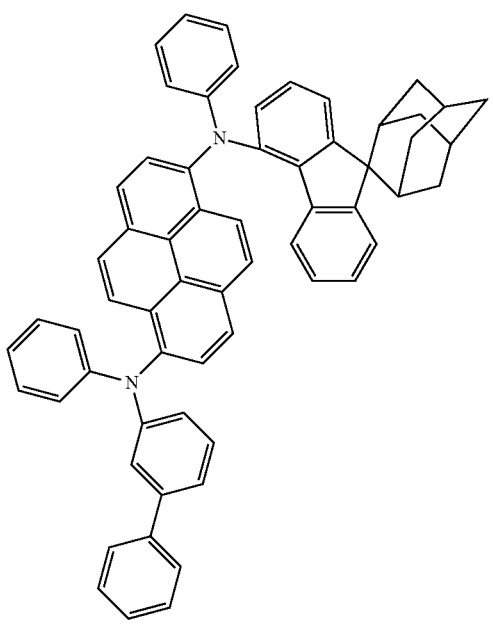
13
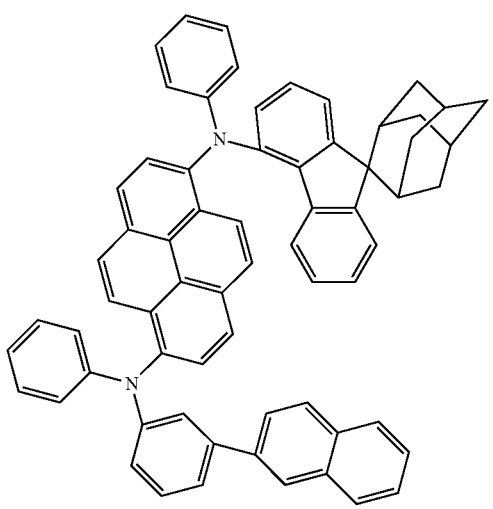
14
12
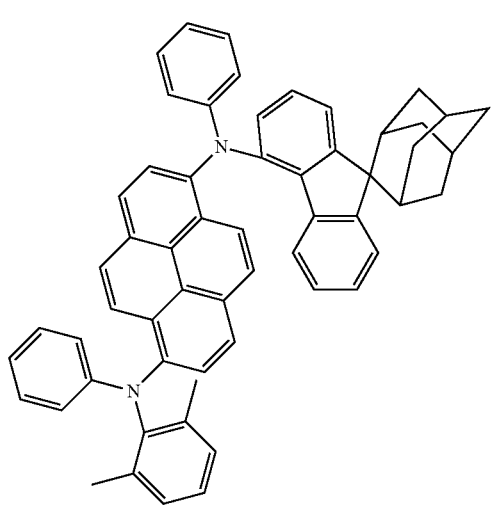
15

153
-continued
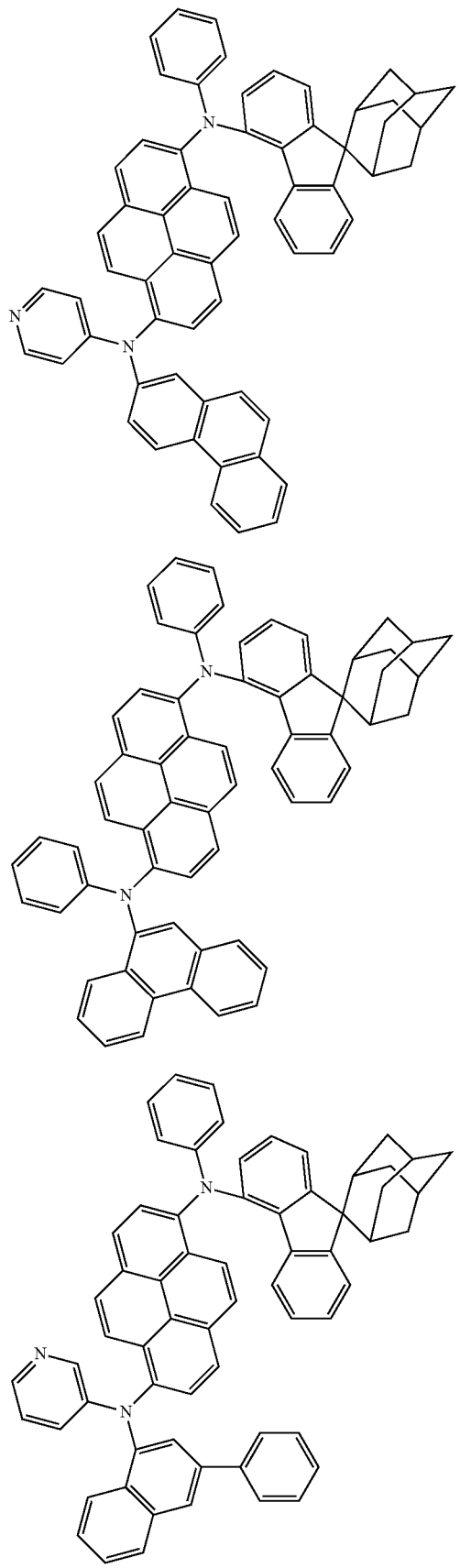
154
-continued
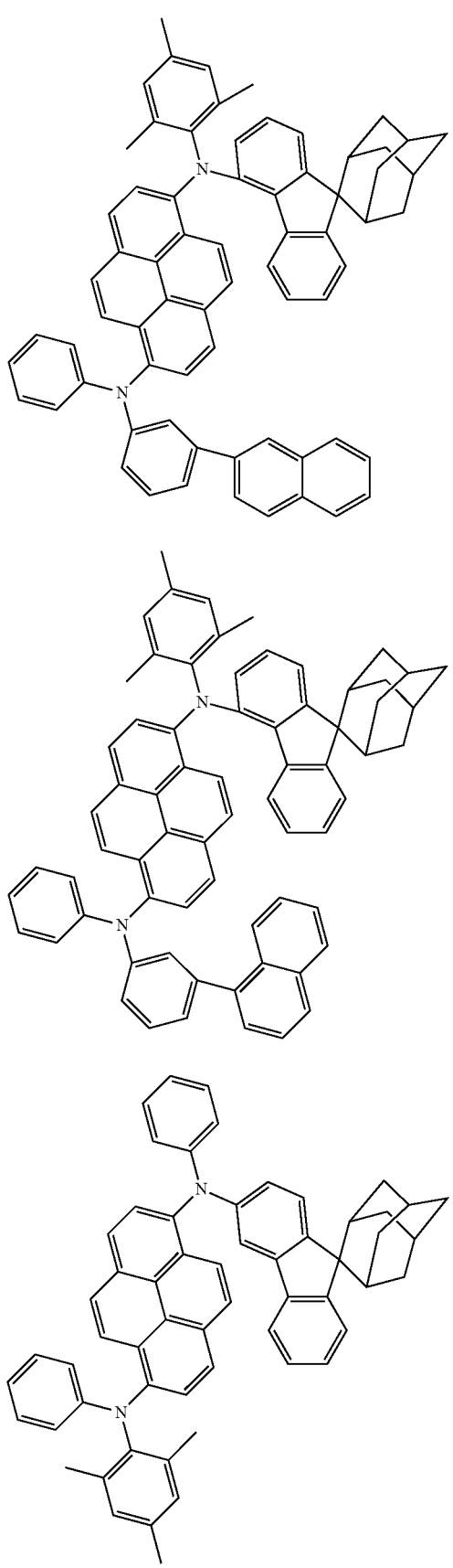

-continued
23
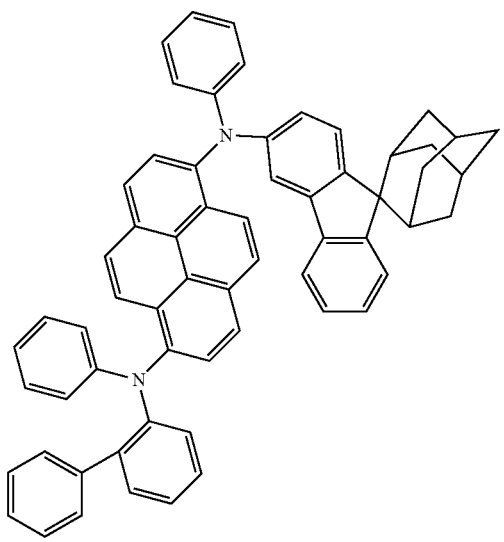
24
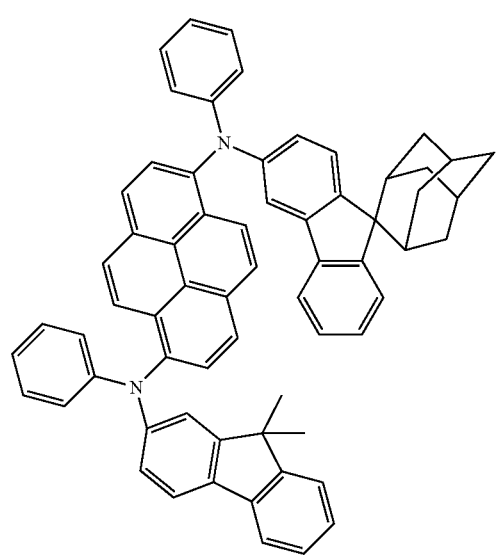
25
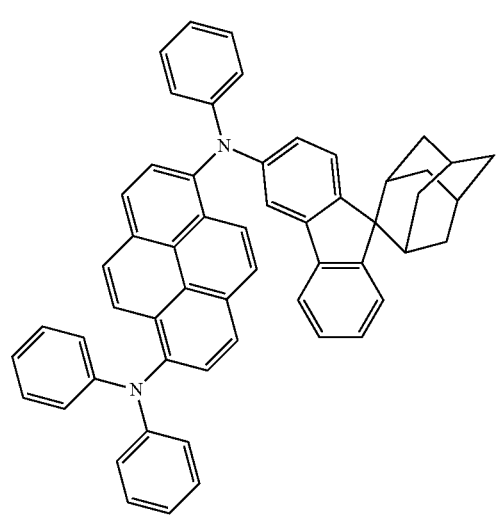
-continued
26
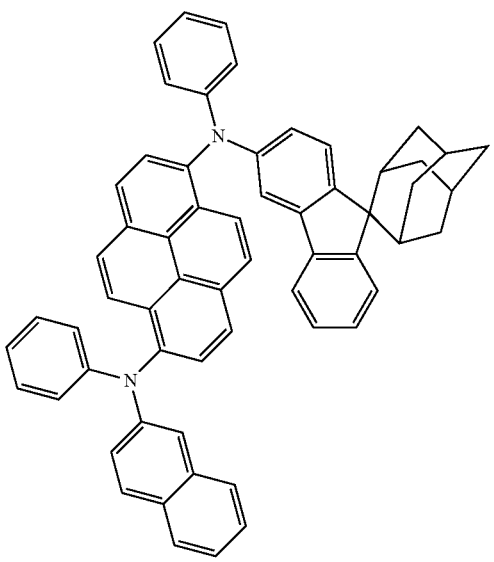
27
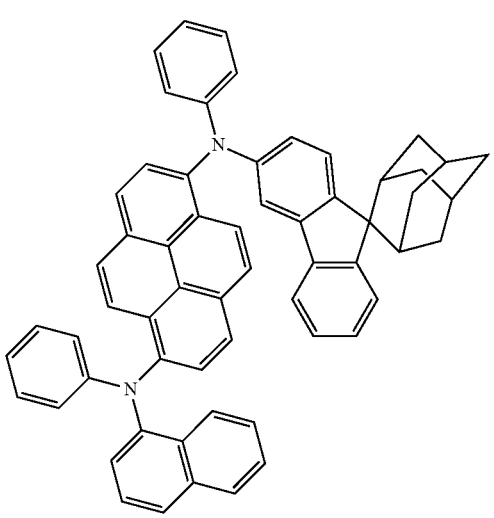
28
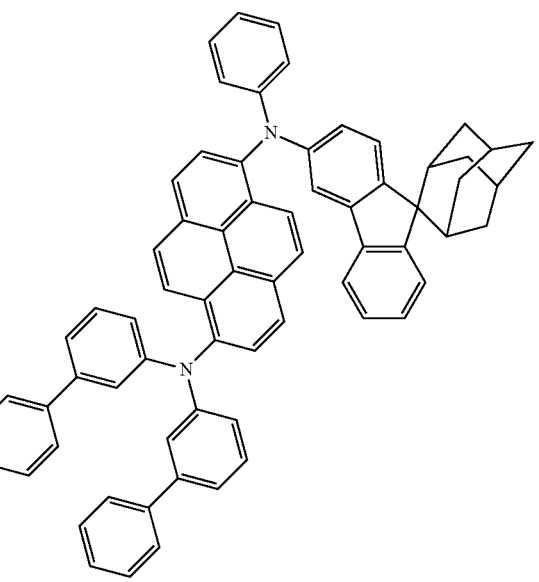

157
-continued
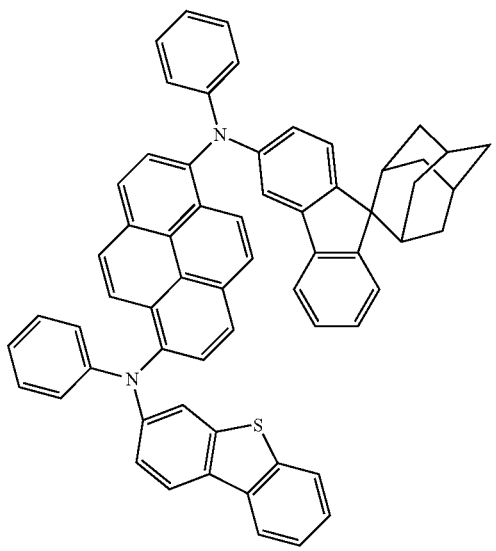
158
-continued
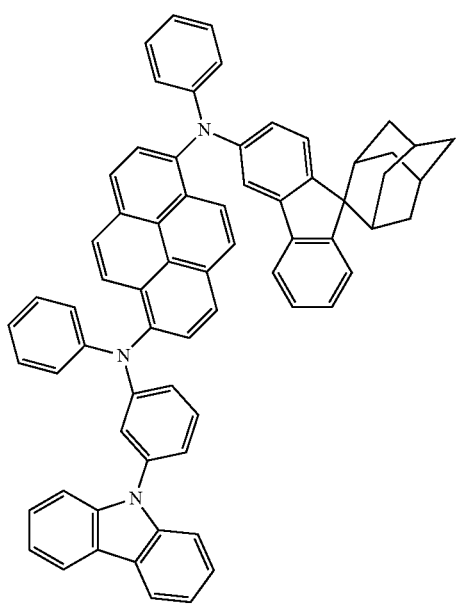
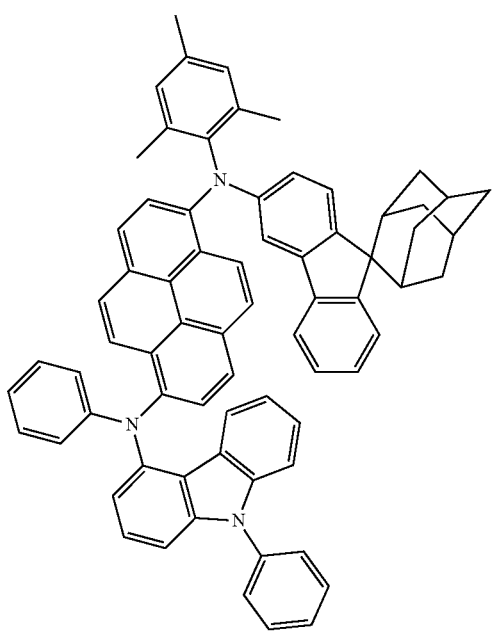
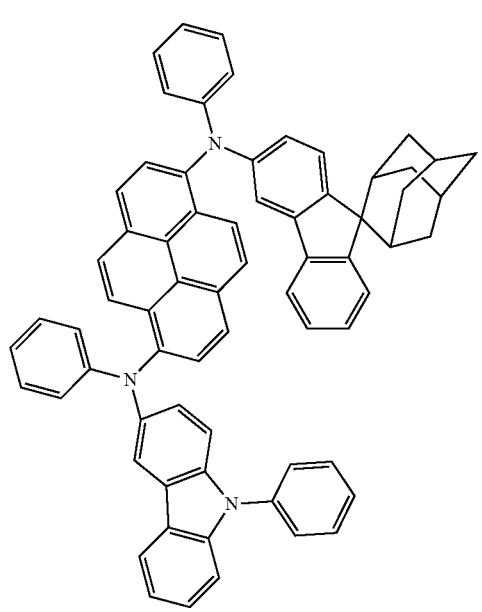

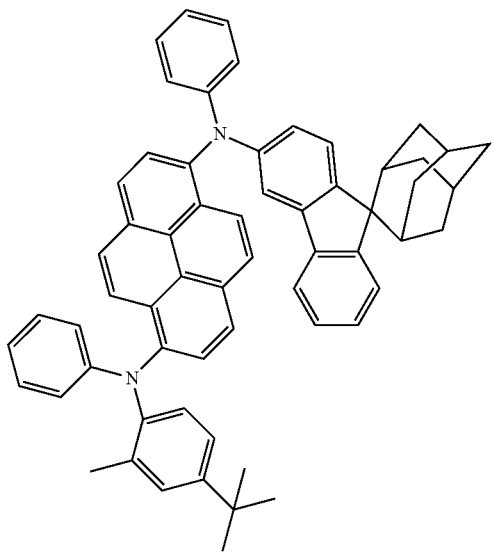
33
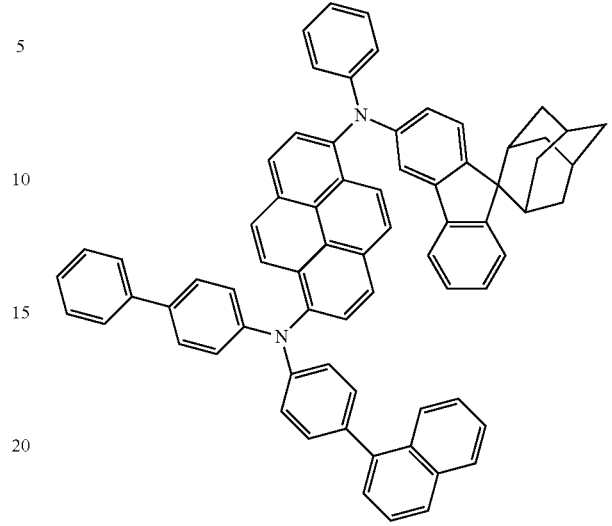
36
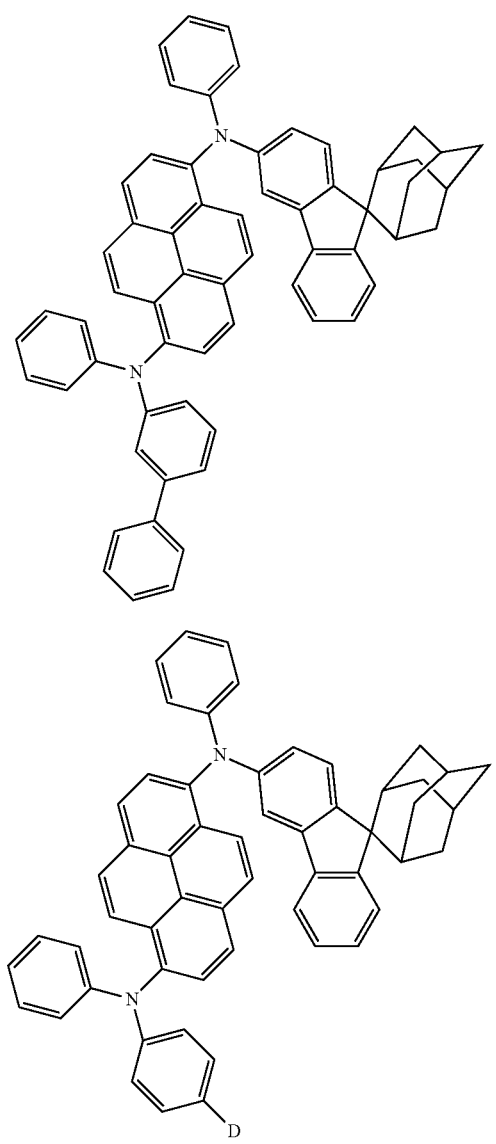
34
35
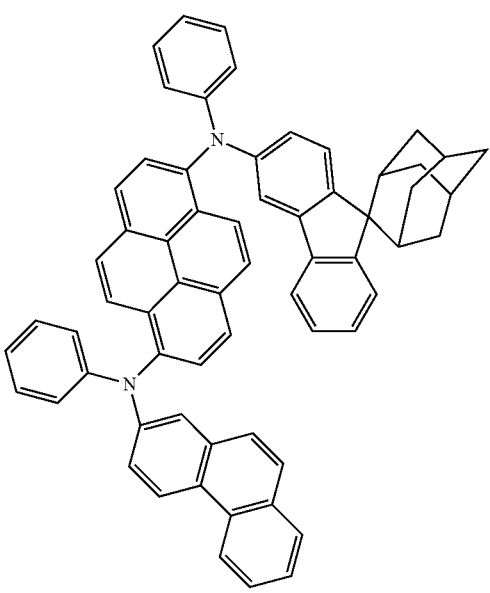
37

161
-continued
38
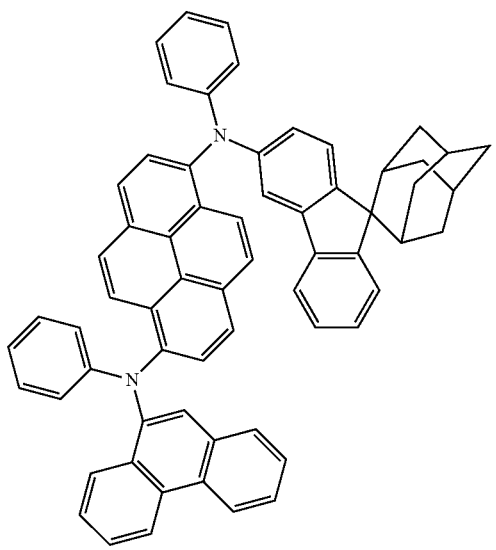
39
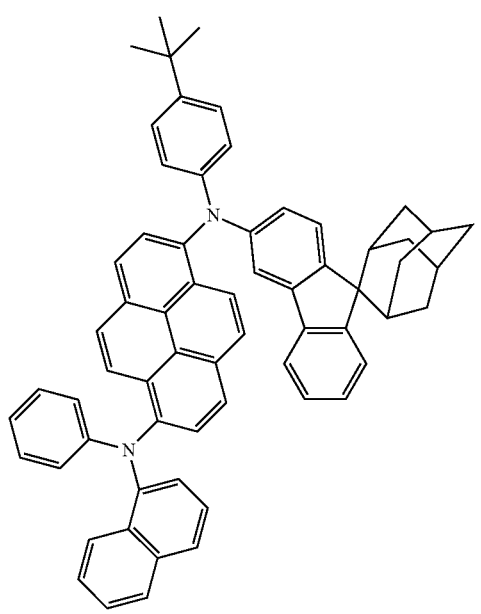
162
-continued
40
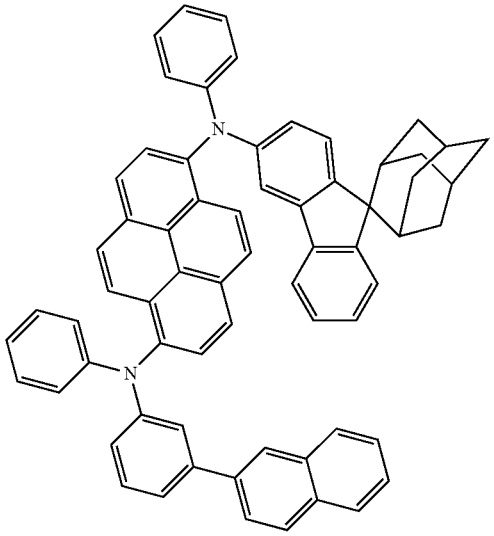
41
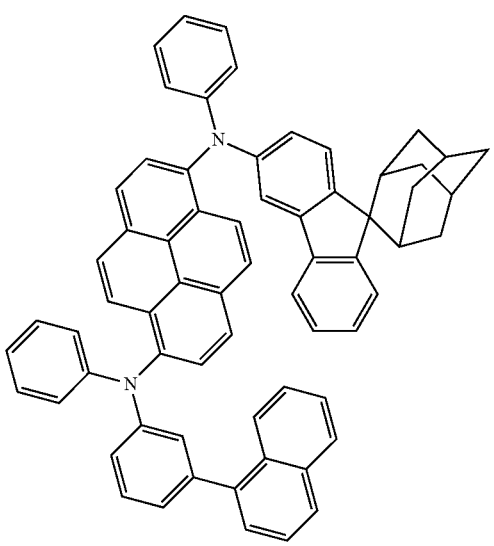
43
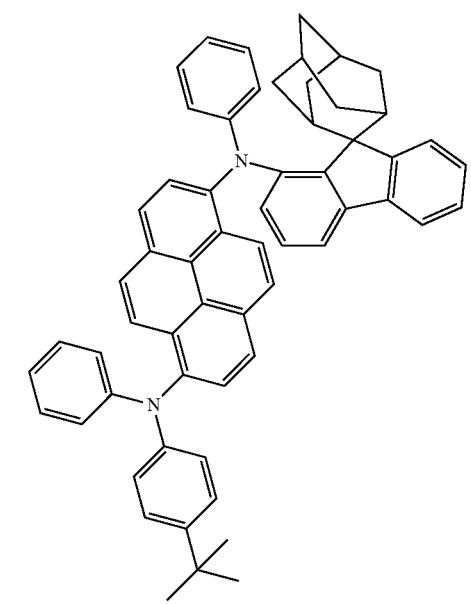

44
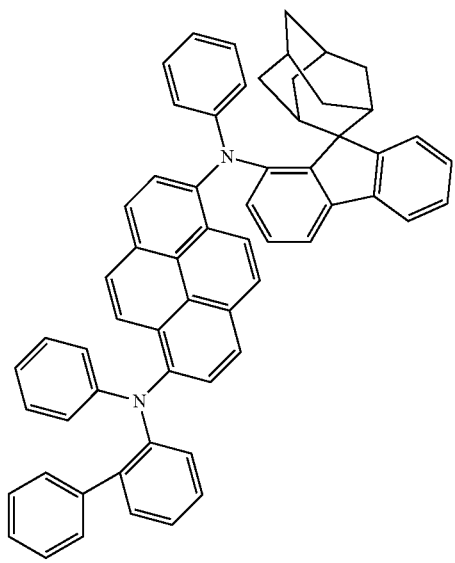
45
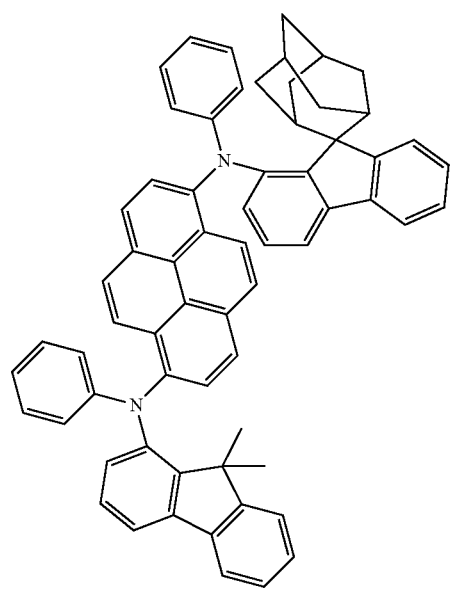
46
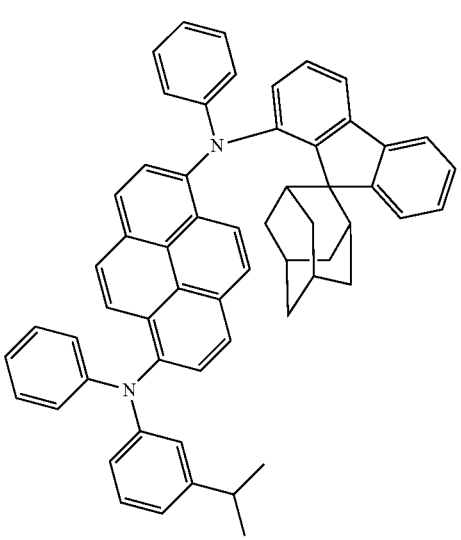
47
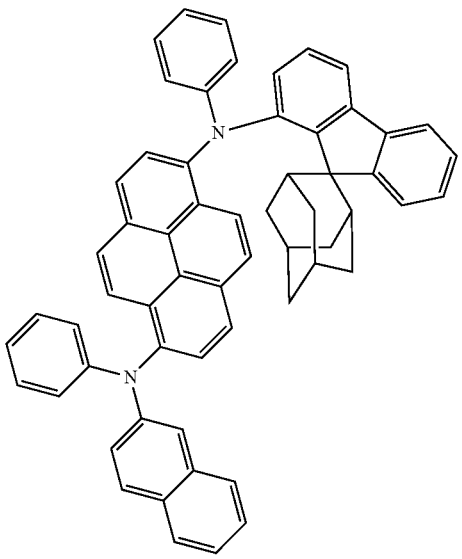
48
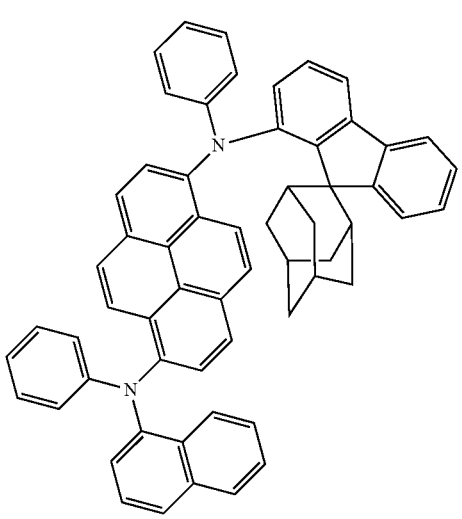
49
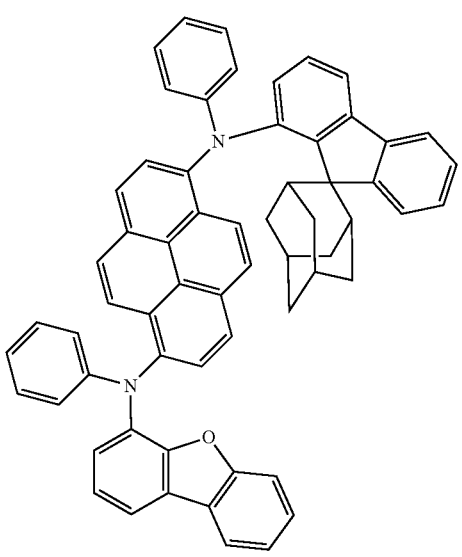

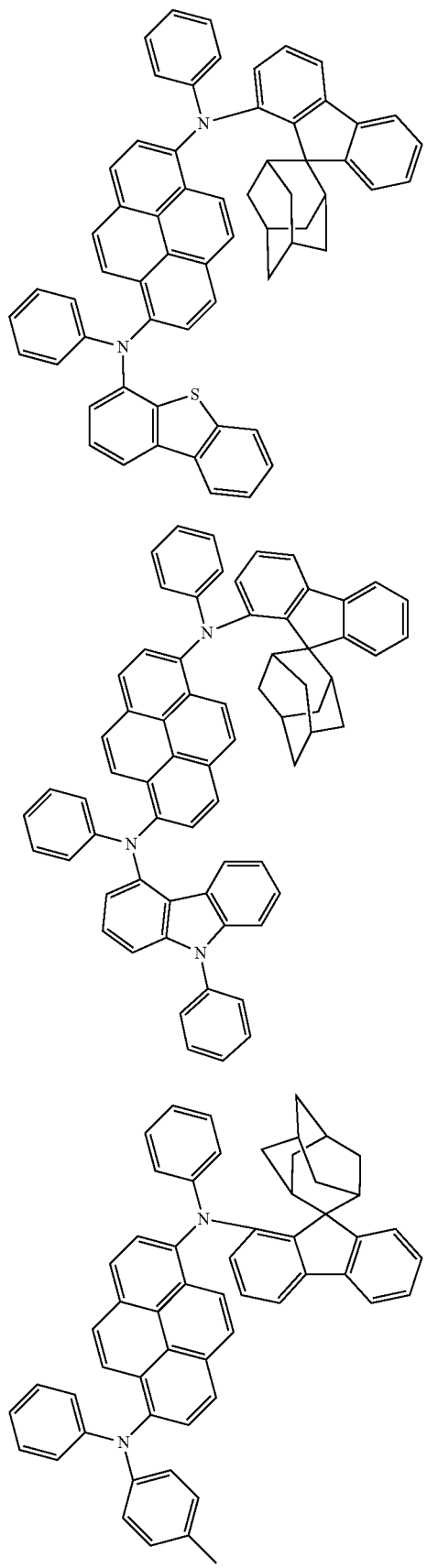

167
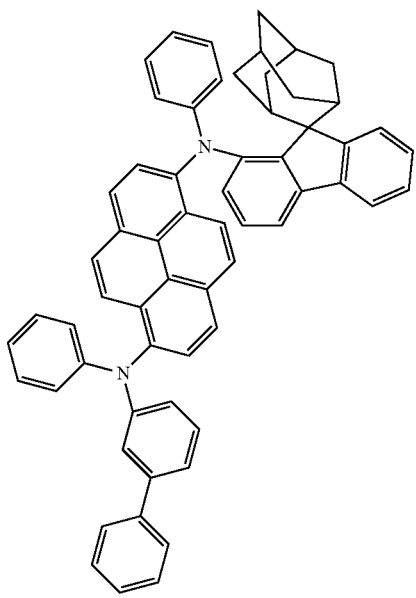
168
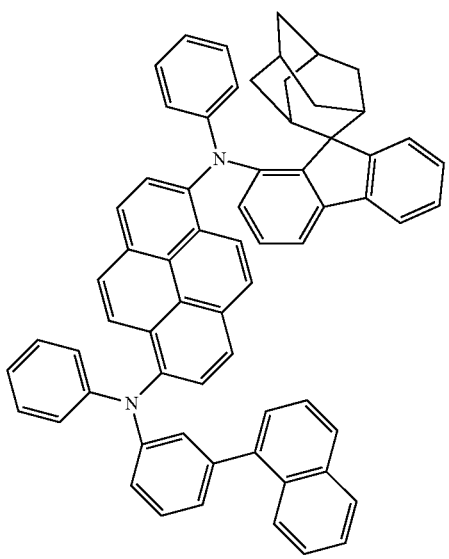
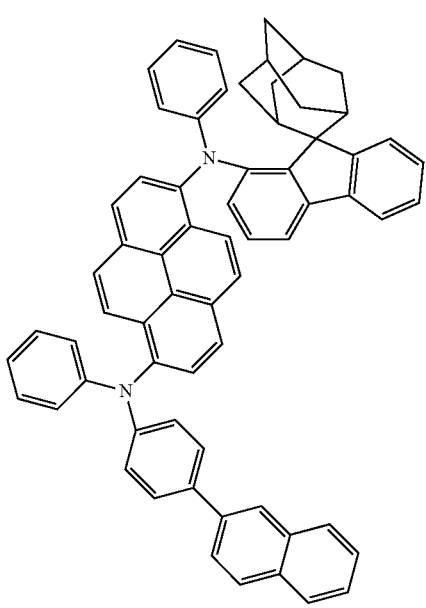
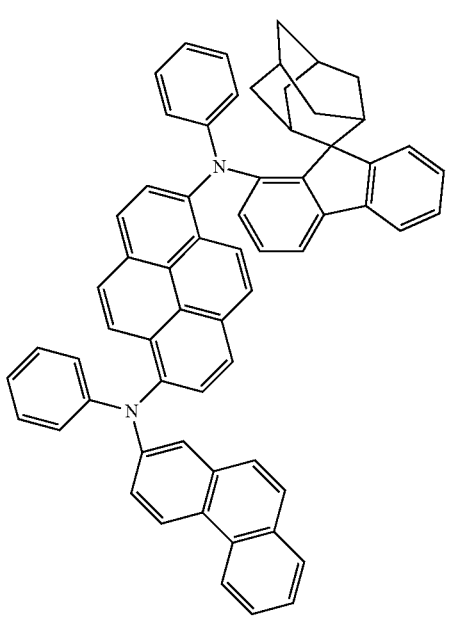

169
-continued
59
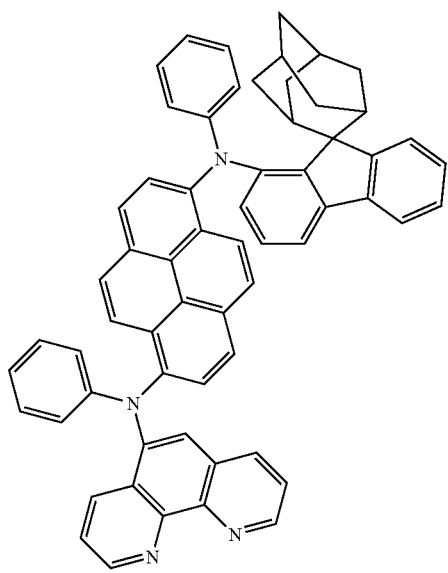
60
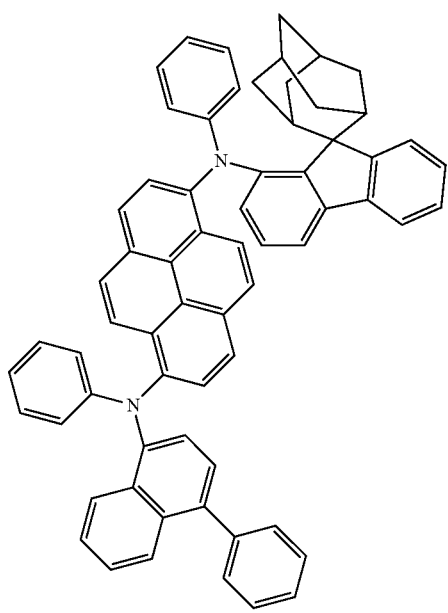
170
-continued
61
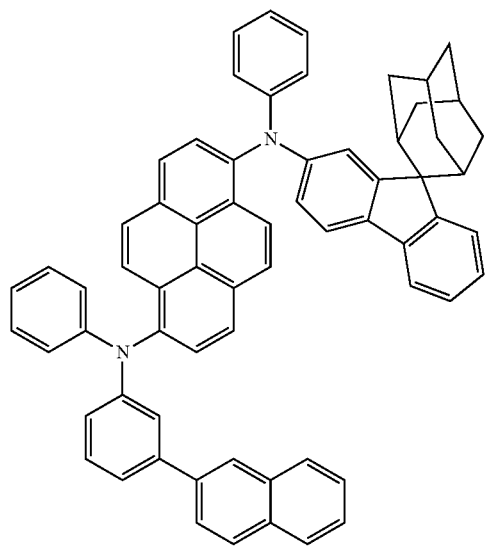
62
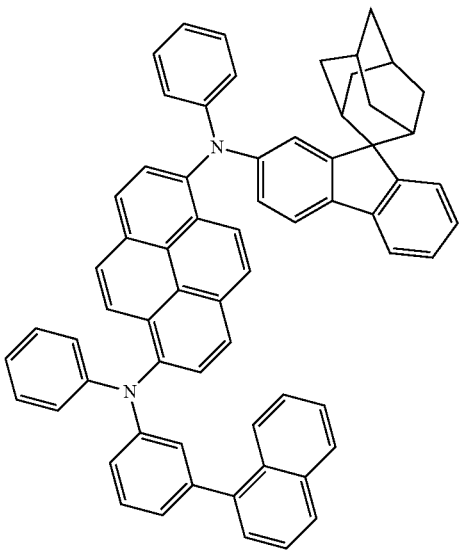

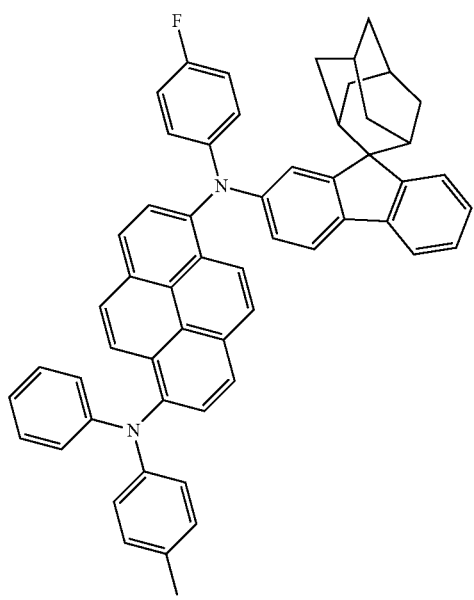
64
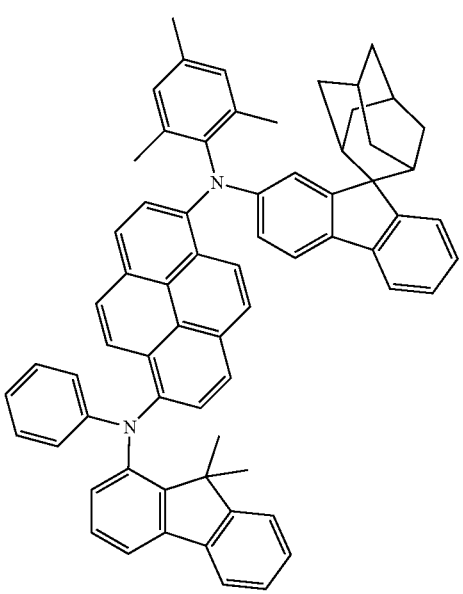
66
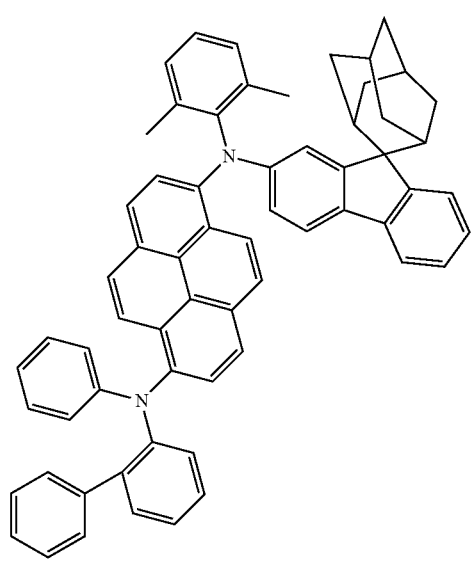
65
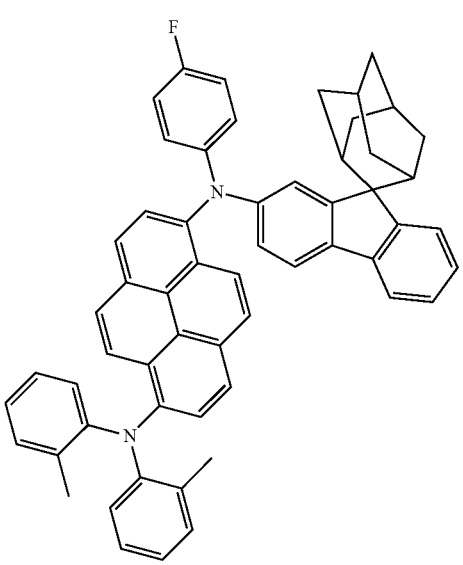
67

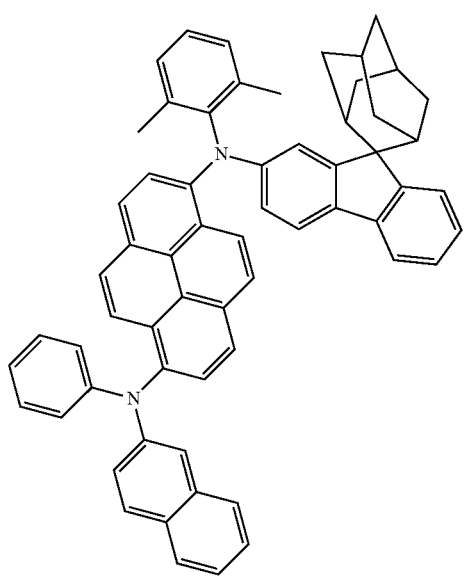
68
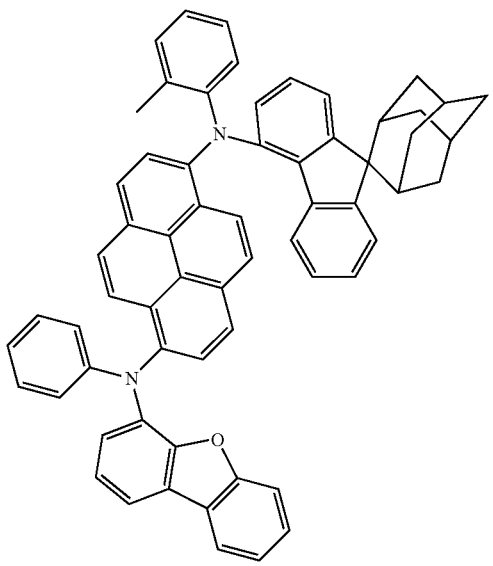
70
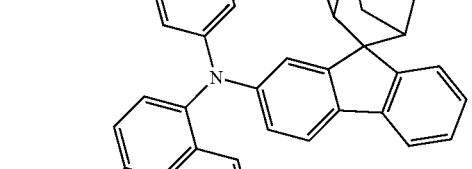
69
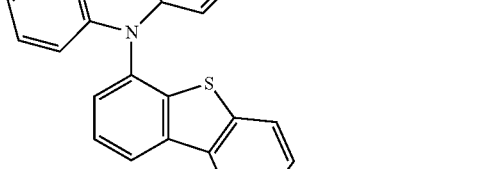
71

175
72
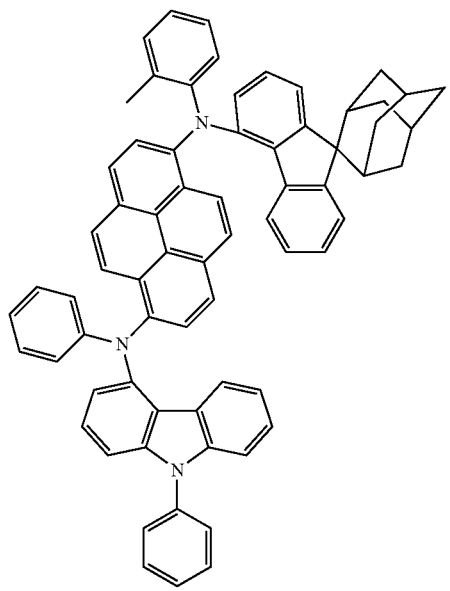
73
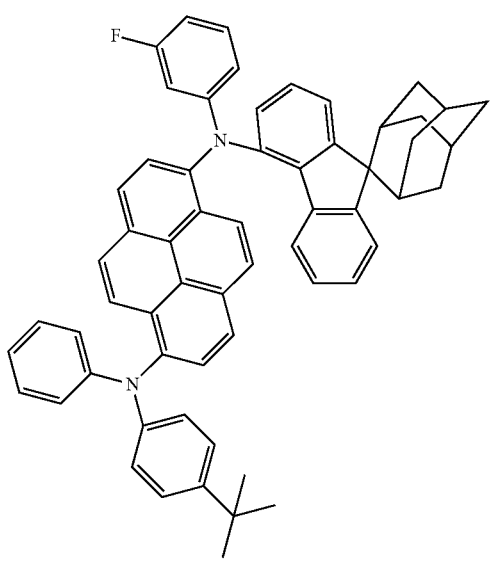
176
74
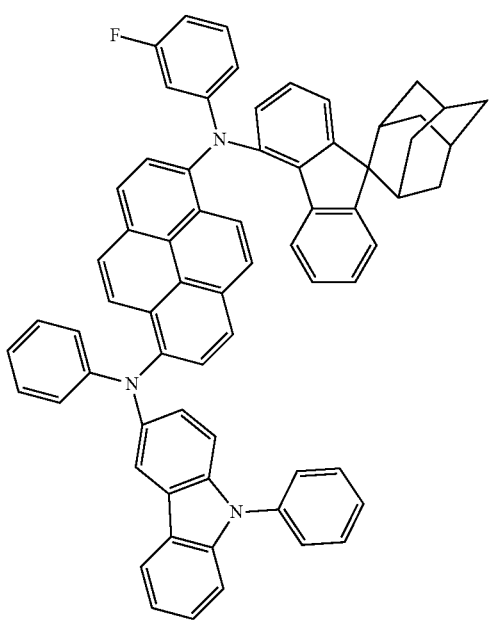
75
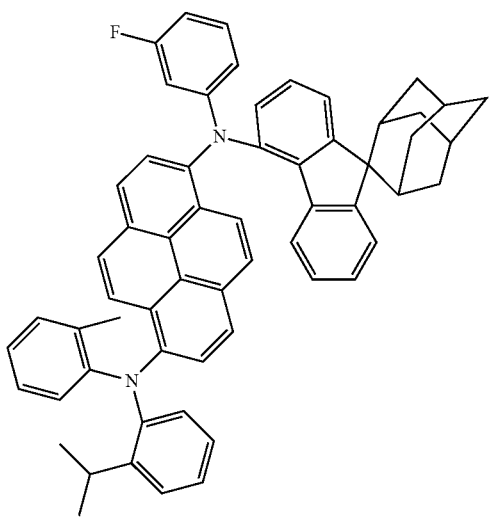

176
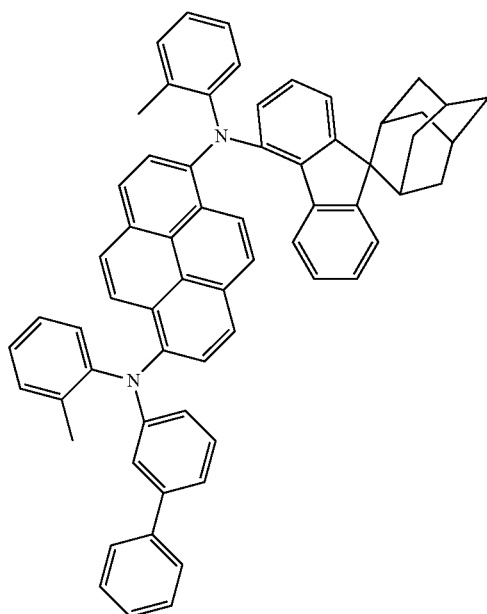
77
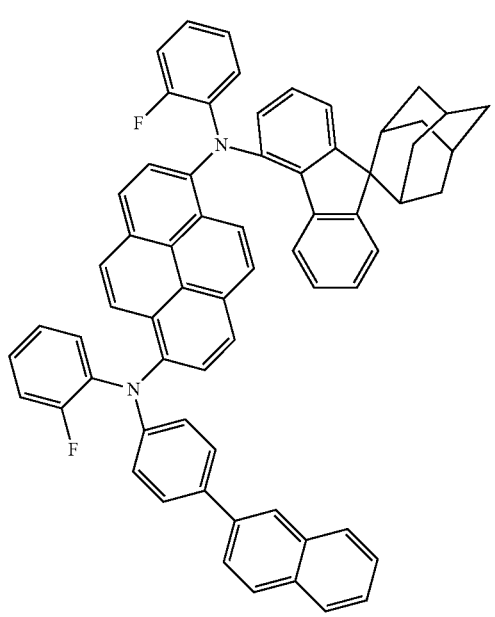
178
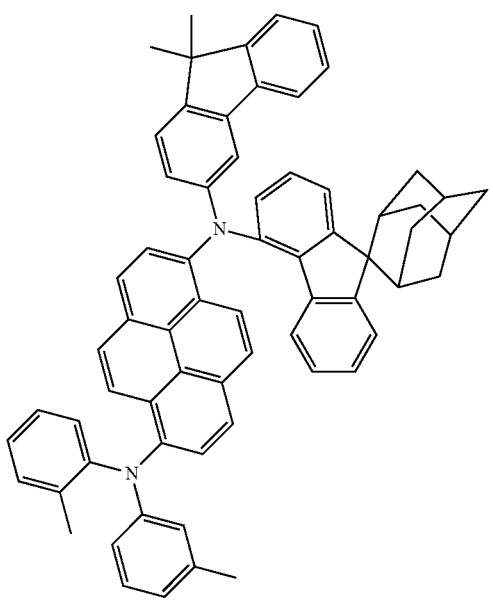
79
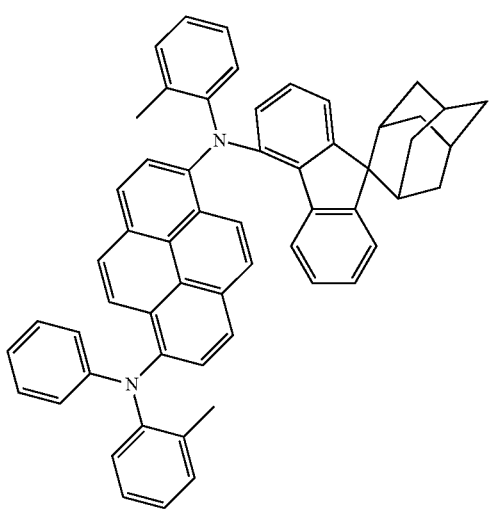

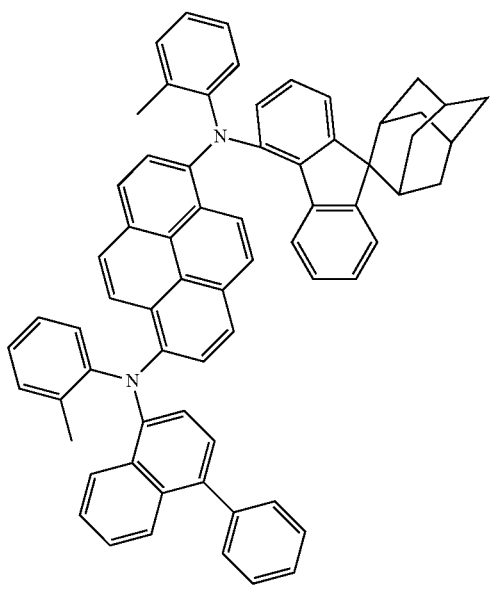
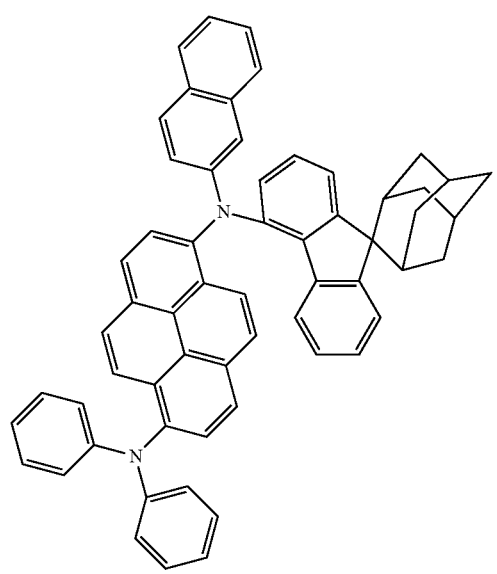
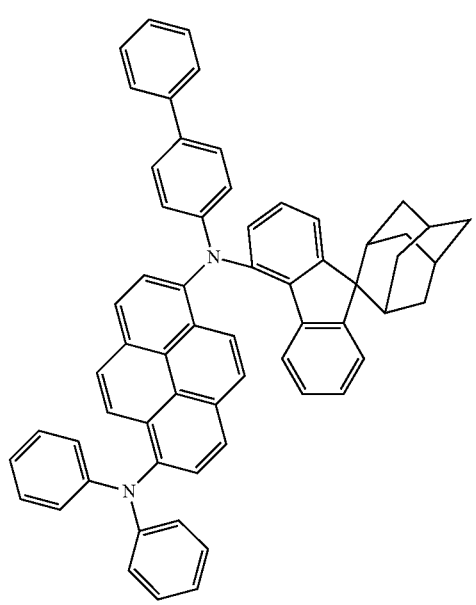
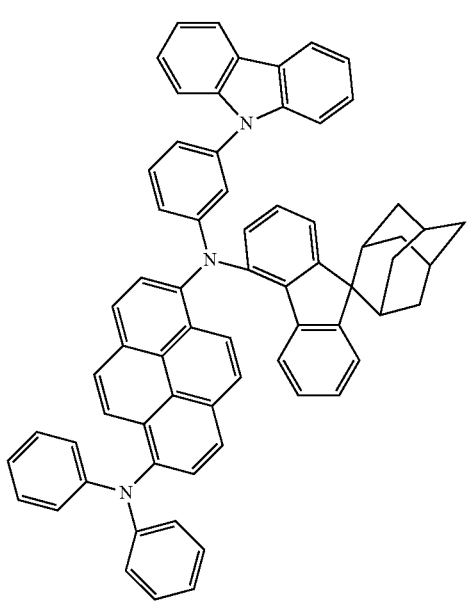

86
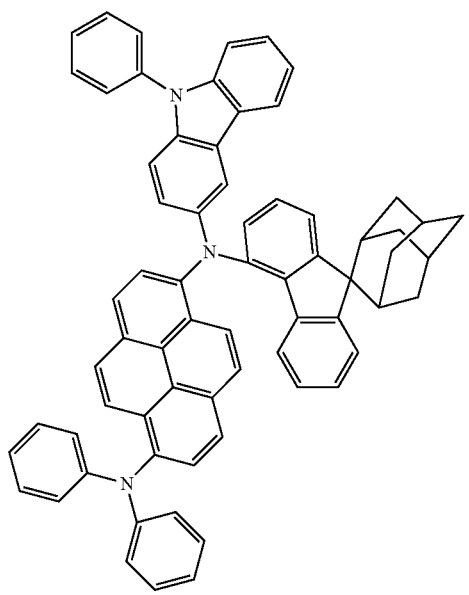
87
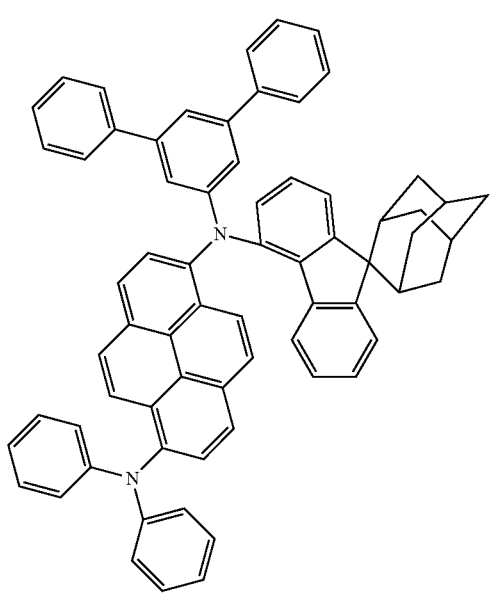
88
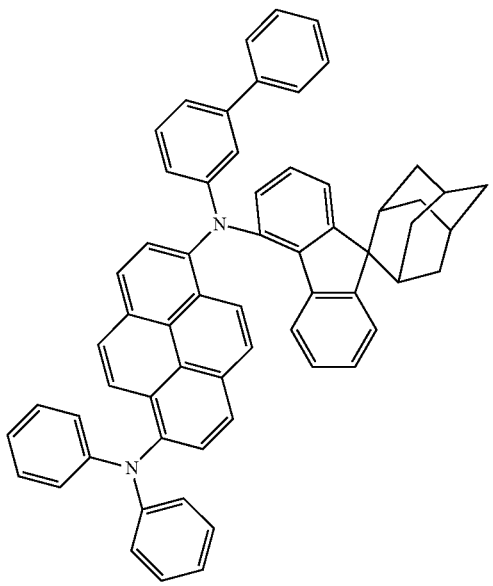
89
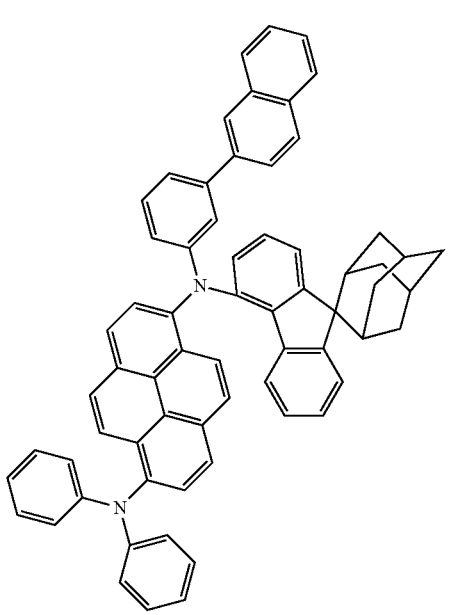

183
-continued
184
-continued
90
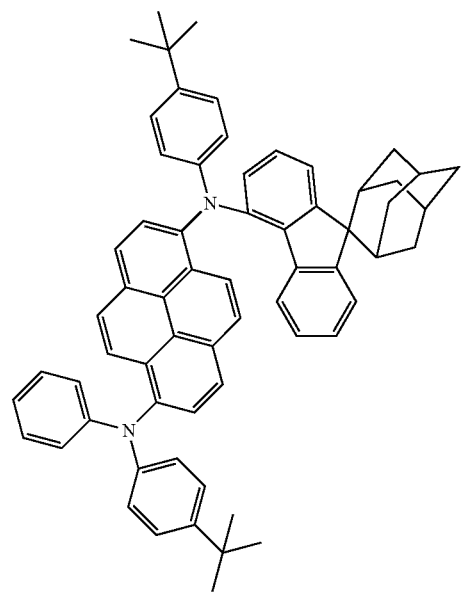
92
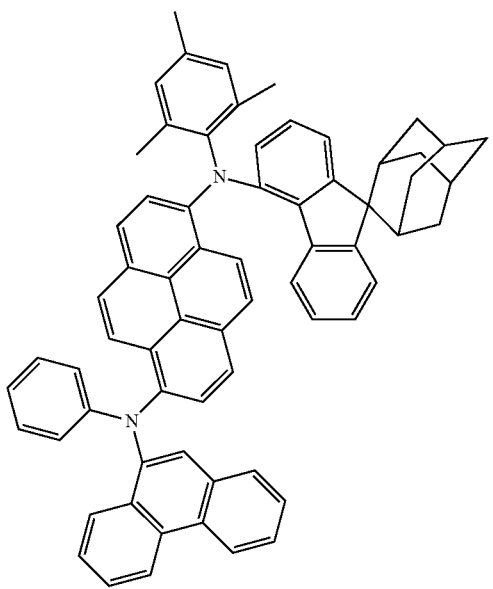
93
91
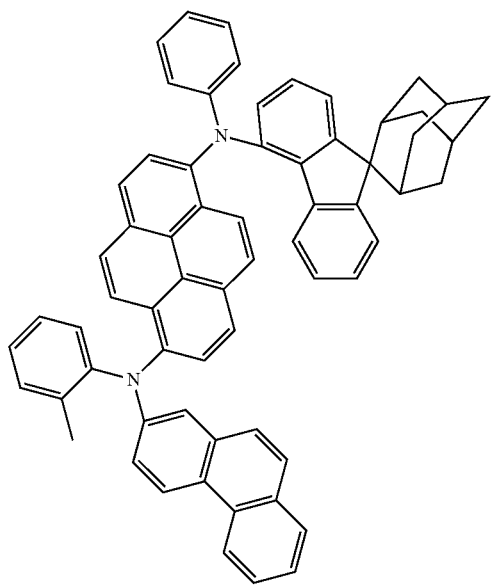
94
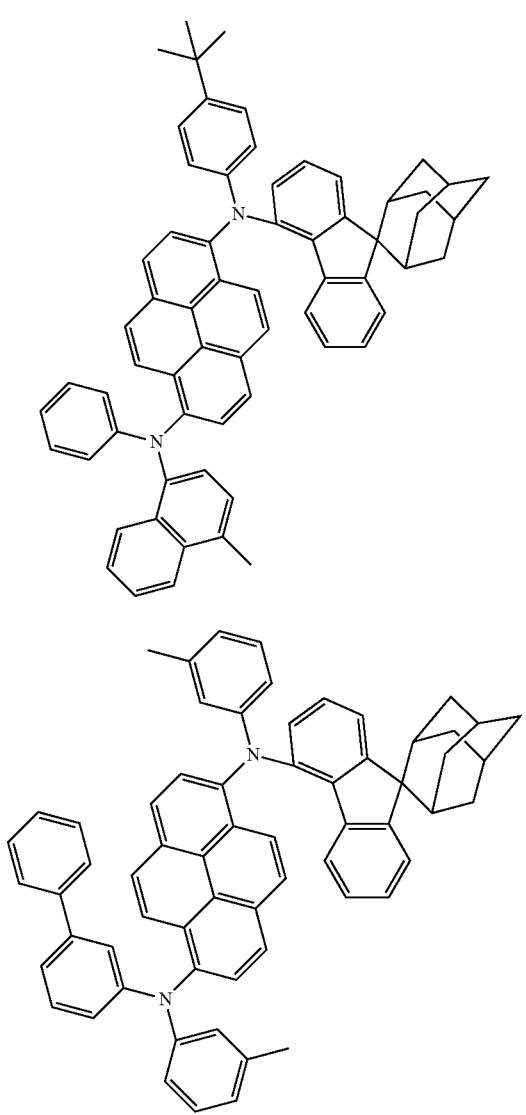

185
-continued
95
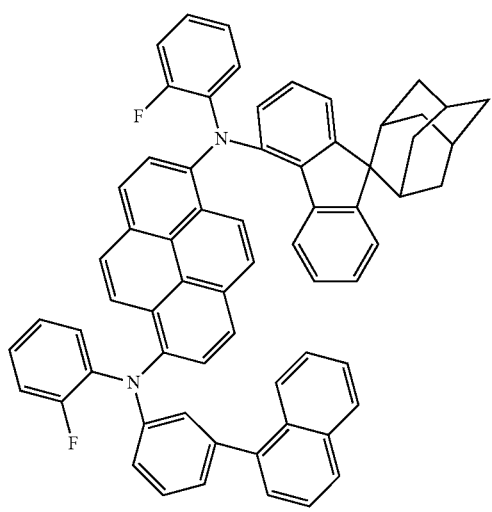
97
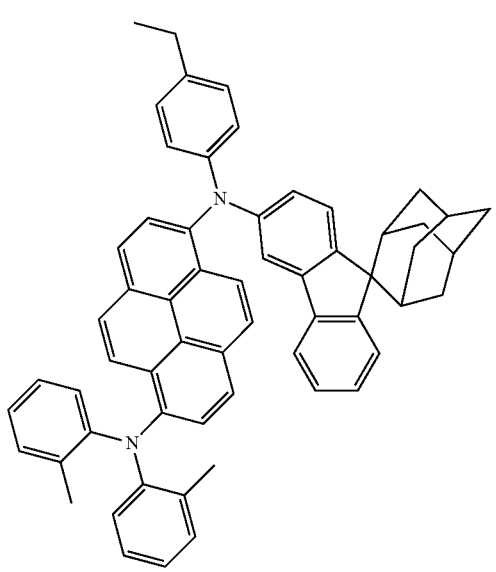
98
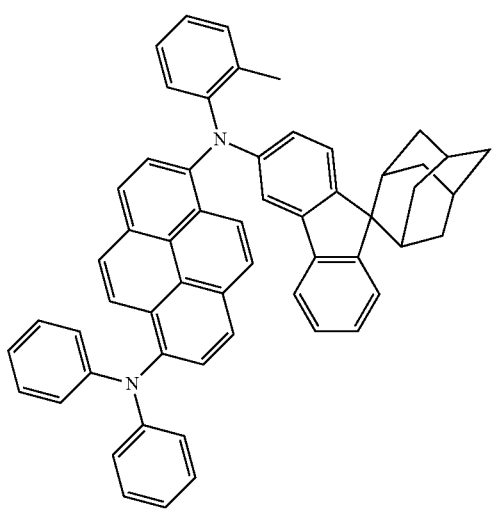
186
-continued
99
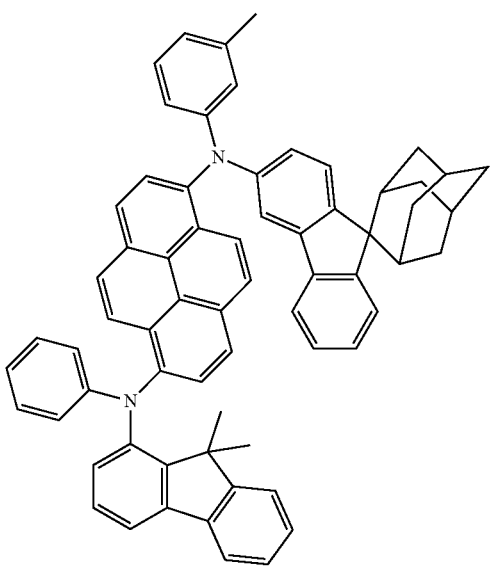
100
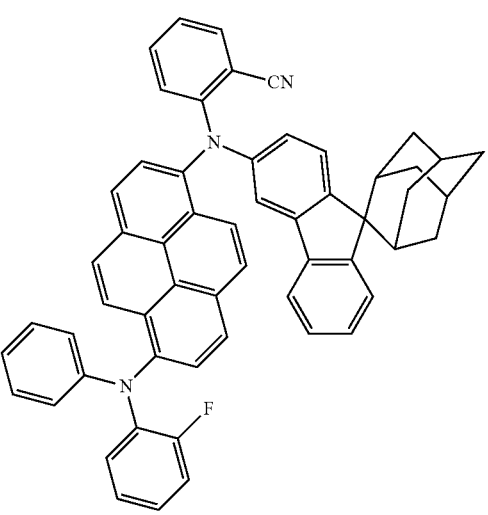
101
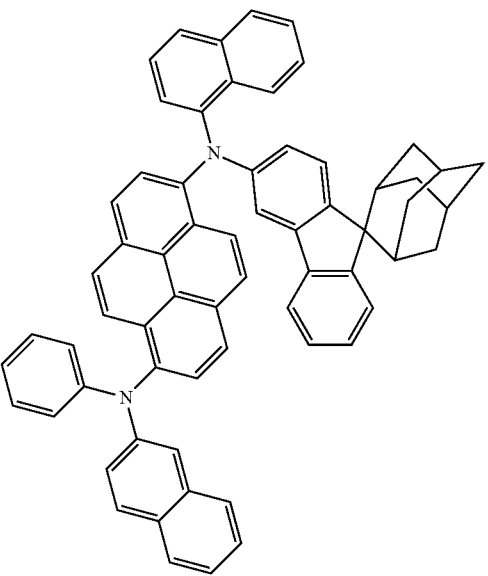

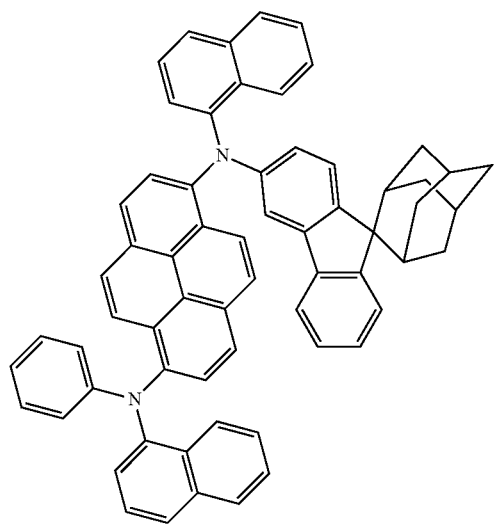
102
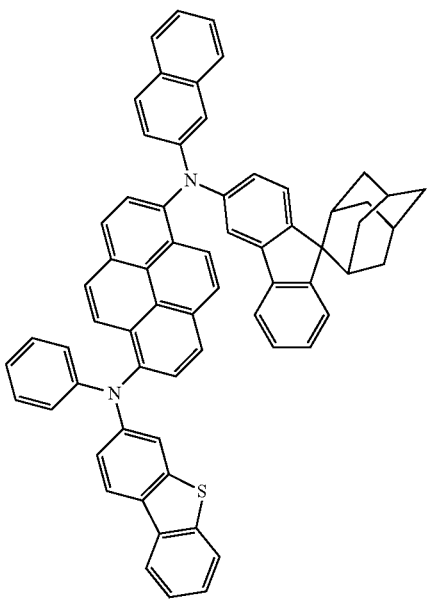
104
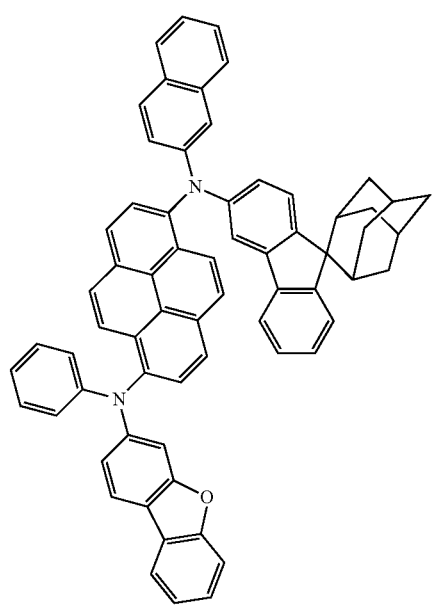
103
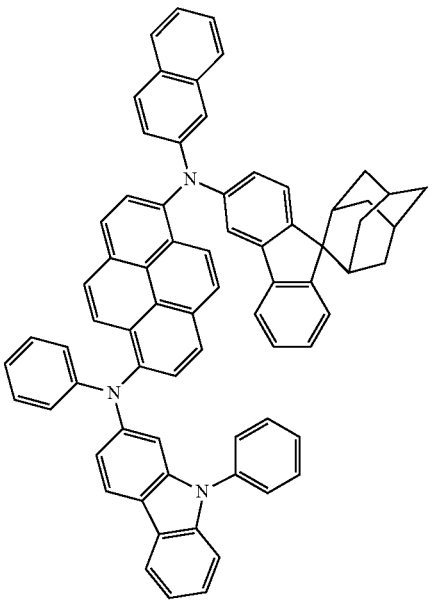
105

189
-continued
190
-continued
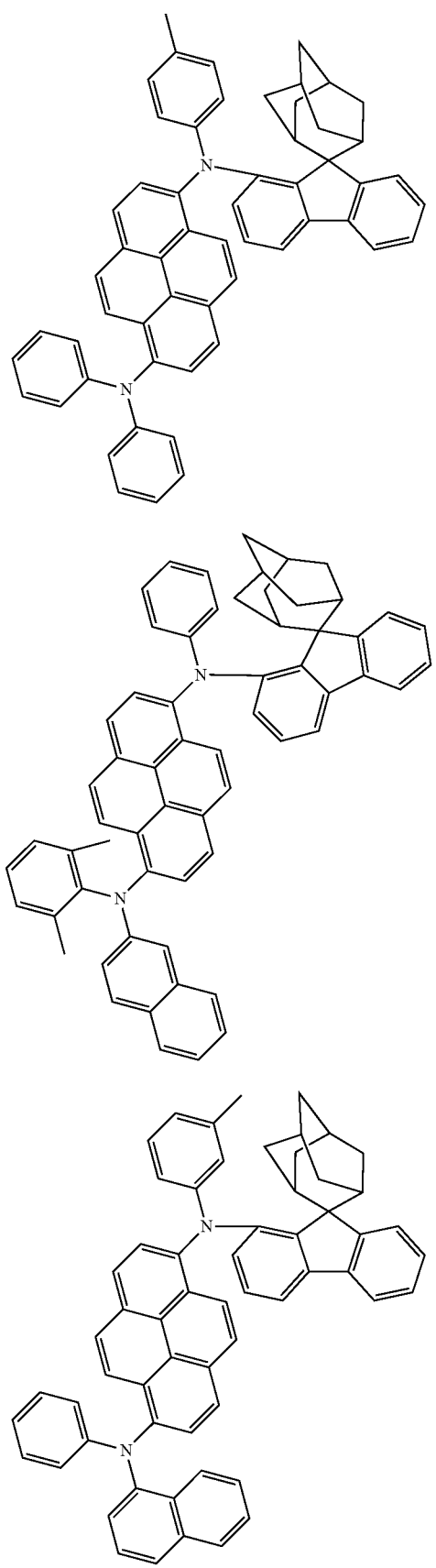
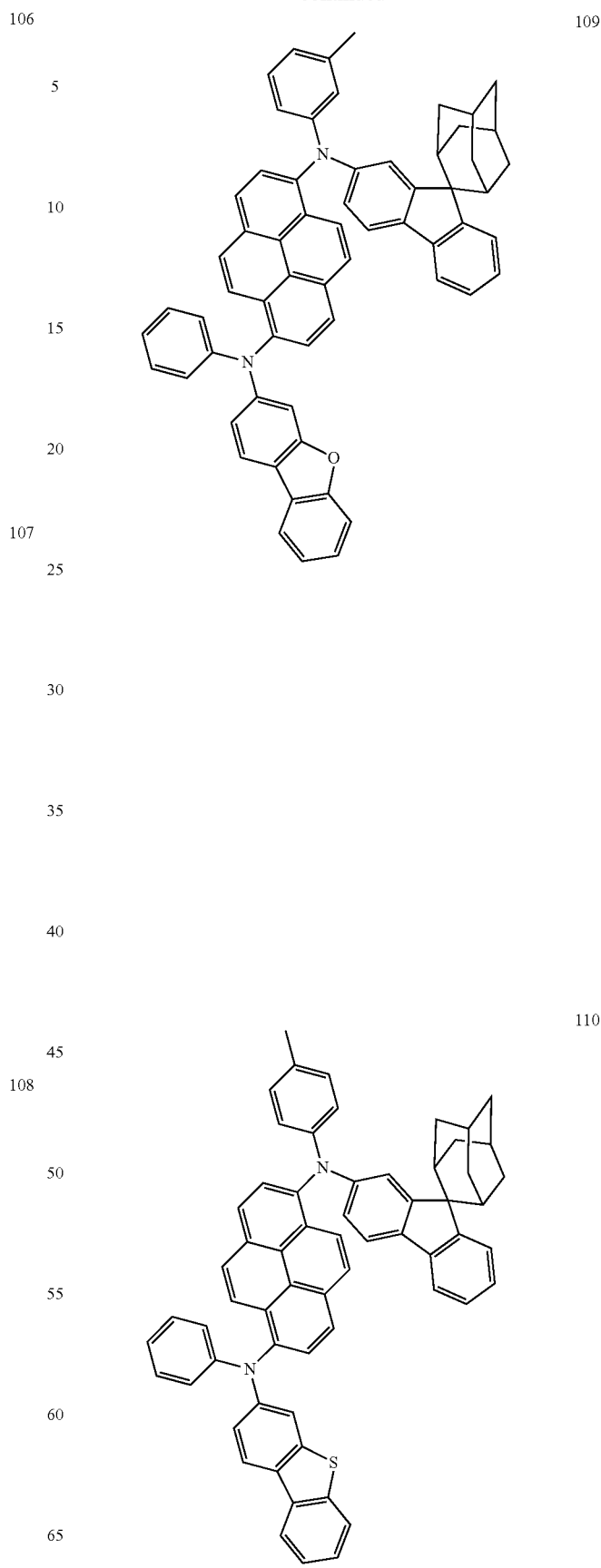

191
-continued
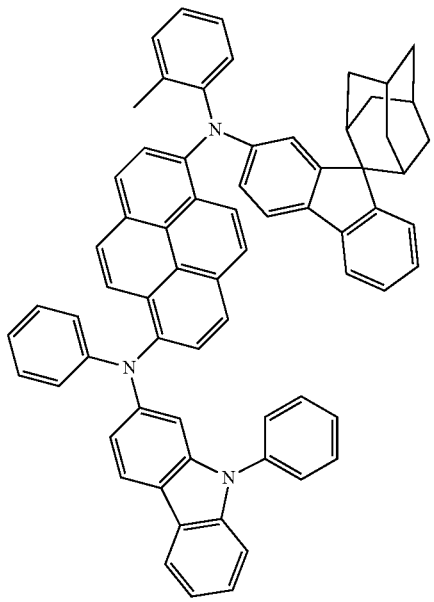
111
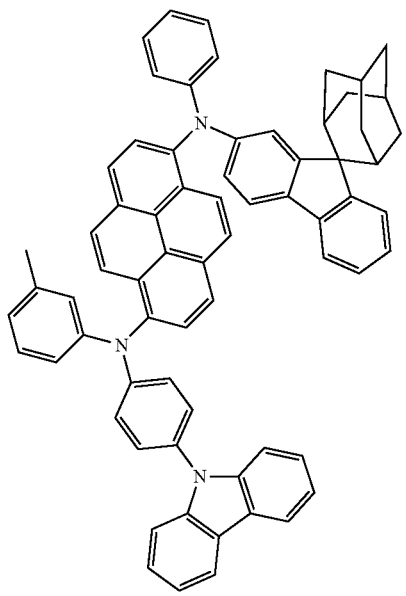
112
192
-continued
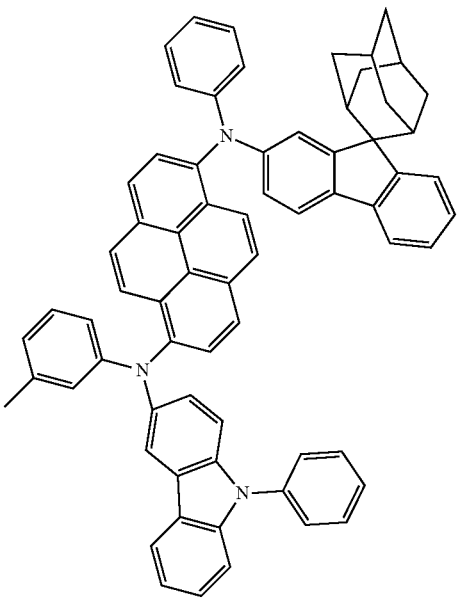
113
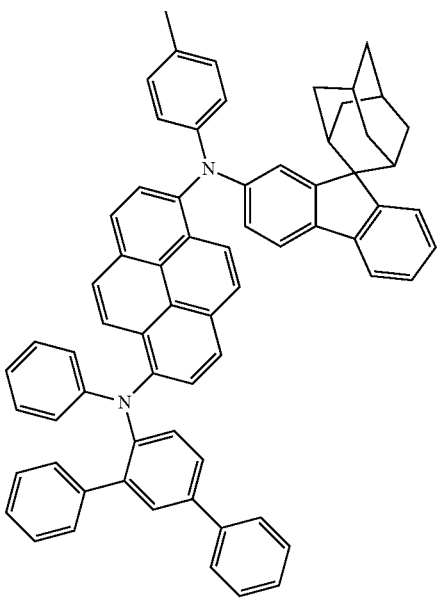
114

193
-continued
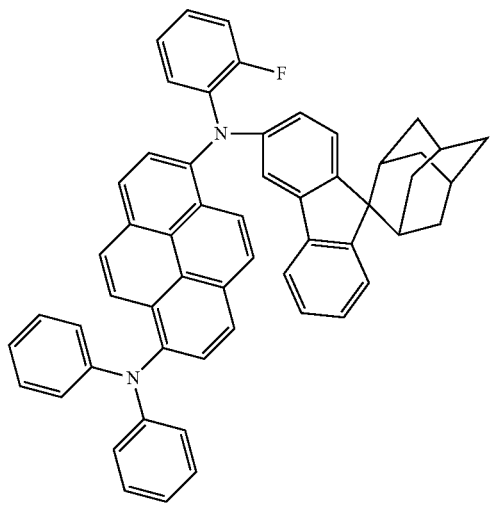
115
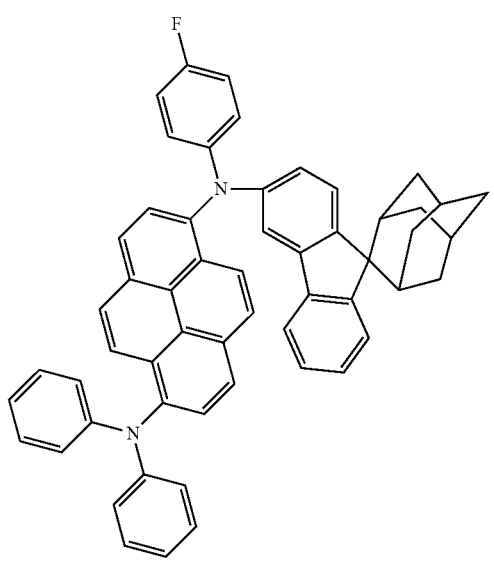
116
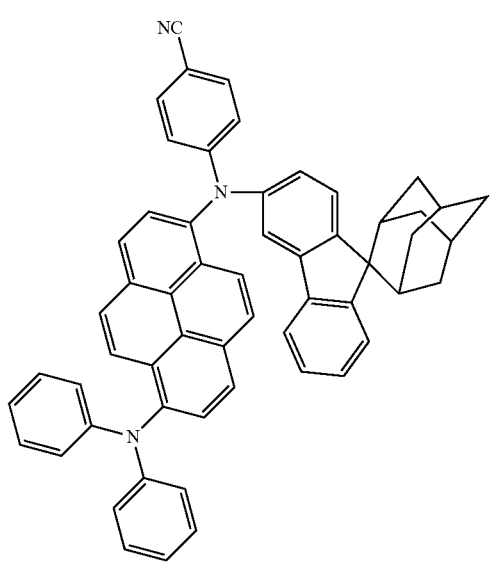
117
194
-continued
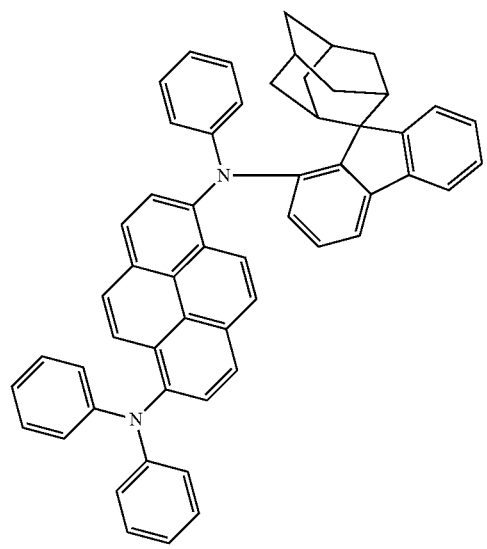
118
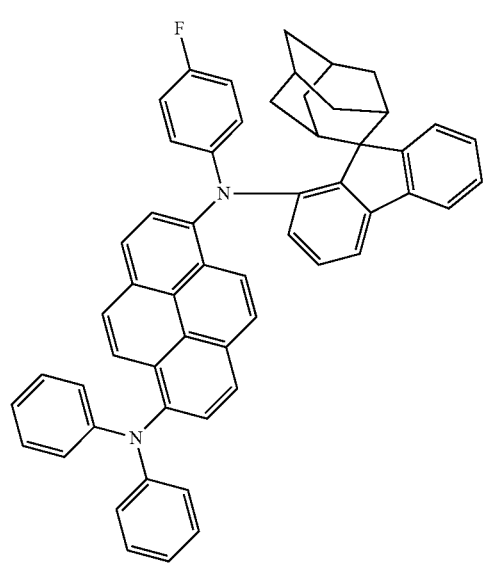
119
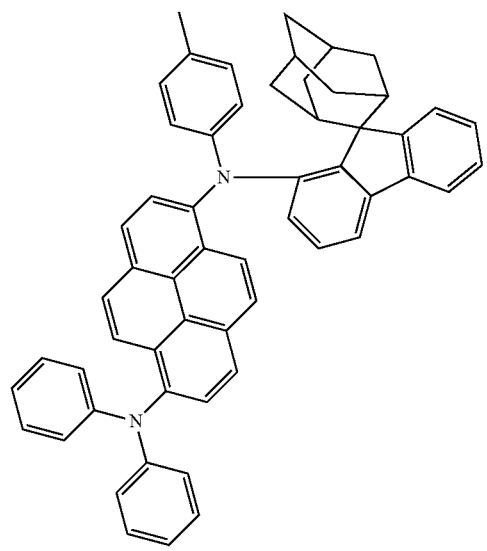
120

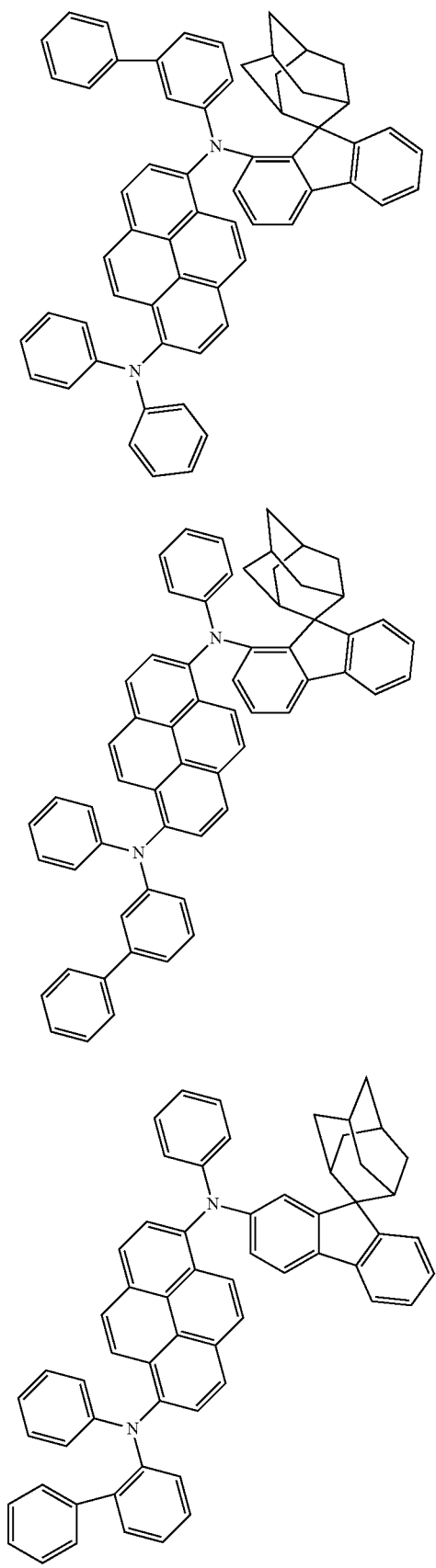

126
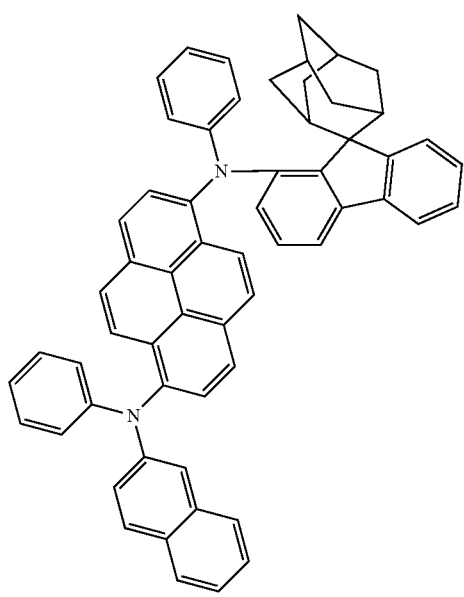
127
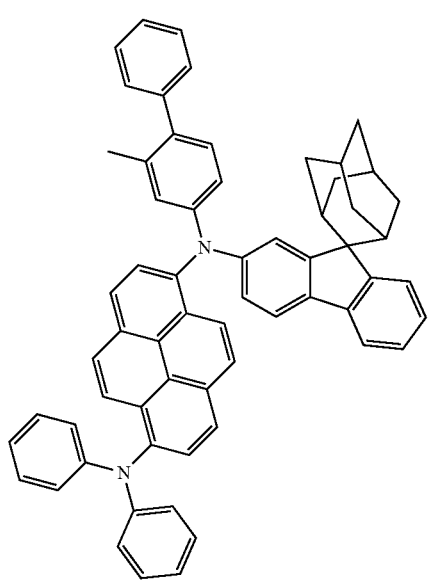
128
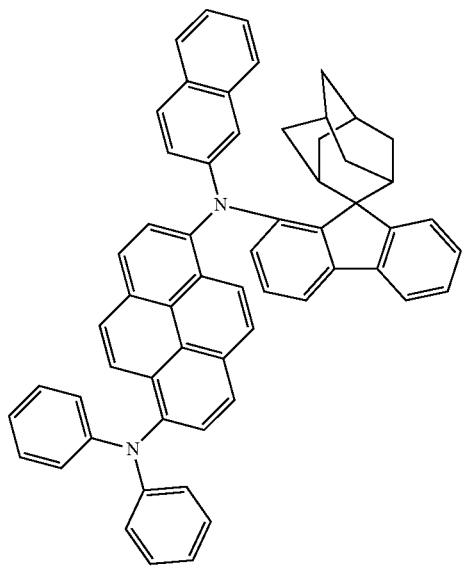
129
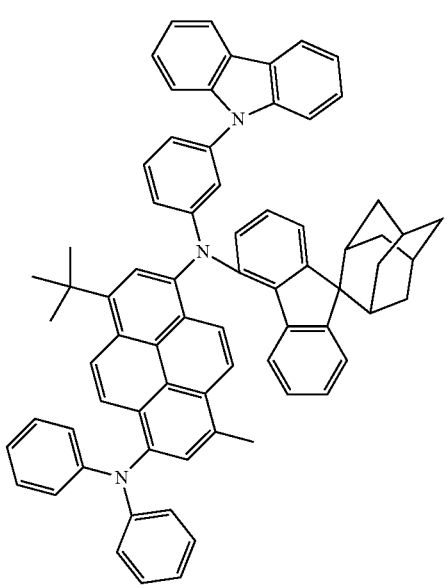

199
-continued
130
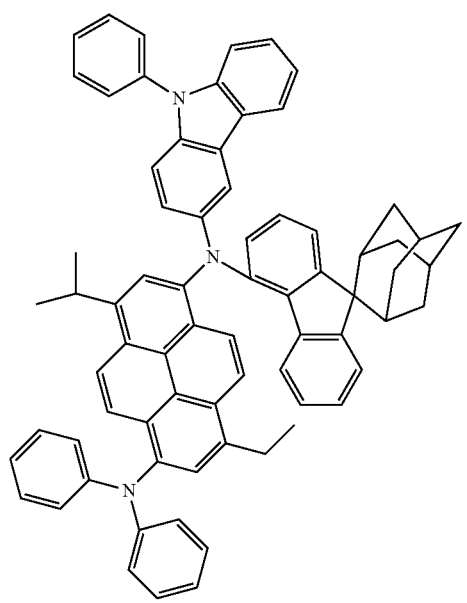
134
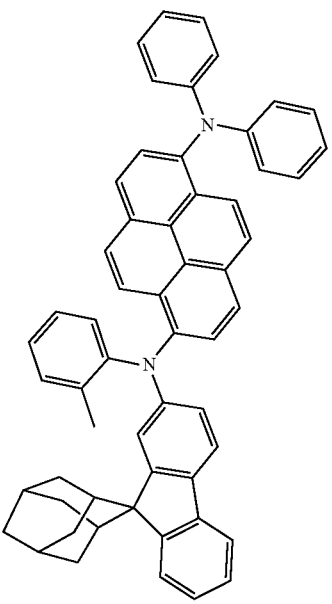
133
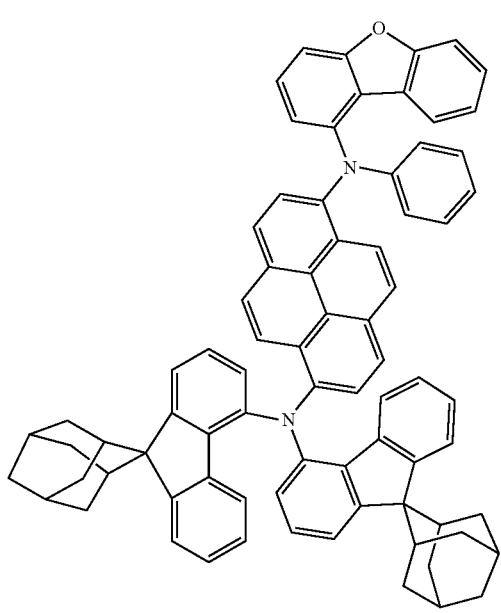
135
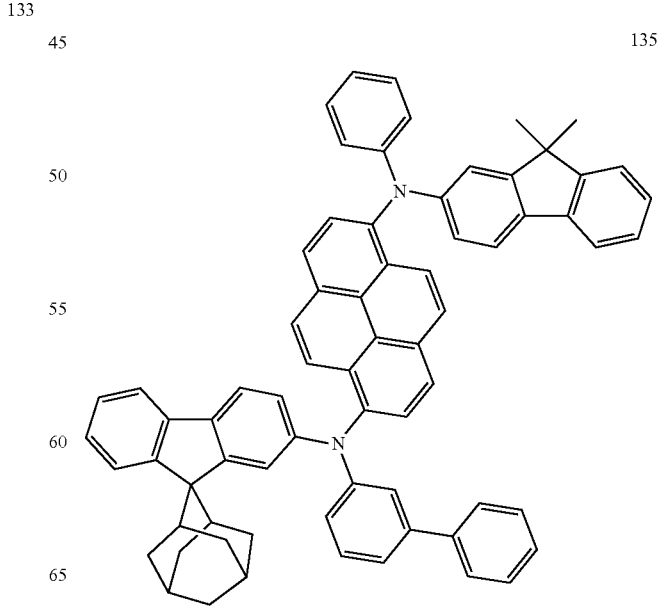

201
-continued

137
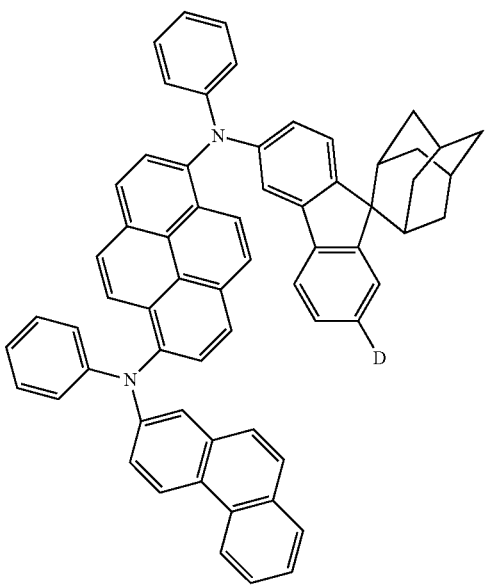

138
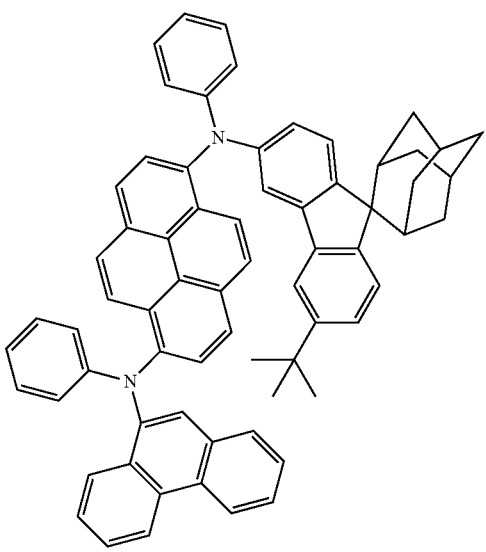

202
-continued

145
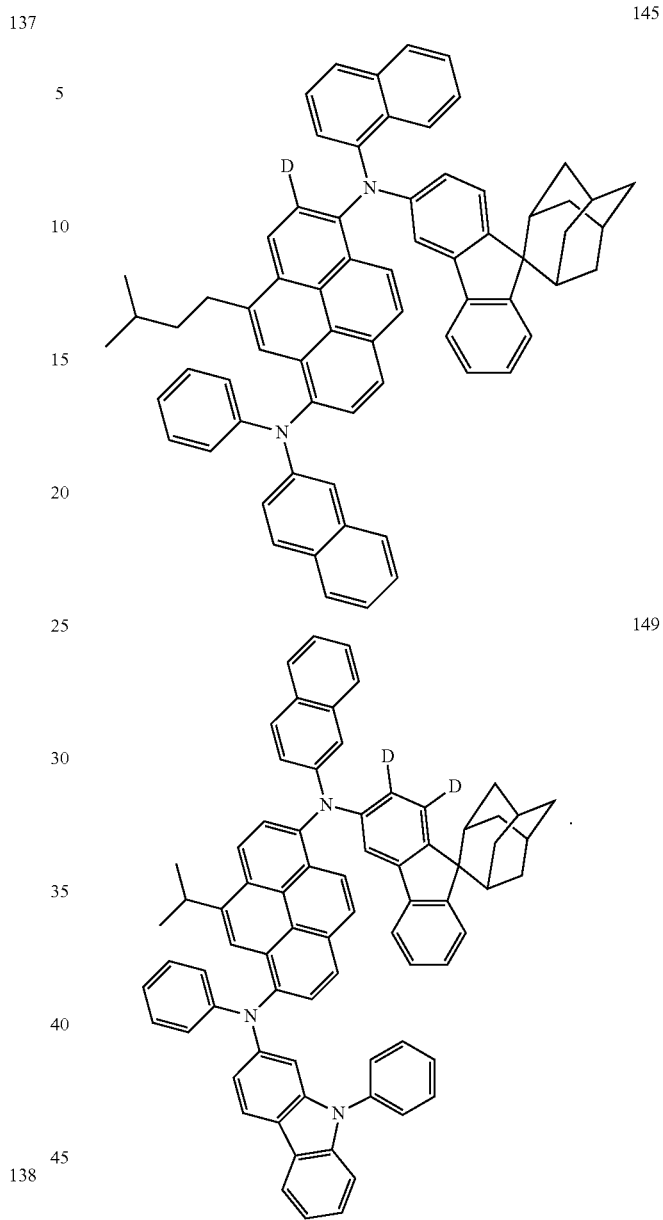

149

7. An organic electroluminescent device, comprising an anode and a cathode that are arranged oppositely, and a functional layer arranged between the anode and the cathode,
wherein the functional layer comprises the nitrogen-containing compound according to claim 1.

8. The organic electroluminescent device according to claim 7, wherein the functional layer comprises an organic electroluminescent layer, and the organic electroluminescent layer comprises the nitrogen-containing compound.

9. The organic electroluminescent device according to claim 8, wherein the organic electroluminescent layer comprises a guest material, and the guest material comprises the nitrogen-containing compound.

10. An electronic apparatus, comprising the organic electroluminescent device according to claim 7.

11. An electronic apparatus, comprising the organic electroluminescent device according to claim 8.

12. An electronic apparatus, comprising the organic electroluminescent device according to claim 9.

\* \* \* \* \*